US006953806B2

(12) United States Patent
Ackermann et al.

(10) Patent No.: US 6,953,806 B2
(45) Date of Patent: Oct. 11, 2005

(54) SUBSTITUTED CYCLOHEXANE DERIVATIVES

(75) Inventors: Jean Ackermann, Riehen (CH); Johannes Aebi, Basel (CH); Henrietta Dehmlow, Grenzach-Wyhlen (DE); Georges Hirth, Huningue (FR); Hans-Peter Maerki, Basel (CH); Olivier Morand, Hegenheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 84 days.

(21) Appl. No.: 10/315,770

(22) Filed: Dec. 10, 2002

(65) Prior Publication Data

US 2003/0199550 A1 Oct. 23, 2003

(30) Foreign Application Priority Data

Dec. 12, 2001 (EP) ............................................. 01129271

(51) Int. Cl.[7] ..................... A61K 31/445; C07D 211/06
(52) U.S. Cl. ..................... 514/331; 546/232; 546/197; 548/566; 564/90; 514/428; 514/608
(58) Field of Search ................................ 514/331, 608, 514/428; 546/232, 197; 548/566; 564/90

(56) References Cited

U.S. PATENT DOCUMENTS

| 5,455,273 | A |   | 10/1995 | Maier et al. |   |
|---|---|---|---|---|---|
| 5,495,048 | A |   | 2/1996 | Aebi et al. |   |
| 6,034,275 | A |   | 3/2000 | Aebi et al. |   |
| 6,140,354 | A | * | 10/2000 | Dax et al. ................... | 514/357 |
| 6,211,241 | B1 | * | 4/2001 | Islam et al. ................. | 514/602 |

FOREIGN PATENT DOCUMENTS

| EP | 0 599 203 | 6/1994 |
|---|---|---|
| EP | 0 636 367 | 2/1995 |

OTHER PUBLICATIONS

Gotto et al., Circulation 81, 1990, pp. 1721–1733.
Stein, et al., Nutr. Metab. Cardiovasc. Dis. 2, 1992, pp. 113–156.
Illingworth, Med. Clin. North. Am. 84, 2000, pp. 23–42.
Ross et al., Arch. Intern. Med. 159, 1999, pp. 1793–1802.
Ellen & McPherson, J. Cardiol. 81, 1998, pp. 60B–65B.
Shepherd, Eur. Heart J. 16, 1995, pp. 5–13.
Davignon et al., Can. J. Cardiol. 8, 1992, pp. 843–864.
Pederson & Tobert, Drug Safety 14, 1996, pp. 11–24.
Morand et al., J. Lipid Res., 38, 1997, pp. 373–390.
Mark et al., J. Lipid Res. 37, 1996, pp. 148–158.
Peffley et al., Biochem. Pharmacol. 56, 1998, pp. 439–449.
Nelson et al., J. Biol. Chem. 256, 1981, pp. 1067–1068.
Spencer et al., J. Biol. Chem. 260, 1985, pp. 13391–13394.
Panini et al., J. Lipid Res. 27, 1986, pp. 1190–1204.
Ness et al., Arch. Biochem. Biophys. 308, 1994, pp. 420–425.
Janowski et al., Proc. Natl. Acad. Sci. USA, 96, 1999, pp. 266–271.
Venkateswaran et al., J. Biol. Chem. 275, 2000, pp. 14700–14707.
Schmitz & Kaminsky, Front Biosci 6, 2001, pp. D505–D514.
Ordovas, Nutr Rev 58, 2000, pp. 76–79.
Tobin et al., Mol. Endocrinol. 14, 2000, pp. 741–751.
Costet, P. et al, The Journal of Biological Chemistry, vol. 275, No. 36, Sep. 18, 2000, pp. 28240–28245.
Wang, N. et al., The Journal of Biological Chemistry, vol. 275, No. 42, Oct. 20, 2000, pp. 33053–33058.
H. Rueeger, et al., Bioorganic and Medicinal Chemistry Letters, vol. 10, No. 11, pp. 1175–1179 (2000).

* cited by examiner

Primary Examiner—Charanjit S. Aulakh
(74) Attorney, Agent, or Firm—George W. Johnston; Dennis P. Tramaloni; Samuel H. Megerditchian

(57) ABSTRACT

The present invention provides compounds of formula (I)

wherein $A^1, A^2, A^3, A^4, A^5, A^6, A^7, A^8, A^9, A^{10}$, U, V, W, m, n and p are as indicated in the specification, and pharmaceutically acceptable salts thereof. The compounds are useful for the treatment and/or prophylaxis of diseases which are associated with 2,3-oxidosqualene-lanosterol cyclase such as hypercholesterolemia and hyperlipemia.

28 Claims, No Drawings

SUBSTITUTED CYCLOHEXANE DERIVATIVES

BACKGROUND OF THE INVENTION

The microsomal enzyme, 2,3-oxidosqualene-lanosterol cyclase (EC 5.4.99.), is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that OSC inhibitors could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

SUMMARY OF THE INVENTION

The present invention provides compounds of formula (I)

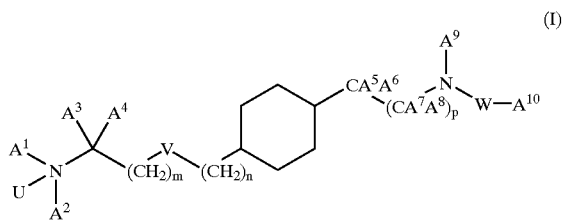

wherein
U is O or a lone pair,
V is a single bond, O, S, —CH$_2$—, —CH═CH—, —CH═CH—CH$_2$—O—, or —C≡C—, W is CO, COO, CONR$^1$, CSO, CSNR$^1$, SO$_2$, or SO$_2$NR$^1$,
m and n independently from each other are from 0 to 7 and m+n is from 0 to 7, with the proviso that m is not 0 if V is O or S, A$^1$ is hydrogen, lower-alkyl, hydroxy-lower-alkyl, or lower-alkenyl, A$^2$ is cycloalkyl, cycloalkyl-lower-alkyl, lower-alkenyl, lower-alkynyl, heteroaryl, substituted heteroaryl, or lower-alkyl optionally substituted by R$^2$, or A$^1$ and A$^2$ are bonded to each other to form a ring with the N atom to which they are attached, and —A$^1$—A$^2$— is lower-alkylene or lower-alkenylene, optionally substituted by R$^2$, in which one —CH$_2$— group of —A$^1$—A$^2$— can optionally be replaced by NR$^3$, S, or O, or —A$^1$—A$^2$— is —CH=N—CH=CH— which can optionally be substituted by lower-alkyl, A$^3$ and A$^4$ independently from each other are hydrogen or lower-alkyl, or A$^3$ and A$^4$ are bonded to each other to form a ring together with the carbon atom to which they are attached and —A$^3$—A$^4$— is —(CH$_2$)$_{2-5}$—, A$^5$, A$^6$, A$^7$ and A$^8$ independently from each other are hydrogen or lower-alkyl, A$^9$ is hydrogen, lower-alkyl, lower-alkenyl, or aryl-lower-alkyl, A$^{10}$ is lower-alkyl, cycloalkyl, aryl, substituted aryl, aryl-lower-alkyl, substituted aryl-lower-alkyl, heteroaryl, substituted heteroaryl, heteroaryl-lower-alkyl, or substituted heteroaryl-lower alkyl, p is 0 or 1, R$^2$ is hydroxy, hydroxy-lower-alkyl, lower-alkoxy, lower-alkoxycarbonyl, N(R$^4$,R$^5$), thio-lower-alkoxy or halogen, R$^1$, R$^3$, R$^4$ and R$^5$ independently from each other are hydrogen or lower-alkyl, substituted aryl and substituted heteroaryl are aryl and heteroaryl, respectively, substituted by 1 to 3 substituents independently selected from the group consisting of lower-alkyl, lower-alkynyl, dioxo-lower-alkylene (forming e.g. a benzodioxyl group), halogen, hydroxy, CN, CF$_3$, NH$_2$, N(H, lower-alkyl), N(lower-alkyl)$_2$, aminocarbonyl, carboxy, NO$_2$, lower-alkoxy, thio-lower-alkoxy, lower-alkylcarbonyl, lower-alkylcarbonyloxy, lower-alkoxycarbonyl, phenyl, and phenyloxy, and pharmaceutically acceptable salts thereof, with the proviso that the compound of formula (I) is not trans-naphthalene-1-sulfonic acid methyl-(4-methylaminomethyl-cyclohexylmethyl)-amide.

The compounds of the present invention are useful for the treatment and/or prophylaxis of diseases associated with 2,3-oxidosqualine-lanosterol cyclase such as hypercholesterolemia and hyperlipemia.

DETAILED DESCRIPTION OF THE INVENTION

The present invention provides compounds of formula (I)

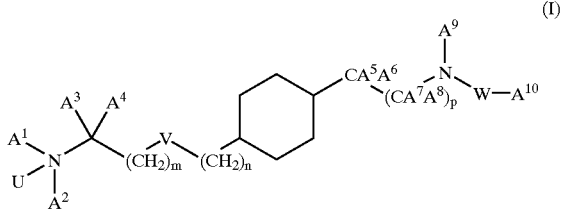

(I)

wherein

U is O or a lone pair,

V is a single bond, O, S, —CH$_2$—, —CH=CH—, —CH=CH—CH$_2$—O—, or —C≡C—,

W is CO, COO, CONR$^1$, CSO, CSNR$^1$, SO$_2$, or SO$_2$NR$^1$, m and n independently from each other are from 0 to 7 and m+n is from 0 to 7, with the proviso that m is not 0 if V is O or S, A$^1$ is hydrogen, lower-alkyl, hydroxy-lower-alkyl, or lower-alkenyl, A$^2$ is cycloalkyl, cycloalkyl-lower-alkyl) lower-alkenyl, lower-alkynyl, heteroaryl, substituted heteroaryl, or lower-alkyl optionally substituted by R$^2$, or A$^1$ and A$^2$ are bonded to each other to form a ring with the N atom to which they are attached, and —A$^1$—A$^2$— is lower-alkylene or lower-alkenylene, optionally substituted by R$^2$, in which one —CH$_2$— group of —A$^1$—A$^2$— can optionally be replaced by NR$^3$, S, or O, or —A$^1$—A$^2$— is —CH=N—CH=CH— which can optionally be substituted by lower-alkyl, A$^3$ and A$^4$ independently from each other are hydrogen or lower-alkyl, or A$^3$ and A$^4$ are bonded to each other to form a ring together with the carbon atom to which they are attached and —A$^3$—A$^4$— is —(CH$_2$)$_{2-5}$—, A$^5$, A$^6$, A$^7$ and A$^8$ independently from each other are hydrogen or lower-alkyl, A$^9$ is hydrogen, lower-alkyl, lower-alkenyl, or aryl-lower-alkyl, A$^{10}$ is lower-alkyl, cycloalkyl, aryl, substituted aryl, aryl-lower-alkyl, substituted aryl-lower-alkyl, heteroaryl, substituted heteroaryl, heteroaryl-lower-alkyl, or substituted heteroaryl-lower alkyl, p is 0 or 1, R$^2$ is hydroxy, hydroxy-lower-alkyl, lower-alkoxy, lower-alkoxycarbonyl, N(R$^4$,R$^5$), thio-lower-alkoxy or halogen, R$^1$, R$^3$, R$^4$ and R$^5$ independently from each other are hydrogen or lower-alkyl, substituted aryl and substituted heteroaryl are aryl and heteroaryl, respectively, substituted by 1 to 3 substituents independently selected from the group consisting of lower-alkyl, lower-alkynyl, dioxo-lower-alkylene (forming e.g. a benzodioxyl group), halogen, hydroxy, CN, CF$_3$, NH$_2$, N(H, lower-alkyl), N(lower-alkyl)$_2$, aminocarbonyl, carboxy, NO$_2$, lower-alkoxy, thio-lower-alkoxy, lower-alkylcarbonyl, lower-alkylcarbonyloxy, lower-alkoxycarbonyl, phenyl, and phenyloxy, and pharmaceutically acceptable salts thereof, with the proviso that the compound of formula (I) is not trans-naphthalene-1-sulfonic acid methyl-(4-methylaminomethyl-cyclohexylmethyl)-amide.

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

Unless otherwise indicated the following definitions are set forth to illustrate and define the meaning and scope of the various terms used to describe the invention herein. In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atom(s), preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl. The term "thioalkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms, more preferably up to 10 carbon atoms. Lower-alkenyl groups as described below also are preferred alkenyl groups. The term "lower-alkenyl" refers to a straight-chain or branched hydrocarbon residue comprising an olefinic bond and up to 7, preferably up to 4 carbon atoms, such as e.g. 2-propenyl.

The term "alkynyl", alone or in combination with other groups, stands for a straight-chain or branched hydrocarbon residue comprising a triple bond and up to 20, preferably up to 16 carbon atoms, more preferably up to 10 carbon atoms. Lower-alkynyl groups as described below also are preferred alkynyl groups. The term "lower-alkynyl" refers to a straight-chain or branched hydrocarbon residue comprising a triple bond and up to 7, preferably up to 4 carbon atoms, such as e.g. 2-propinyl.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "alkenylene" refers to a straight chain or branched divalent hydrocarbon group comprising an olefinic bond and up to 20 carbon atoms, preferably up to 16 carbon atoms, more preferably up to 10 carbon atoms. Lower-alkenylene groups as described below also are preferred alkenylene groups. The term "lower-alkenylene" refers to a straight chain or branched divalent hydrocarbon group comprising an olefinic bond and up to 7, preferably up to 5, C-atoms. Straight chain alkenylene or lower-alkenylene groups are preferred.

The term "aryl" relates to the phenyl or naphthyl group, preferably the phenyl group. "Substituted phenyl" is aryl substituted by 1 to 3 substituents independently selected from the group consisting of lower-alkyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl, phenyl, phenyloxy. Preferred substituents are halogen, $CF_3$, CN, lower-alkyl and/or lower-alkoxy. More preferred substituents are chlorine and $CF_3$.

The term "heteroaryl" refers to an aromatic 5- or 6-membered ring which can comprise 1, 2 or 3 atoms selected from nitrogen, oxygen and/or sulphur, such as, for example, furyl, pyridyl, pyridazinyl, pyrimidinyl, pyrazinyl, thienyl, isoxazolyl, oxazolyl, imidazolyl, or pyrrolyl. "Substituted heteroaryl" is heteroaryl which is substituted by 1 to 3 substituents independently selected from the group consisting of lower-alkyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl, phenyl, phenyloxy. Preferred substituents are halogen, $CF_3$, CN, lower-alkyl and/or lower-alkoxy. More preferred substituents are chlorine and $CF_3$. A preferred heteroaryl group is pyrimidinyl; a preferred substituted heteroaryl is heteroaryl substituted with methyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are formates, hydrochlorides, hydrobromides and methanesulfonic acid salts.

Preferred are compounds of formula (I) and/or pharmaceutically acceptable salts thereof. Other preferred embodiments relate to compounds of formula (I) wherein U is a lone pair or to compounds of formula (I) wherein U is O.

Compounds of formula (I) as described above, in which V is a single bond, O, —$CH_2$—, —CH=CH—, —CH=CH—$CH_2$—O—, or —C≡C— relate to a preferred embodiment of the present invention. More preferred compounds as defined above are those, wherein V is a single bond. Other more preferred compounds as defined above are those, wherein V is —$CH_2$—. Other more preferred compounds as defined above are those, wherein V is —CH=CH—. Other more preferred compounds as defined above are those, wherein V is —C≡—C—. In addition, compounds of formula (I) as defined above, in which W is COO relate to a preferred embodiment of the present invention. Compounds in which W is $SO_2$ are also preferred.

In a further preferred embodiment of the present invention, m is 0 to 4 and n is 0 to 1. Compounds of formula (I), in which m is 0 and/or n is 0 are also preferred. Compounds as described above, in which the number of carbon atoms of $(CH_2)_m$, V and $(CH_2)_n$ together is 7 or less, are also preferred.

Other preferred compounds of the present invention are those in which $A^1$ represents hydrogen, lower-alkyl or hydroxy-lower-alkyl, preferably those in which $A^1$ is methyl, ethyl or 2-hydroxy-ethyl. Another group of preferred compounds of the present invention are those in which $A^2$ represents lower-alkenyl, 2-methyl-pyrimidinyl, or lower-alkyl optionally substituted by $R^2$, wherein $R^2$ is hydroxy, with those compounds wherein $A^2$ represents methyl or 2-hydroxy-ethyl being especially preferred.

Compounds of formula (I), wherein $A^1$ and $A^2$ are bonded to each other to form a ring and —$A^1$—$A^2$— is lower-alkylene optionally substituted by $R^2$, in which one —$CH_2$— group of —$A^1$—$A^2$— can optionally be replaced by $NR^3$ or O, or —$A^1$—$A^2$— is —CH=N—CH=CH—, wherein $R^2$ is hydroxy or hydroxy-lower-alkyl, and $R^3$ is hydrogen or lower-alkyl are also preferred, with those compounds, wherein —$A^1$—$A^2$— is —$(CH_2)_4$— or —$(CH_2)_5$— being especially preferred. In compounds wherein $A^1$ and $A^2$ are bonded to each other to form a ring, said ring is preferably a 4-, 5-, or 6-membered ring such as e.g. piperidinyl or pyrrolidinyl.

A further preferred embodiment of the present invention relates to compounds of formula (I), wherein $A^3$ and $A^4$ represent hydrogen. Other preferred compounds of formula (I) as defined above are those wherein $A^5$ and $A^6$ represent hydrogen. Other preferred compounds of formula (I) as defined above are those wherein $A^7$ and $A^8$ represent hydrogen.

Compounds of formula (I), wherein $A^9$ is lower-alkyl also relate to a preferred embodiment of the present invention, with those compounds, wherein $A^9$ is methyl relating to a particularly preferred embodiment. Other preferred compounds are those in which $A^{10}$ is aryl, more preferably wherein $A^{10}$ is phenyl optionally substituted with halogen or $CF_3$. Compounds of formula (I) as defined above, wherein $A^{10}$ is 4-chloro-phenyl or 4-trifluoromethyl-phenyl are most preferred.

Preferred compounds of general formula (I) are those selected from the group consisting of trans-N-{4-[5-(Allyl-methyl-amino)-pentyl]-cyclohexylmethyl}-N-methyl-4-trifluoromethyl-benzenesulfonamide, trans-N-{4-[5-(4-Hydroxy-piperidin-1-yl)-pentyl]-cyclohexylmethyl}-N-methyl-4-trifluoromethyl-benzenesulfonamide, trans-N-[4-(5-Dimethylamino-pentyl)-cyclohexylmethyl]-N-methyl-4-trifluoromethyl-benzenesulfonamide, trans-N-(4-{5-[Ethyl-(2-hydroxy-ethyl)-amino]-pentyl}-cyclohexylmethyl)-N-methyl-4-trifluoromethyl-benzenesulfonamide, trans-N-(4-{5-[Bis-(2-hydroxy-ethyl)-amino]-pentyl}-cyclohexylmethyl)-N-methyl-4-trifluoromethyl-benzenesulfonamide, trans-{4-[5-(Allyl-methyl-amino)-pentyl]-cyclohexylmethyl}-methyl-carbamic acid 4-trifluoromethyl-phenyl ester, trans-[4-(5-Dimethylamino-pentyl)-cyclohexylmethyl]-methyl-carbamic acid 4-trifluoromethyl-phenyl ester, trans-(4-{5-[Ethyl-(2-hydroxy-ethyl)-amino]-pentyl}-cyclohexylmethyl)-methyl-carbamic acid 4-trifluoromethyl-phenyl ester, trans-{4-[5-(4-Hydroxy-piperidin-1-yl)-pentyl]-cyclohexylmethyl}-methyl-carbamic acid 4-trifluoromethyl-phenyl ester, trans-(4-{5-[Bis-(2-hydroxy-ethyl)-amino]-pentyl}-cyclohexylmethyl)-methyl-carbamic acid 4-trifluoromethyl-phenyl ester, trans-N-Methyl-N-[4-(5-piperidin-1-yl-pentyl)-cyclohexylmethyl]-4-trifluoromethyl-benzenesulfonamide, trans-N-Methyl-N-[4-(5-pyrrolidin-1-yl-pentyl)-cyclohexylmethyl]-4-trifluoromethyl-benzenesulfonamide, trans-N-(4-{4-[Ethyl-(2-hydroxy-ethyl)-amino]-butyl}-cyclohexylmethyl)-N-methyl-4-trifluoromethyl-benzenesulfonamide, trans-N-[4-(4-Dimethylamino-butyl)-cyclohexylmethyl]-N-methyl-4-trifluoromethyl-benzenesulfonamide, trans-N-[4-(4-Diethylamino-butyl)-cyclohexylmethyl]-N-methyl-4-trifluoromethyl-benzenesulfonamide, trans-N-{4-[4-(Allyl-methyl-amino)-butyl]-cyclohexylmethyl}-N-methyl-4-trifluoromethyl-benzenesulfonamide, trans-N-(4-{4-[Bis-(2-hydroxy-ethyl)-amino]-butyl}-cyclohexylmethyl)-N-methyl-4-trifluoromethyl-benzenesulfonamide, trans-{4-[4-(Allyl-methyl-amino)-butyl]-cyclohexylmethyl}-methyl-carbamic acid 4-chloro-phenyl ester, trans-Methyl-[4-(4-piperidin-1-yl-butyl)-cyclohexylmethyl]-carbamic acid 4-chloro-phenyl ester, trans-(4-{4-[Ethyl-(2-hydroxy-ethyl)-amino]-butyl}-cyclohexylmethyl)-methyl-carbamic acid 4-chloro-phenyl ester, trans-N-(4-Dimethylaminomethyl-cyclohexylmethyl)-N-methyl-4-trifluoromethyl-benzenesulfonamide, trans-N-{4-[(Allyl-methyl-amino)-methyl]-cyclohexylmethyl}-N-methyl-4-trifluoromethyl-benzenesulfonamide, trans-N-(4-{[Ethyl-(2-hydroxy-ethyl)-amino]-methyl}-cyclohexylmethyl)-N-methyl-4-trifluoromethyl-benzenesulfonamide, trans-N-(4-Diethylaminomethyl-cyclohexylmethyl)-N-methyl-4-trifluoromethyl-benzene-sulfonamide, trans-N-(4-{[Bis-(2-hydroxy-ethyl)-amino]-methyl}-cyclohexylmethyl)-N-methyl-4-trifluoromethyl-benzenesulfonamide, trans-(4-Dimethylaminomethyl-cyclohexylmethyl)-methyl-carbamic acid 4-chloro-phenyl ester, trans-{4-[(Allyl-methyl-amino)-methyl]-cyclohexylmethyl}-methyl-carbamic acid 4-chloro-phenyl ester, trans-(4-Diethylaminomethyl-cyclohexylmethyl)-methyl-carbamic acid 4-chloro-phenyl ester, trans-(4-{[Ethyl-(2-hydroxy-ethyl)-amino]-methyl}-cyclohexylmethyl)-methyl-carbamic acid 4-chloro-phenyl ester, trans-(4-{[Bis-(2-hydroxy-ethyl)-amino]-methyl}-cyclohexylmethyl)-methyl-carbamic acid 4-chloro-phenyl ester, trans-N-(4-Ethylaminomethyl-cyclohexylmethyl)-N-methyl-4-trifluoromethyl-benzenesulfonamide, trans-N-Methyl-N-(4-piperidin-1-ylmethyl-cyclohexylmethyl)-4-trifluoromethyl-benzenesulfonamide, trans-N-(4-Azetidin-1-ylmethyl-cyclohexylmethyl)-N-methyl-4-trifluoromethyl-benzenesulfonamide, trans-N-Methyl-N-(4-pyrrolidin-1-ylmethyl-cyclohexylmethyl)-4-trifluoromethyl-benzenesulfonamide, trans-Methyl-(4-piperidin-1-ylmethyl-cyclohexylmethyl)-carbamic acid 4-chloro-phenyl ester, trans-Methyl-(4-pyrrolidin-1-ylmethyl-cyclohexylmethyl)-carbamic acid 4-chloro-phenyl ester trans-N-{4-[3-(Allyl-methyl-amino)-propyl]-cyclohexylmethyl}-N-methyl-4-trifluoromethyl-benzenesulfonamide, trans-N-(4-{3-[Ethyl-(2-hydroxy-ethyl)-amino]-propyl}-cyclohexylmethyl)-N-methyl-4-trifluoromethyl-benzenesulfonamide, trans-N-[4-(3-Allylamino-propyl)-cyclohexylmethyl]-N-methyl-4-trifluoromethyl-benzenesulfonamide, trans-N-Methyl-N-[4-(3-methylamino-propyl)-cyclohexylmethyl]-4-trifluoromethyl-benzenesulfonamide, trans-{4-[3-(Allyl-methylamino)-propyl]-cyclohexylmethyl}-methyl-carbamic acid 4-chloro-phenyl ester, trans-Methyl-[4-(3-piperidin-1-yl-propyl)-cyclohexylmethyl]-carbamic acid 4-chloro-phenyl ester, trans-(4-{3-[Ethyl-(2-hydroxy-ethyl)-amino]-propyl}-cyclohexylmethyl)-methyl-carbamic acid 4-chloro-phenyl ester, trans-(4-{3-[Bis-(2-hydroxy-ethyl)-amino]-propyl}-cyclohexylmethyl)-methyl-carbamic acid 4-chloro-phenyl ester, trans-{4-[2-(Allyl-methylamino)-ethyl]-cyclohexylmethyl}-methyl-carbamic acid 4-chloro-phenyl ester, trans-Methyl-[4-(2-piperidin-1-yl-ethyl)-cyclohexylmethyl]-carbamic acid 4-chloro-phenyl ester, trans-N-Methyl-N-[4-(2-piperidin-1-yl-ethyl)-cyclohexylmethyl]-4-trifluoromethyl-benzenesulfonamide, trans-N-(4-{2-[Ethyl-(2-hydroxy-ethyl)-amino]-ethyl}-cyclohexylmethyl)-N-methyl-4-trifluoromethyl-benzenesulfonamide, trans-N-(4-{2-[Bis-(2-hydroxy-ethyl)-amino]-ethyl}-cyclohexylmethyl)-N-methyl-4-trifluoromethyl-benzenesulfonamide, trans-(4-{2-[Ethyl-(2- hydroxy-ethyl)-amino]-ethyl}-cyclohexyl-methyl)-methylcarbamic acid 4-chloro-phenyl ester, trans-N-{4-[2-(Allyl-methylamino)-ethyl]-cyclohexylmethyl}-N-methyl-4-trifluoromethyl-benzenesulfonamide, trans-(RS,RS)-N-(4-{2-[Bis-(2-hydroxy-propyl)-amino]-ethyl}-cyclohexylmethyl)-N-methyl-4-trifluoromethyl-benzenesulfonamide, trans-(2-{4-[3-(Allyl-methyl-amino)-propyl]-cyclohexyl}-ethyl)-methyl-carbamic acid 4-trifluoromethyl-phenyl ester, trans-[2-(4-{3-[Ethyl-(2-hydroxy-ethyl)-amino]-propyl}-cyclohexyl)-ethyl]-methyl-carbamic acid 4-trifluoromethyl-phenyl ester, trans-Methyl-{2-[4-(3-morpholin-4-yl-propyl)-cyclohexyl]-ethyl}-carbamic acid 4-trifluoromethyl-phenyl ester, trans-Methyl-{2-[4-(3-piperidin-1-yl-propyl)-cyclohexyl]-ethyl}-carbamic acid 4-trifluoromethyl-phenyl ester, trans-{2-[4-(3-Dimethylamino-propyl)-cyclohexyl]-ethyl}-methyl-carbamic acid 4-trifluoromethyl-phenyl ester, trans-{2-[4-(3-Diethylamino-propyl)-cyclohexyl]-ethyl}-methyl-carbamic acid 4-trifluoromethyl-phenyl ester, trans-Methyl-(2-{4-[3-(methyl-propyl-amino)-propyl]-cyclohexyl}-ethyl)-carbamic acid 4-trifluoromethyl-phenyl ester, trans-[2-(4-{3-[Bis-(2-hydroxy-ethyl)-amino]-propyl}-cyclohexyl)-ethyl]-methyl-carbamic acid 4-trifluoromethyl-phenyl ester, trans-Methyl-(2-{4-[3-(4-methyl-piperazin-1-yl)-propyl]-cyclohexyl}-ethyl)-carbamic acid 4-trifluoromethyl-phenyl ester, trans-N-(2-{4-[(Allyl-methyl-amino)-methyl]-cyclohexyl}-ethyl)-N-methyl-4-trifluoromethyl-benzenesulfonamide, trans-(2-{4-[(Allyl-methyl-amino)-methyl]-cyclohexyl}-ethyl)-methyl-carbamic acid 4-trifluoromethyl-phenyl ester, trans-[2-(4-Dimethylaminomethyl-cyclohexyl)-ethyl]-methyl-carbamic acid 4-trifluoromethyl-phenyl ester, trans-[2-(4-{[Ethyl-(2-hydroxy-ethyl)-amino]-methyl}-cyclohexyl)-ethyl]-methyl-carbamic acid 4-trifluoromethyl-phenyl ester, trans-Methyl-{2-[4-(4-methyl-piperazin-1-ylmethyl)-cyclohexyl]-ethyl}-carbamic acid 4-trifluoromethyl-phenyl ester, trans-(2-{4-[(2-Hydroxy-ethylamino)-methyl]-cyclohexyl}-ethyl)-methyl-carbamic acid 4-trifluoromethyl-phenyl ester, trans-(2-{4-[(2-Hydroxy-1,1-dimethyl-ethylamino)-methyl]-cyclohexyl}-ethyl)-methyl-carbamic acid 4-trifluoromethyl-phenyl ester, trans-[2-(4-Allylaminomethyl-cyclohexyl)-ethyl]-methyl-carbamic acid 4-trifluoromethyl-phenyl ester, trans-Methyl-[2-(4-methylaminomethyl-cyclohexyl)-ethyl]-carbamic acid 4-trifluoromethyl-phenyl ester, trans-N-[2-(4-Dimethylaminomethyl-cyclohexyl)-ethyl]-N-methyl-4-trifluoromethyl-benzenesulfonamide, trans-N-[2-(4-{[Ethyl-(2-hydroxy-ethyl)-amino]-methyl }-cyclohexyl)-ethyl]-N-methyl-4-trifluoromethyl-benzenesulfonamide, trans-N-Methyl-N-{2-[4-(4-methyl-piperazin-1-ylmethyl)-cyclohexyl]-ethyl}-4-trifluoromethyl-benzenesulfonamide, trans-N-(2-{4-[(2-Hydroxy-ethylamino)-methyl]-cyclohexyl}-ethyl)-N-methyl-4-trifluoromethyl-benzenesulfonamide, trans-N-Methyl-N-[2-(4-methylaminomethyl-cyclohexyl)-ethyl]-4-trifluoromethyl-benzenesulfonamide, trans-N-(2-{4-[(2-Hydroxy-1,1-dimethyl-ethylamino)-methyl]-cyclohexyl}-ethyl)-N-methyl-4-trifluoromethyl-benzenesulfonamide, trans-N-[2-(4-Allylaminomethyl-cyclohexyl)-ethyl]-N-methyl-4-trifluoromethyl-benzenesulfonamide, trans-N-Methyl-N-[2-(4-piperidin-1-ylmethyl-cyclohexyl)-ethyl]-4-trifluoromethyl-benzenesulfonamide, trans-Methyl-[2-(4-piperidin-1-ylmethyl-cyclohexyl)-ethyl]-carbamic acid 4-trifluoromethyl-phenyl ester, trans-Methyl-[2-(4-piperidin-1-ylmethyl-cyclohexyl)-ethyl]-carbamic acid 4-chloro-phenyl ester, trans-[2-(4-{[Ethyl-(2-hydroxy-ethyl)-amino]-methyl}-cyclohexyl)-ethyl]-methyl-carbamic acid 4-chloro-phenyl ester, trans-[2-(4-Ethylaminomethyl-cyclohexyl)-ethyl]-methyl-carbamic acid 4-chloro-phenyl ester, trans-[2-(4-Dimethylaminomethyl-cyclohexyl)-ethyl]-methyl-carbamic acid 4-chloro-phenyl ester, trans-(2-{4-[(Allyl-methyl-amino)-methyl]-cyclohexyl}-ethyl)-methyl-carbamic acid 4-chloro-phenyl ester, trans-Methyl-[2-(4-pyrrolidin-1-ylmethyl-cyclohexyl)-ethyl]-carbamic acid 4-chloro-phenyl ester, trans-Methyl-[2-(4-methylaminomethyl-cyclohexyl)-ethyl]-carbamic acid 4-chloro-phenyl ester, trans-4-Chloro-N-methyl-N-[2-(4-piperidin-1-ylmethyl-cyclohexyl)-ethyl]-benzenesulfonamide, trans-4-Chloro-N-[2-(4-dimethylaminomethyl-cyclohexyl)-ethyl]-N-methyl-benzenesulfonamide, trans-4-Chloro-N-methyl-N-[2-(4-pyrrolidin-1-ylmethyl-cyclohexyl)-ethyl]-benzenesulfonamide, trans-N-(2-{4-[(Allyl-methyl-amino)-methyl]-cyclohexyl}-ethyl)-4-chloro-N-methyl-benzenesulfonamide, trans-4-Chloro-N-methyl-N-[2-(4-methylaminomethyl-cyclohexyl)-ethyl]-benzenesulfonamide, trans-4-Chloro-N-[2-(4-{[ethyl-(2-hydroxy-ethyl)-amino]-methyl}-cyclohexyl)-ethyl]-N-methyl-benzenesulfonamide, trans-4-Chloro-N-[2-(4-ethylaminomethyl-cyclohexyl)-ethyl]-N-methyl-benzenesulfonamide, trans-(2-{4-[(6-Hydroxy-hexylamino)-methyl]-cyclohexyl}-ethyl)-methyl-carbamic acid 4-chloro-phenyl ester, trans-(2-{4-[(5-Hydroxy-pentylamino)-methyl]-cyclohexyl}-ethyl)-methyl-carbamic acid 4-chloro-phenyl ester, trans-4-Chloro-N-(2-{4-[(5-hydroxy-pentylamino)-methyl]-cyclohexyl}-ethyl)-N-methyl-benzenesulfonamide, trans-4-Chloro-N-(2-{4-[(6-hydroxy-hexylamino)-methyl]-cyclohexyl}-ethyl)-N-methyl-benzenesulfonamide, trans-[2-(4-{[Ethyl-(2-hydroxy-ethyl)-amino]-methyl}-cyclohexyl)-ethyl]-methyl-carbamic acid 4-trifluoromethyl-phenyl ester, trans-N-{4-[4-(Allyl-methyl-amino)-butoxy]-cyclohexylmethyl}-4-chloro-N-methyl-benzenesulfonamide, cis-N-{4-[4-(Allyl-methyl-amino)-butoxy]-cyclohexylmethyl}-4-chloro-N-methyl-benzenesulfonamide, trans-{4-[4-(Allyl-methyl-amino)-butoxy]-cyclohexylmethyl}-methyl-carbamic acid 4-chloro-phenyl ester, trans-N-{4-[4-(Allyl-methyl-amino)-butoxy]-cyclohexylmethyl}-N-methyl-4-trifluoromethyl-benzenesulfonamide, trans-N-(4-{4-[Ethyl-(2-hydroxy-ethyl)-amino]-butoxy}-cyclohexylmethyl)-N-methyl-4-trifluoromethyl-benzenesulfonamide, trans-Methyl-{2-[4-(3-piperidin-1-yl-(E)-propenyl)-cyclohexyl]-ethyl}-carbamic acid 4-chloro-phenyl ester, trans-N-Methyl-N-[4-(3-piperidin-1-yl-(E,Z)-propenyl)-cyclohexylmethyl]-4-trifluoromethyl-benzenesulfonamide, trans-N-(4-{3-[Ethyl-(2-hydroxy-ethyl)-amino]-(E,Z)-propenyl}-cyclohexylmethyl)-N-methyl-4-trifluoromethyl-benzenesulfonamide, trans-N-(2-{4-[3-(Allyl-methyl-amino)-(E)-propenyl]-cyclohexyl}-ethyl)-N-methyl-4-trifluoromethyl-benzenesulfonamide, trans-N-{2-[4-(3-Dimethylamino-(E)-propenyl)-cyclohexyl]-ethyl}-N-methyl-4-trifluoromethyl-benzenesulfonamide, trans-N-Methyl-N-{2-[4-(3-piperidin-1-yl-(E)-propenyl)-cyclohexyl]-ethyl}-4-trifluoromethyl-benzenesulfonamide, trans-N-{2-[4-(3-Ethylamino-(E)-propenyl)-cyclohexyl]-ethyl}-N-methyl-4-trifluoromethyl-benzenesulfonamide, trans-(2-{4-[3-(Allyl-methyl-amino)-(E)-propenyl]-cyclohexyl}-ethyl)-methyl-carbamic acid 4-chloro-phenyl ester, trans-{2-[4-(3-Dimethylamino-(E)-propenyl)-cyclohexyl]-ethyl}-methyl-carbamic acid 4-chloro-phenyl ester, trans-{2-[4-(3-Ethylamino-(E)-propenyl)-cyclohexyl]-ethyl}-methyl-carbamic acid 4-chloro-phenyl ester, trans-Methyl-{2-[4-(3-pyrrolidin-1-yl-(E)-propenyl)-cyclohexyl]-ethyl}-carbamic acid 4-chloro-phenyl ester, trans-N-Methyl-N-[4-(4-piperidin-1-yl-(E)-but-2- enyloxymethyl)-cyclohexylmethyl]-4-trifluoromethyl-benzenesulfonamide, trans-N-Methyl-N-[4-(4-pyrrolidin-1-yl-(E)-but-2-enyloxymethyl)-cyclohexylmethyl]-4-trifluoromethyl-benzenesulfonamide, trans-N-(4-{4-[Ethyl-(2-hydroxy-ethyl)-amino]-(E)-but-2-enyloxymethyl}-cyclohexylmethyl)-N-methyl-4-trifluoromethyl-benzenesulfonamide, trans-N-{4-[4-(Allyl-methyl-amino)-(E)-but-2-enyloxymethyl]-cyclohexylmethyl}-N-methyl-4-trifluoromethyl-benzenesulfonamide, trans-N-(4-{4-[Bis-(2-hydroxy-ethyl)-amino]-(E)-but-2-enyloxymethyl}-cyclohexylmethyl)-N-methyl-4-trifluoromethyl-benzenesulfonamide, trans-N-Methyl-N-[4-(4-methylamino-(E)-but-2-enyloxymethyl)-cyclohexylmethyl]-4-trifluoromethyl-benzenesulfonamide, trans-N-(4-{4-[(2-Hydroxy-ethyl)-methyl-amino]-(E)-but-2-enyloxymethyl}-cyclohexylmethyl)-N-methyl-4-trifluoromethyl-benzenesulfonamide, trans-N-Methyl-N-[4-(4-morpholin-4-yl-(E)-but-2-enyloxymethyl)-cyclohexylmethyl]-4-trifluoromethyl-benzenesulfonamide, trans-N-Methyl-N-[4-(4-piperazin-1-yl-(E)-but-2-enyloxymethyl)-cyclohexylmethyl]-4-trifluoromethyl-benzenesulfonamide, trans-N-Methyl-N-[4-(4-piperidin-1-yl-butoxymethyl)-cyclohexylmethyl]-4-trifluoromethyl-benzenesulfonamide, trans-N-(4-{4-[(2-Hydroxy-ethyl)-methyl-amino]-butoxymethyl}-cyclohexylmethyl)-N-methyl-4-trifluoromethyl-benzenesulfonamide, trans-N-Methyl-N-[4-(4-pyrrolidin-1-yl-butoxymethyl)-cyclohexylmethyl]-4-trifluoromethyl-benzenesulfonamide, trans-N-{4-[4-(Allyl-methyl-amino)-butoxymethyl]-cyclohexylmethyl}-N-methyl-4-trifluoromethyl-benzenesulfonamide, trans-N-(4-{4-[Ethyl-(2-hydroxy-ethyl)-amino]-butoxymethyl}-cyclohexylmethyl)-N-methyl-4-trifluoromethyl-benzenesulfonamide, trans-N-[4-(4-Dimethylamino-butoxymethyl)-cyclohexylmethyl]-N-methyl-4-trifluoromethyl-benzenesulfonamide, trans-N-(4-{4-[Bis-(2-hydroxy-ethyl)-amino]-butoxymethyl}-cyclohexylmethyl)-N-methyl-4-trifluoromethyl-benzenesulfonamide, trans-N-{4-[4-((S)-2-Hydroxymethyl-pyrrolidin-1-yl)-butoxymethyl]-cyclohexylmethyl}-N-methyl-4-trifluoromethyl-benzenesulfonamide, trans-Methyl-[4-(4-pyrrolidin-1-yl-butoxymethyl)-cyclohexylmethyl]-carbamic acid 4-chloro-phenyl ester, trans-Methyl-[4-(4-piperidin-1-yl-butoxymethyl)-cyclohexylmethyl]-carbamic acid 4-chloro-phenyl ester, trans-(4-{4-[(2-Hydroxy-ethyl)-methyl-amino]-butoxymethyl}-cyclohexylmethyl)-methyl-carbamic acid 4-chloro-phenyl ester, trans-(4-{4-[Bis-(2-hydroxy-ethyl)-amino]-butoxymethyl}-cyclohexylmethyl)-methyl-carbamic acid 4-chloro-phenyl ester, trans-[4-(4-Dimethylamino-butoxymethyl)-cyclohexylmethyl]-methyl-carbamic acid 4-chloro-phenyl ester, trans-(4-{4-[Ethyl-(2-hydroxy-ethyl)-amino]-butoxymethyl}-cyclohexylmethyl)-methyl-carbamic acid 4-chloro-phenyl ester, trans-Methyl-{2-[4-(2-piperidin-1-yl-ethyl)-cyclohexyl]-ethyl}-carbamic acid 4-chloro-phenyl ester, trans-4-Chloro-N-methyl-N-{2-[4-(2-piperidin-1-yl-ethyl)-cyclohexyl]-ethyl}-benzenesulfonamide, trans-(2-{4-[2-(Allyl-methyl-amino)-ethyl]-cyclohexyl}-ethyl)-methyl-carbamic acid 4-chloro-phenyl ester, trans-{2-[4-(2-Dimethylamino-ethyl)-cyclohexyl]-ethyl}-methyl-carbamic acid 4-chloro-phenyl ester, trans-{2-[4-(2-Ethylamino-ethyl)-cyclohexyl]-ethyl}-methyl-carbamic acid 4-chloro-phenyl ester, trans-[2-(4-{2-[Ethyl-(2-hydroxy-ethyl)-amino]-ethyl}-cyclohexyl)-ethyl]-methyl-carbamic acid 4-chloro-phenyl ester, trans-Methyl-{2-[4-(2-methylamino-ethyl)-cyclohexyl]-ethyl}-carbamic acid 4-chloro-phenyl ester, trans-(2-{4-[2-(6-Hydroxy-hexylamino)-ethyl]-cyclohexyl}-ethyl)-methyl-carbamic acid 4-chloro-phenyl ester, trans-(2-{4-[2-(5-Hydroxy-pentylamino)-ethyl]-cyclohexyl}-ethyl)-methyl-carbamic acid 4-chloro-phenyl ester, trans-4-Chloro-N-{2-[4-(2-dimethylamino-ethyl)-cyclohexyl]-ethyl}-N-methyl-benzenesulfonamide, trans-N-(2-{4-[2-(Allyl-methyl-amino)-ethyl]-cyclohexyl}-ethyl)-4-chloro-N-methyl-benzenesulfonamide, trans-4-Chloro-N-methyl-N-{2-[4-(2-methylamino-ethyl)-cyclohexyl]-ethyl}-benzenesulfonamide, trans-4-Chloro-N-{2-[4-(2-ethylamino-ethyl)-cyclohexyl]-ethyl}-N-methyl-benzenesulfonamide, trans-4-Chloro-N-[2-(4-{2-[ethyl-(2-hydroxy-ethyl)-amino]-ethyl}-cyclohexyl)-ethyl]-N-methyl-benzenesulfonamide, trans-Methyl-[4-(3-piperidin-1-yl-prop-1-ynyl)-cyclohexylmethyl]-carbamic acid 4-chloro-phenyl ester, trans-(4-{3-[Ethyl-(2-hydroxy-ethyl)-amino]-prop-1-ynyl}-cyclohexylmethyl)-methyl-carbamic acid 4-chloro-phenyl ester, trans-N-Methyl-N-[4-(3-piperidin-1-yl-prop-1-ynyl)-cyclohexylmethyl]-4-trifluoromethyl-benzenesulfonamide, trans-N-(4-{3-[Ethyl-(2-hydroxy-ethyl)-amino]-prop-1-ynyl}-cyclohexylmethyl)-N-methyl-4-trifluoromethyl-benzenesulfonamide, trans-Methyl-[4-(3-piperidin-1-yl-prop-1-ynyl)-cyclohexylmethyl]-carbamic acid 4-trifluoromethyl-phenyl ester, trans-(4-{3-[Ethyl-(2-hydroxy-ethyl)-amino]-prop-1-ynyl}-cyclohexylmethyl)-methyl-carbamic acid 4-trifluoromethyl-phenyl ester, trans-{2-[4-(3-Imidazol-1-yl-propyl)-cyclohexyl]-ethyl}-methyl-carbamic acid 4-chloro-phenyl ester, trans-N-[2-(4-Imidazol-1-ylmethyl-cyclohexyl)-ethyl]-N-methyl-4-trifluoromethyl-benzenesulfonamide, trans-N-(4-Imidazol-1-ylmethyl-cyclohexylmethyl)-N-methyl-4-trifluoromethyl-benzenesulfonamide, trans-N-[4-(3-Imidazol-1-yl-(E,Z)-propenyl)-cyclohexylmethyl]-N-methyl-4-trifluoromethyl-benzenesulfonamide, trans-N-[4-(2-Imidazol-1-yl-ethyl)-cyclohexylmethyl]-N-methyl-4-trifluoromethyl-benzenesulfonamide, trans-N-[4-(4-Imidazol-1-yl-(E)-but-2-enyloxymethyl)-cyclohexylmethyl]-N-methyl-4-trifluoromethyl-benzenesulfonamide, trans-N-Methyl-N-(4-{4-[methyl-(2-methyl-pyrimidin-4-yl)-amino]-(E)-but-2-enyloxymethyl}-cyclohexylmethyl)-4-trifluoromethyl-benzenesulfonamide, rac-trans-ethyl(2-hydroxyethyl)({4-[2-(methyl{[4-(trifluoromethyl)phenoxy]carbonyl}amino)-ethyl]cyclohexyl}methyl)ammoniumolate, trans-Methyl-{4-[3-(methyl-propyl-amino)-prop-1-ynyl]-cyclohexylmethyl}-carbamic acid 4-fluoro-phenyl ester, trans-(4-{3-[Ethyl-(2-hydroxy-ethyl)-amino]-prop-1-ynyl}-cyclohexylmethyl)-methyl-carbamic acid 4-fluoro-phenyl ester, and trans-[4-(3-Dimethylamino-prop-1-ynyl)-cyclohexylmethyl]-methyl-carbamic acid 4-fluoro-phenyl ester, and pharmaceutically acceptable salts thereof.

Particularly preferred compounds of general formula (I) are those selected from the group consisting of trans-Methyl-[4-(2-piperidin-1-yl-ethyl)-cyclohexylmethyl]-carbamic acid 4-chloro-phenyl ester, trans-N-Methyl-N-[4-(2-piperidin-1-yl-ethyl)-cyclohexylmethyl]-4-trifluoromethyl-benzenesulfonamide, trans-N-(4-{2-[Bis-(2-hydroxy-ethyl)-amino]-ethyl}-cyclohexylmethyl)-N-methyl-4-trifluoromethyl-benzenesulfonamide, trans-[2-(4-Dimethylaminomethyl-cyclohexyl)-ethyl]-methyl-carbamic acid 4-trifluoromethyl-phenyl ester, trans-[2-(4-{[Ethyl-(2-hydroxy-ethyl)-amino]-methyl}-cyclohexyl)-ethyl]-methyl-carbamic acid 4-trifluoromethyl-phenyl ester, trans-Methyl-[2-(4-piperidin-1-ylmethyl-cyclohexyl)-ethyl]-carbamic acid 4-trifluoromethyl-phenyl ester, trans-Methyl-{2-[4-(3-piperidin-1-yl-(E)-propenyl)-cyclohexyl]-ethyl}-carbamic acid 4-chloro-phenyl ester, trans-Methyl-{2-[4-(3-pyrrolidin-1-yl-(E)-propenyl)-cyclohexyl]-ethyl}-carbamic acid 4-chloro-phenyl ester, trans-(4-{5-[Bis-(2-hydroxy-ethyl)-amino]-pentyl}-cyclohexylmethyl)-methyl-carbamic acid 4-trifluoromethyl-phenyl ester, trans-(4-{3-[Ethyl-(2-hydroxy-ethyl)-amino]-prop-1-ynyl}-cyclohexylmethyl)-methyl-carbamic acid 4-trifluoromethyl-phenyl ester, and trans-N-(4-{3-[Ethyl-(2-hydroxy-ethyl)-amino]-propyl}-cyclohexylmethyl)-N-methyl-4-trifluoromethyl-benzenesulfonamide, and pharmaceutically acceptable salts thereof.

Preferred compounds of formula (I) include:

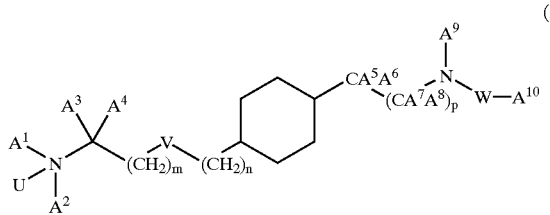

(I)

wherein

U is a lone pair,
V is —CH$_2$—, —CH=CH—, or —C≡C—,
W is COO or SO$_2$,
m and n independently from each other are from 0 to 3 and m+n is from 0 to 3,
A$^1$ is hydroxy lower-alkyl, or lower-alkyl,
A$^2$ is hydroxy lower-alkyl or lower-alkyl, or
A$^1$ and A$^2$ are bonded to each other to form a ring with the N atom to which they are attached, and —A$^1$—A$^2$— is lower-alkylene,
A$^3$ and A$^4$ are each hydrogen,
A$^5$, A$^6$, A$^7$ and A$^8$ are each hydrogen,
A$^9$ is lower-alkyl,
A$^{10}$ is phenyl substituted with chlorine or —CF$_3$,
p is 0 or 1,
and pharmaceutically acceptable salts thereof.

Compounds of formula (I) can have one or more asymmetric carbon atoms and can exist in the form of optically pure enantiomers or as racemates. The invention embraces all of these forms. Compounds of formula (I) which are trans-isomers (with reference to the cyclohexyl ring) are preferred.

It will be appreciated that the compounds of general formula (I) in this invention may be derivatised at functional groups to provide derivatives which are capable of conversion back to the parent compound in vivo.

The present invention also relates to a process for the manufacture of compounds of formula (I) as described above, which process comprises a) reacting a compound of formula (II)

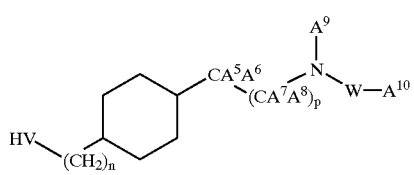

(II)

with a compound (A$^1$,A$^2$,U)N—C(A$^3$,A$^4$)—(CH$_2$)$_m$—M, wherein V is O or S, M is mesylate, tosylate, triflate, Cl, Br or I, and U, A$^1$, A$^2$, A$^3$, A$^4$, A$^5$, A$^6$, A$^7$, A$^8$, A$^9$, A$^{10}$, W, m, n and p are as defined above, or wherein HV is mesylate, tosylate, triflate, Cl, Br or I, and M is OH or SH, or b) reacting a compound of formula (III)

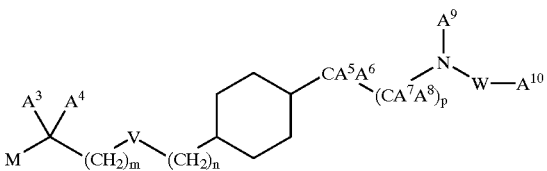

(III)

with a compound NHA$^1$A$^2$, wherein M is mesylate, tosylate, triflate, Cl, Br or I, and A$^1$, A$^2$, A$^3$, A$^4$, A$^5$, A$^6$, A$^7$, A$^8$, A$^9$, A$^{10}$, V, W, m, n and p are as defined above, and optionally converting a compound of formula (I) as defined above to a pharmaceutically acceptable salt, and optionally converting a compound of formula (I) as defined above, wherein U is a lone pair, to a corresponding compound wherein U is O.

Reactions of a compound of formula (II) with a compound (A$^1$,A$^2$,U)N—C(A$^3$,A$^4$)—(CH$_2$)$_m$—M can be carried out by procedures known in the art and described in the Scheme 8 in a solvent like N,N-dimethylformamide, N,N-dimethylacetamide or nitromethane in the presence of a base like sodium hydride or 2,6-di-tert-butylpyridine in a temperature range of e.g. 0° C. to 80° C. Reactions of a compound of formula (III) with a compound NHA$^1$A$^2$ can be carried out by procedures known in the art and described in the examples preferentially in solvents like N,N-dimethylacetamide, N,N-dimethylformamide or methanol, preferentially between room temperature and 80° C.

A compound as defined above can be converted to a pharmaceutically acceptable salt by procedures known in the art such as by a treatment with a corresponding acid in a solvent like ethanol, methanol or dichloromethane in a temperature range of e.g. e.g. −20° C. and +40° C. A compound as defined above, wherein U is a lone pair can be converted to a compound wherein U is O by procedures known in the art such as by reaction with a mixture of hydrogen peroxide, urea adduct and phthalic anhydride in dichloromethane at room temperature.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

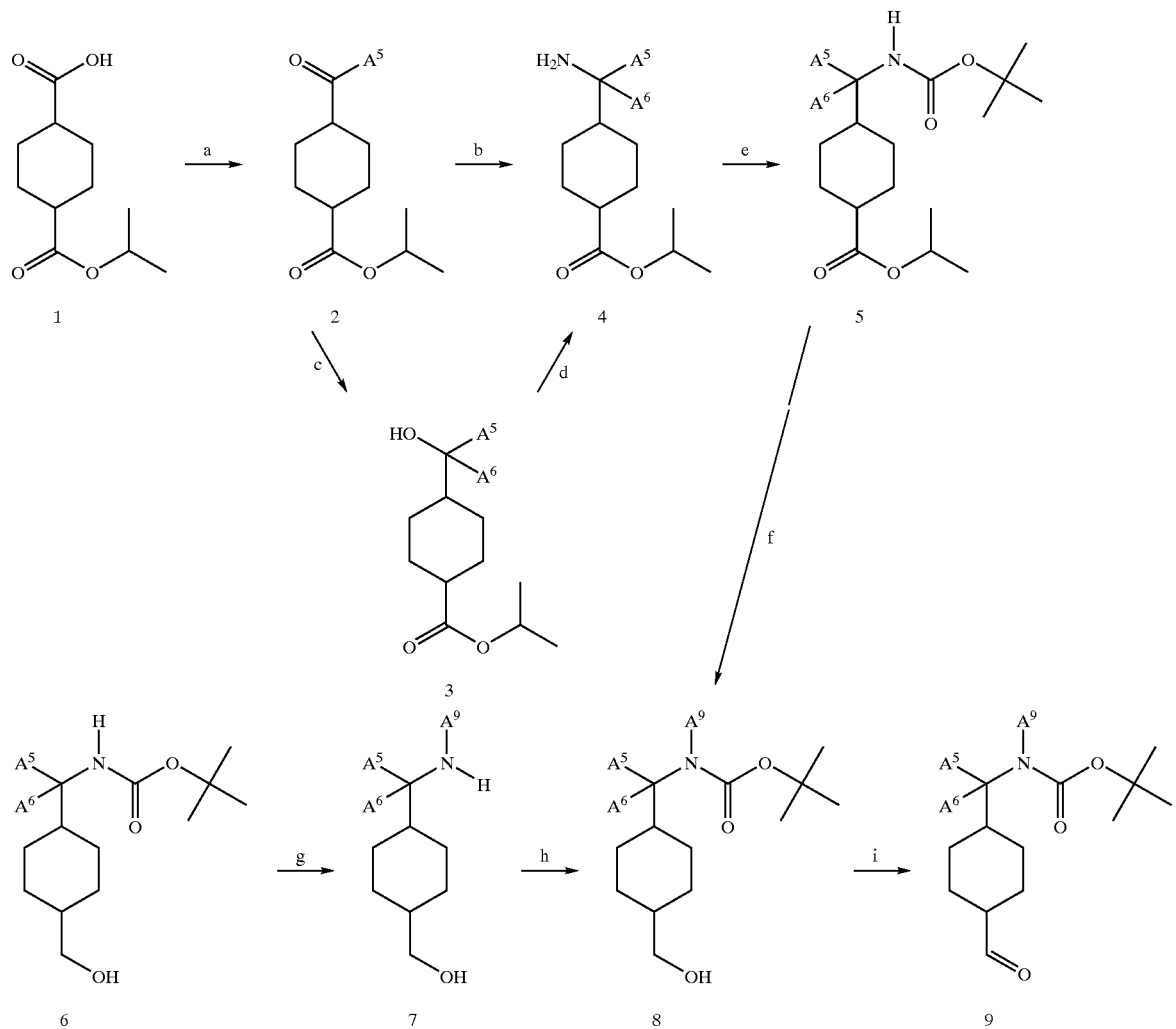

Scheme 1

Trans-(4-methylaminomethyl-cyclohexyl)-methanol (7-trans with $A^5$, $A^6$=H; $A^9$=Me) can be obtained from trans-(4-hydroxymethyl-cyclohexylmethyl)-carbamic acid tert-butyl ester [U.S. (2000) U.S. Pat. No. 6,022,969 A] by treatment with lithium aluminum hydride in tetrahydrofuran between room temperature and the reflux temperature of the tetrahydrofuran (step g). Introduction of a tert-butoxycarbonyl protective function by treatment with di-tert-butyl-dicarbonate in methanol/triethylamine between −10° C. and room temperature gives compound 8 ($A^5$, $A^6$=H; $A^9$=Me) (step h). Compounds with variable alkyl groups $A^5$, $A^6$ and $A^9$ are prepared from cyclohexane-1,4-dicarboxylic acid mono alkyl esters, preferentially mono isopropyl esters, by first introduction of the first alkyl group $A^5$ by conversion of the acid moiety in 1 into the corresponding acid chlorides and treatment with a di-alkyl cuprates in solvents like ether or tetrahydrofuran preferentially at −78° C. (step a). Reductive amination of the ketones 2 with ammonium formiate and sodium cyanoborohydride in solvents like methanol or ethanol preferentially at room temperature then gives amines 4 with $A^6$ equal H (step b). If the ketones 2 are treated with an alkyllithium reagent in the presence of titanium tetrachloride in ether as described in Tetrahedron 42(11), 2931–2935 (1986), then tertiary alkohols 3 are formed (step c). The tertiary alkohols 3 are then reacted with trimethylsilylazide in the presence of borontrifluoride etherate in a solvent like benzene to from the azides as described in Tetrahedron Letters 28(51), 6513–6516 (1987); the azides are subsequently hydrogenated with hydrogen gas and e.g. a palladium catalyst in solvents like methanol, ethanol or tetrahydrofuran to the primary amines 4 (step d). Introduction of a tert-butoxycarbonyl protective function at the primary amino moiety of compounds 4 leads then to compounds 5 (step e). Compounds 5 can be N-alkylated at the primary tert-butoxycarbonyl protected amino function with an alkyl halide in the presence of a base like sodium hydride in a solvent like N,N-dimethylformamide or acetonitrile at temperatures between room temperature and 80° C. to introduce substituents $A^9$; after reduction of the ester function with e.g. lithium aluminum hydride in solvents like tetrahydrofuran at temperatures between −50° C. and room temperature, the compounds 8 are obtained (step f). Compounds 8 are subsequently oxidized to the corresponding aldehydes 9 by using e.g. Swern conditions: oxalyl chloride/ dimethylsulfoxide/ triethylamine in dichloromethane, −78° C. to room temperature (step i).

Scheme 2

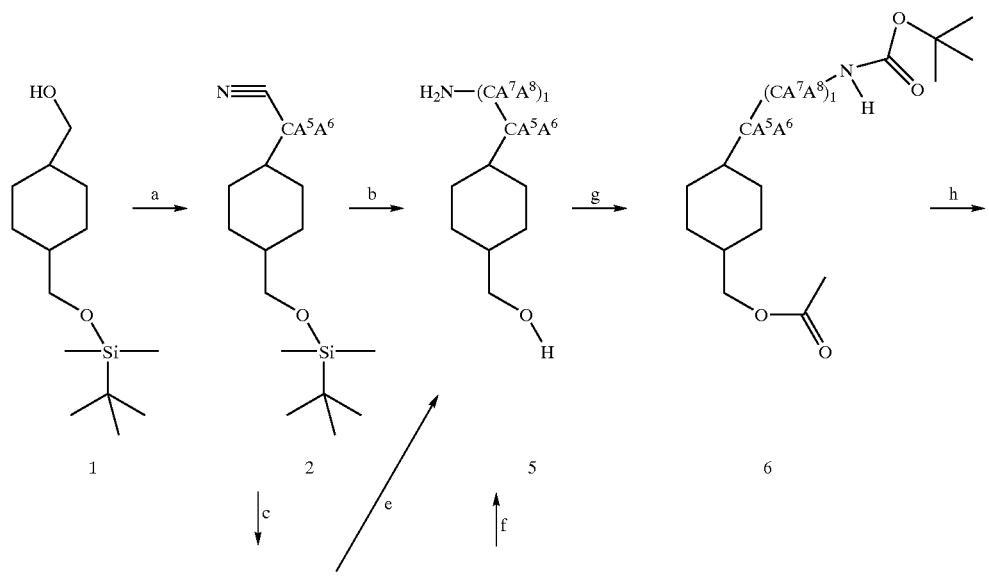

-continued

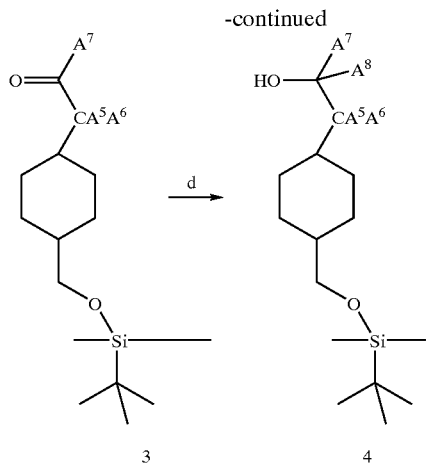

3 → d → 4

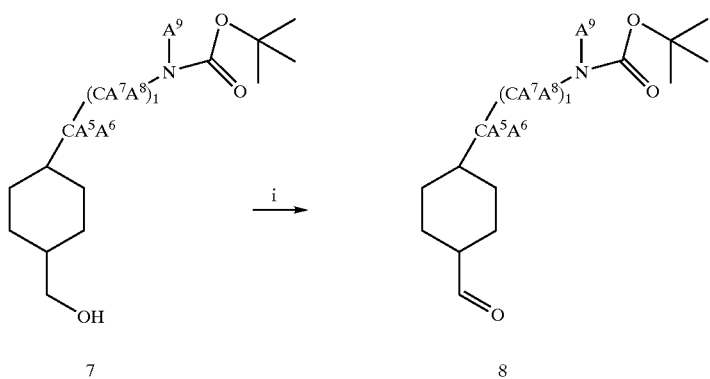

7 → i → 8

[4-(Tert-butyl-dimethyl-silanyloxymethyl)-cyclohexyl]-methanol compounds 1 are prepared from the corresponding bis-hydroxymethyl cyclohexane derivatives by treatment with one equivalent of n-butyl lithium in tetrahydrofuran at −78° C. followed by one equivalent of tert-butyl-dimethyl-chlorosilane at −65° C. to room temperature. Mesylation of [4-(tert-butyl-dimethyl-silanyloxymethyl)-cyclohexyl]-methanols 1 (methanesulfonyl chloride in dichloromethane and triethylamine at 0–10° C.) gives the corresponding methanesulfonates, which are treated with sodium cyanide in N,N-dimethylformamide at 80° C. to give the cyano compounds 2 with $A^5$, $A^6$ equal to hydrogen (step a). Direct reduction of the cyano compounds 2 e.g. by hydrogenation with a platinum catalyst in acidic methanol gives the primary amines 5 with $A^5$, $A^6$, $A^7$ and $A^8$ equal to hydrogen and without tert-butyl-dimethyl-silyl protective function (step b). Alternatively, alkyl groups $A^5$ and/or $A^6$ can be introduced into cyano compounds 2 by treatment with a base like potassium tert-butoxide or sodium hydride in solvents like tetrahydrofuran or 1,2-dimethoxyethane followed by addition of one or sequentially two different alkyl halides, a reaction preferentially performed between 0° C. and 80° C. Mono and/or dialkyl cyano compounds 2 can be reduced to compounds 5 as described above (step b). Alternatively, cyano compounds 2 can be reacted with alkyl Grignard reagents in solvents like ether or tetrahydrofuran between 0° C. and the reflux temperature of the solvent to form the corresponding alkyl ketones 3 (step c). Reductive amination of the ketones 3 with ammonium formiate and sodium cyanoborohydride in solvents like methanol or ethanol preferentially at room temperature followed by removal of the tert-butyl-dimethyl-silyl protective function with aqueous hydrofluoric acid in a water/acetonitrile mixture at room temperature gives amines 5 with $A^8$ equal to H (step e). Treatment of ketones 3 with a second alkyl Grignard reagent under conditions similar to those just described gives tertiary alcohols 4 (step d). The tertiary alcohols 4 are then reacted with trimethylsilylazide in the presence of borontrifluoride etherate in a solvent like benzene to form the corresponding azide as described in Tetrahedron Letters 28(51), 6513–6516 (1987) and the azide is hydrogenated with hydrogen gas and e.g. a palladium catalyst in solvents like methanol, ethanol or tetrahydrofuran to the primary amines 5 without tert-butyl-dimethyl-silyl protective function, which gets lost under the conditions of the azide formation (step f). Treatment of the amino-alcohols 5 first with di-tert-butyl-dicarbonate in dichloromethane in the presence of triethylamine followed by acetic anhydride and pyridine in dichloromethane gives the di-protected compounds 6 (step g). Compounds 6 can be N-alkylated at the primary tert-butoxycarbonyl protected amino function with an alkyl halide in the presence of a base like sodium hydride in a solvent like N,N-dimethylformamide or acetonitril at temperatures between room temperature and 80° C. to introduce substituents $A^9$ and give, after basic cleavage of the acetate function, the primary hydroxy compounds 7 (step h). The primary hydroxy compounds 7 can be oxidized subsequently to the corresponding aldehydes 8 by using e.g. Swern conditions: oxalyl chloride/dimethylsulfoxide/triethylamine in dichloromethane, −78° C. to room temperature (step i).

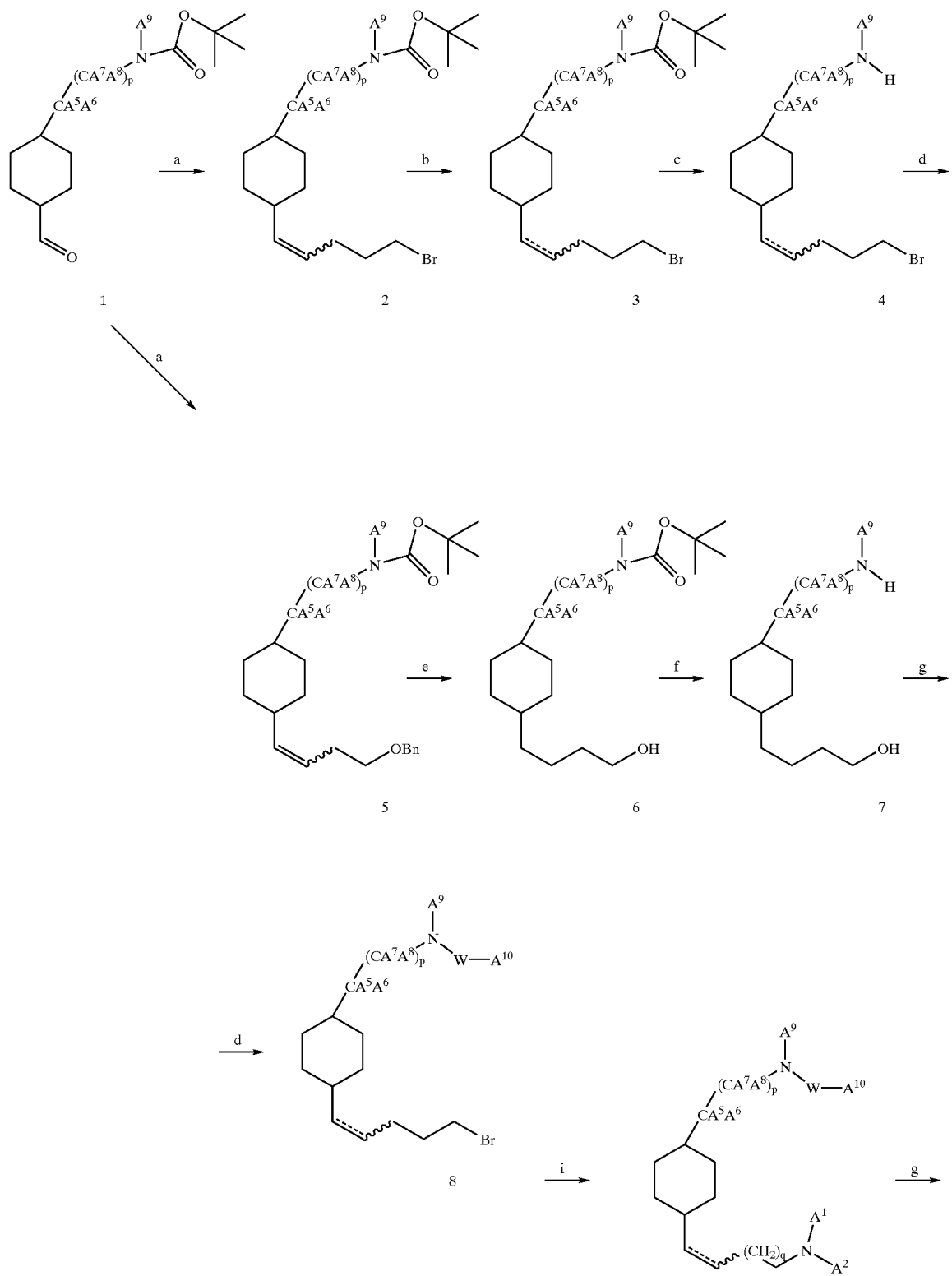
Scheme 3

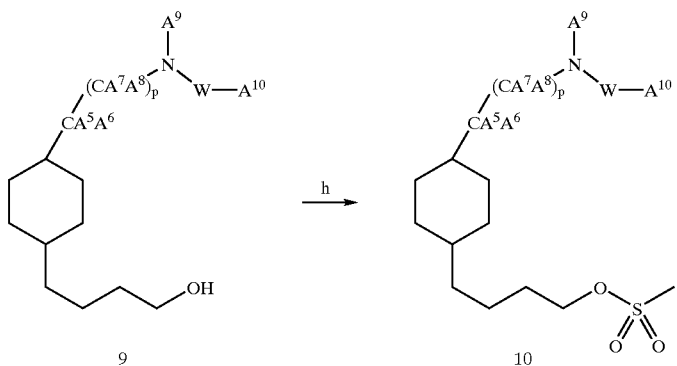

Aldehydes 1 undergo Wittig reactions with a variety of ylids. Thus, treatment with (benzyloxyalkyl or haloalkyl) triphenylphosphonium salts, e.g. 4-(bromobutyl) triphenylphosphonium bromide or 3-benzyloxypropyl) triphenylphosphonium bromide, preferentially with finely milled potassium carbonate as base in solvents like 2-methyl-2-butanol or tert-amyl alcohol at temperatures between room temperature and the reflux temperature of the solvents, yields [4-(5-bromo-(E,Z)-pent-1-enyl)-cyclohexylalkyl]-alkyl-carbamic acid tert-butyl esters 2 or [4-(4-benzyloxy-(E,Z)-but-1-enyl)-cyclohexylalkyl]-alkyl-carbamic acid tert-butyl esters 5 (step a). Optionally, the double bond present can be reduced by hydrogenation leading to compounds 3 and 6 (step b and e). If a benzyloxy function has been present in the phosphonium salt and the corresponding olefin, then, the hydrogenolytic removal of the benzyl group reduces the double bond at the same time (step e). After removal of the tert-butoxycarbonyl protective function with acid (steps c and f), the corresponding amine compounds 4 and 7 are converted into compounds 8 and 9 carrying the $NA^9WA^{10}$ groups by the following procedures (steps d and g):

a) $NA^9WA^{10}$=Sulfonamides or carbamates: treatment with an aryl-sulfonyl chloride or with an aryl chloroformate preferentially in the presence of diisopropyl-ethylamine, potassium carbonate, tetrahydrofuran and water between −10° C. and room temperature.
b) $NA^9WA^{10}$=Thiocarbamates: The amines may be reacted with $A^{10}OCSCl$ in solvents like dioxane, dichloromethane or tetrahydrofuran in the presence of a base like diisopropyl-ethylamine or aqueous potassium carbonate.
c) $NA^9WA^{10}$=Ureas: The amines may be reacted with isocyanate in dioxane at room temperature.
d) $NA^9WA^{10}$=Thioureas: The amines may be reacted with isothiocyanate in dioxane at room temperature.
e) $NA^9WA^{10}$=Amides: The amines may be reacted with $A^{10}COCl$/Huenigsbase in $CH_2Cl_2$, $A^{10}COOH$/EDCI/DMAP (via formation of the symmetrical anhydride, and subsequent addition of the starting amine at −10° C. to room temperature) or alternatively with $A^{10}COOH$/EDCI/DMAP or $A^{10}COOH$/Huenig's base or NMM/EDCI/HOBT in DMF, dioxane or $CH_2Cl_2$ at room temperature.
f) $NA^9WA^{10}$=Sulfamides: The amines may be reacted with sulfamoyl chlorides in dioxane in the presence of an excess of triethylamine. The sulfamoyl chlorides can be prepared from $A^{10}NH_2$ and chlorosulfonic acid in $CH_2Cl_2$ at 0° C. to room temperature followed by reaction with $PCl_5$ in toluene at 75° C. Alternatively, the sulfamoyl chlorides can be synthesized in acetonitrile with $A^{10}NH_2$ and sulfuryl chloride at 0° C. to 65° C.

Compounds 9, which contain a hydroxy function, are converted into the corresponding methanesulfonates by treatment with methanesulfonyl chloride in dichloromethane and triethylamine at 0–10° C. (step h).

Amination of halides 8 and methanesulfonates 10 with amines $A^1A^2NH$ is preferentially being performed in N,N-dimethylacetamide or in N,N-dimethylformamide, between room temperature and 80° C., or in methanol and optionally 1,8-diazabicyclo[5.4.0]undec-7-ene at room temperature to reflux and yields the final amine compounds 11 (q=1 or 2) (step i). Amines 11 may optionally be converted into a salt or into the N-oxides using a mixture of hydrogen peroxide urea adduct and phthalic anhydride in dichloromethane at room temperature. In case $A^1A^2N$ (U absent) signifies imidazol-1-yl, then, the transformation of halides 8 and methanesulfonates 10 is performed with imidazole, sodium hydride in a solvent like N,N-dimethylformamide preferentially at temperatures between 0° C. and room temperature. If $A^1$=H, heteroaromatic moieties $A^1$ may be introduced into compounds 11 by treatment with halo heteroaromatics in the presence of Huenig's base in N,N-dimethylformamide between room temperature and 100° C. (Ger. Offen. (1990), DE3905364 A1). Alternatively, Buchwald conditions e.g. $Pd(OAc)_2$, 2-(Dicyclohexylphosphino)biphenyl, NaOtBu in toluene might be applied (John P. Wolfe, Hiroshi Tomori, Joseph P. Sadighi, Jingjun Yin, and Stephen L. Buchwald, J. Org. Chem., 65 (4), 1158–1174, 2000).

Scheme 4

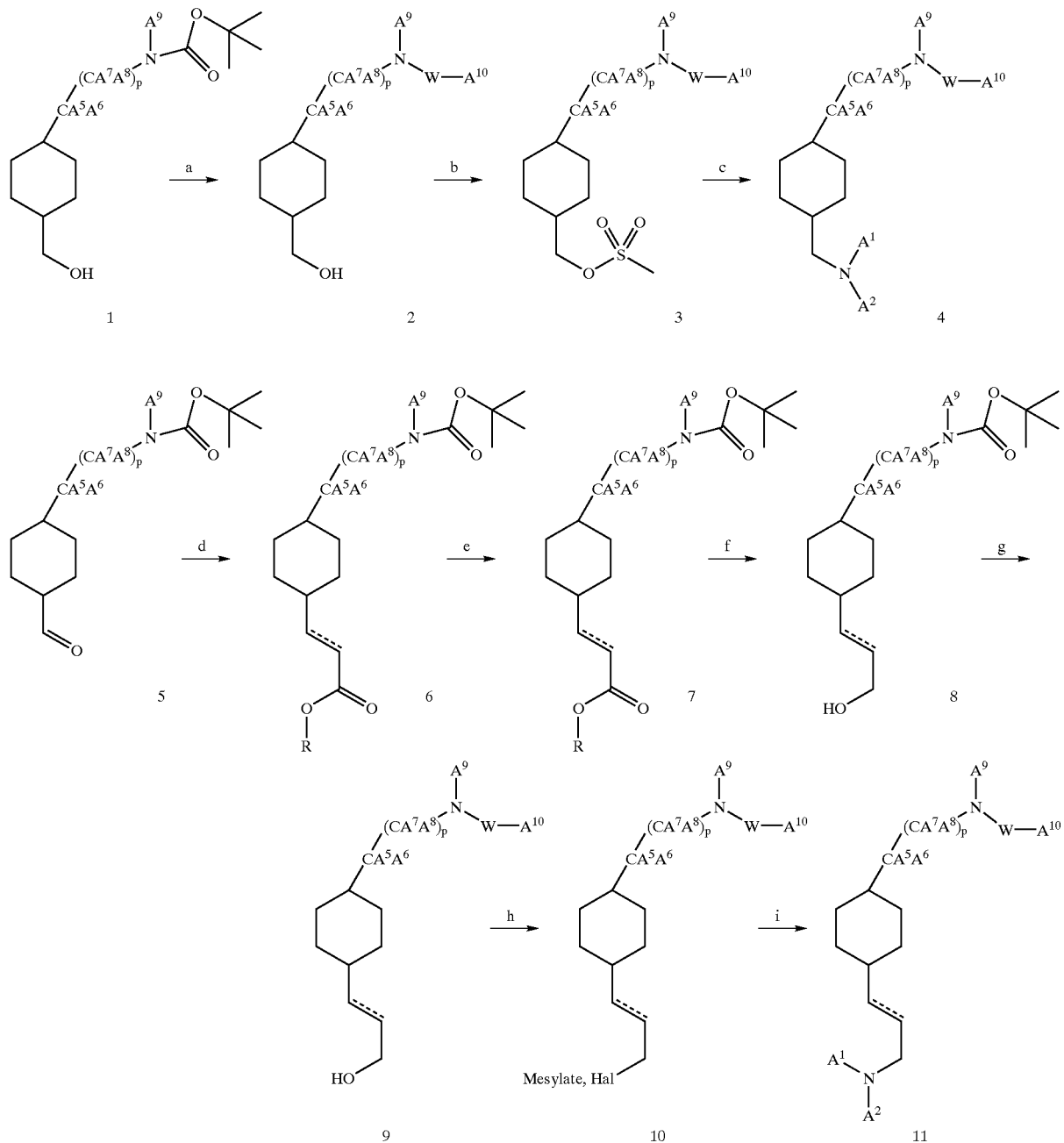

Primary alcohols 1 are treated with hydrogen chloride in dioxane at room temperature to remove the tert-butoxycarbonyl protective function; the primary or secondary amine thus formed then converted into groups $NA^9WA^{10}$ as described in Scheme 3 (step a). Conversion of the primary alcohols 2 into the corresponding methanesulfonate esters 3 is then performed as described above (step b). Transformation of methanesulfonates 3 into final compounds 4 is then performed as described in Scheme 3 (step c).

Aldehydes 5 react with (triphenyl-phosphoranylidene)-acetic acid esters in dichloromethane or toluene between room temperature and 110° C. to the corresponding unsaturated ester compounds 6 (step d). Optionally, the double bond in the unsaturated ester compounds 6 can be hydrogenated using a palladium catalyst in a solvent like methanol or ethanol preferentially at room temperature (step e). Subsequently, the ester function can be reduced using lithium aluminium hydride or diisobutyl aluminium hydride in tetrahydrofuran or 1,2-dimethoxyethane at temperatures between −78° C. and the reflux temperature of the solvents giving the primary alcohol compounds 8 (step f). Removal of the tert-butoxycarbonyl protective function with acid and treatment of the corresponding amine compounds as described in Scheme 3 gives the corresponding compounds 9 carrying groups $NA^9WA^{10}$ (step g). The primary alcohol compounds 9 are then transformed into the corresponding methanesulfonate esters 10 as described above (step h), a process which leads to mixtures of methanesulfonate esters and chlorides or pure chlorides, if the double bond is still present. Transformation of methanesulfonate esters, mixtures of methanesulfonate esters and chlorides or pure chlorides 10 into final compounds 11 is then performed as described in Scheme 3.

Scheme 5

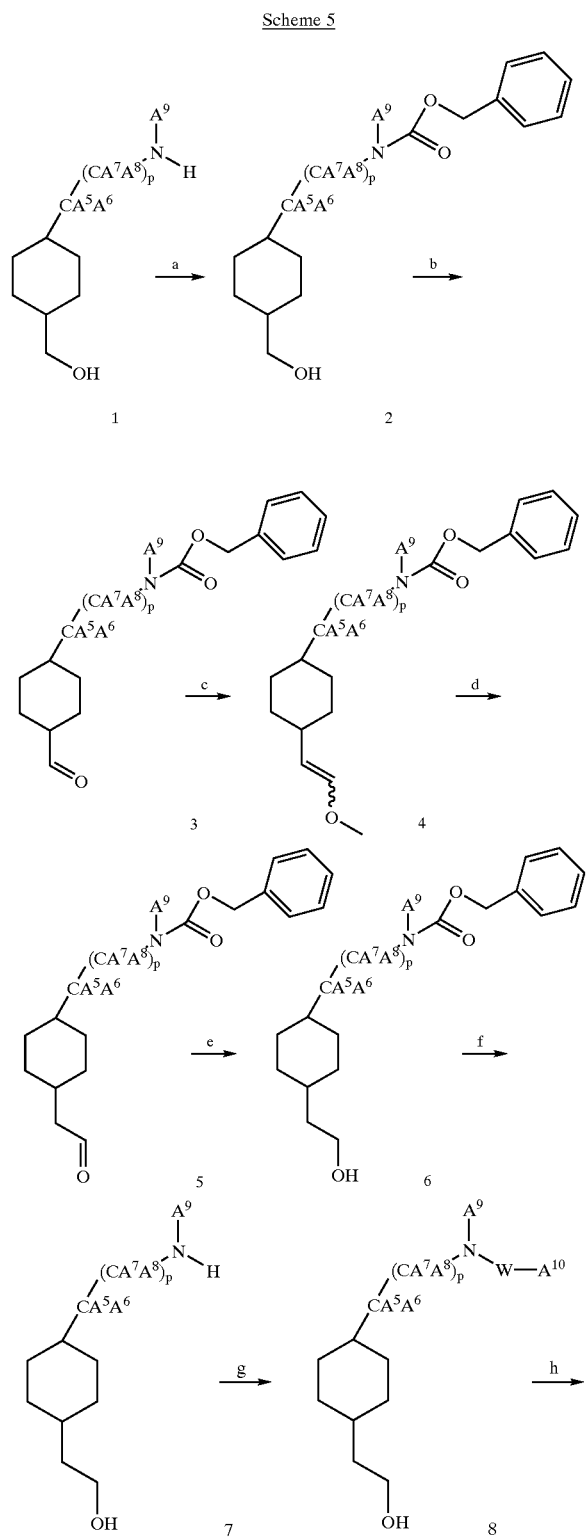

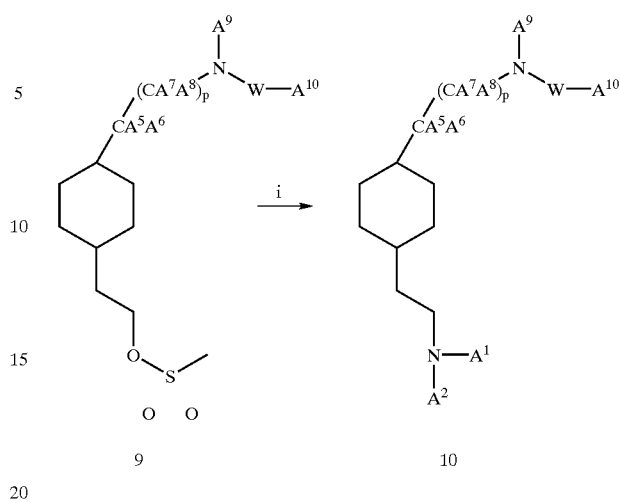

Aminoalkohols 1 can be protected a the amino-function e.g. by treatment with N-(benzyloxycarbonyloxy)-succinimide in methanol to give the Z-protected analogues 2 (step a). The Z-protected analogues 2 are subsequently oxidized to the corresponding aldehydes 3 by using e.g. Swern conditions: oxalyl chloride/dimethylsulfoxide/triethylamine in dichloromethane, −78° C. to room temperature (step b). Wittig reaction with (methoxymethyl) triphenylphosphonium chloride and potassium tert-butylate in tetrahydrofuran, preferentially between −10° C. and room temperature, gives enol ethers 4 (step c) and after hydrolysis with 2N aqueous hydrochloric acid in tetrahydrofuran aldehydes 5 (step d). Reduction to the primary alcohols 6 with sodium borohydride in methanol followed by hydrolytic removal of the Z-protective function then leads to primary alcohols 7 (step e and f), which are converted into amino compounds 10 as described for aminoalkhols 7 in Scheme 3 (steps g, h, i).

Scheme 6

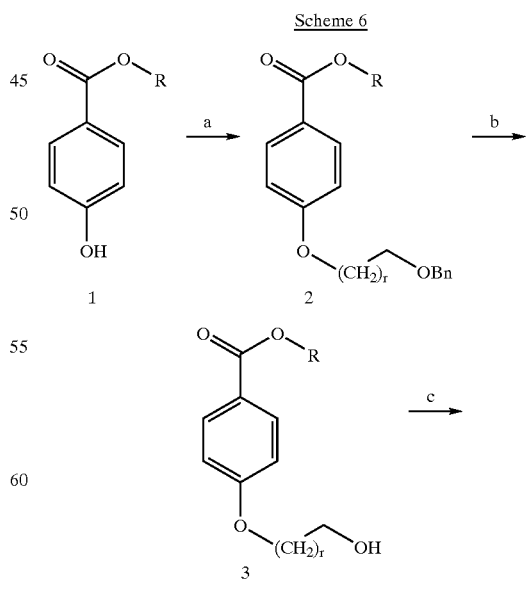

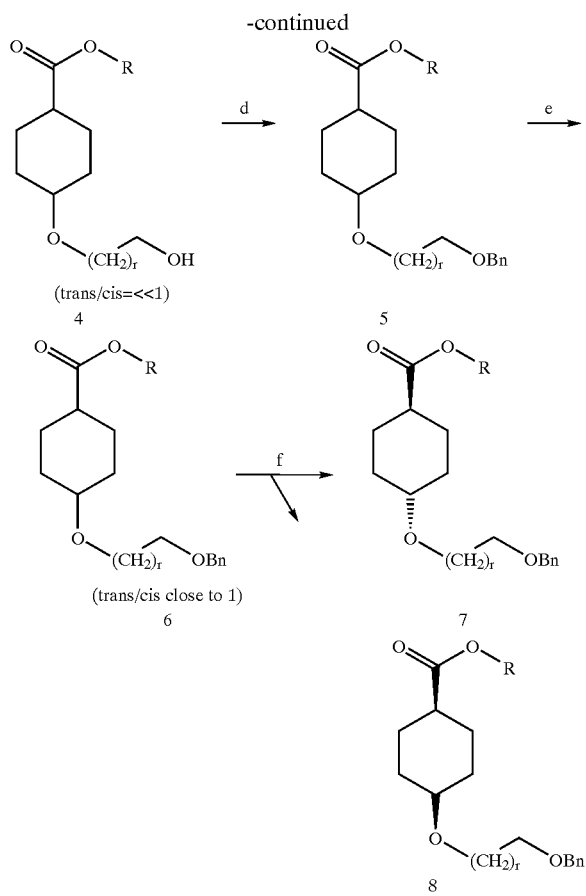

4-(Hydroxy-alkoxy)-benzoic acid esters 3 can be prepared from 4-hydroxy-benzoic acid esters 1 by various well known methods, e.g. Mitsunobu ether formation (diethyl-azo-dicarboxylate, triphenylphosphine in tetrahydrofuran between −10° C. and the reflux temperature of the tetrahydrofuran) with a mono-benzyl protected dihydroxy-alkane (r=2–8) and subsequent deprotection (hydrogenolysis with hydrogen gas and a palladium catalyst in methanol at room temperature) or by direct alkylation with a suitable bromo- or chloro-hydroxy alkane in the presence of a base like potassium carbonate in solvents like acetone, acetonitrile or N,N-dimethylformamide between room temperature and 100° C. (steps a and b). Catalytic hydrogenation of 4-(hydroxy-alkoxy)-benzoic acid esters 3 using a rhodium catalyst and hydrogen gas at temperatures between room temperature and 80° C. and pressures of hydrogen between normal pressure and 20 bar in solvents like ethanol or methanol and optionally a tertiary base like triethylamine gives mixtures of cis and trans 4-(hydroxy-alkoxy)-cyclohexane carboxylic acid esters 4 with a strong preference for the cis isomers (step c). Isomerization to a cis/trans mixture close to 1:1 can be achieved after reintroduction of the benzyl group (e.g. with benzyl 2,2,2-trichloroacetimidate, trifluoroacetic acid in dichloromethane/cyclohexane at room temperature, step d) by quenching the enolate formed with lithium diisopropylamide at −78° C. in tetrahydrofuran by treatment with methanol at the same temperature (step e). This mixture of cis and trans 4-(benzyloxy-alkoxy)-cyclohexane carboxylic acid esters 6 can be separated by chromatography into the pure cis and trans isomers 8 and 7 (step f).

Scheme 7

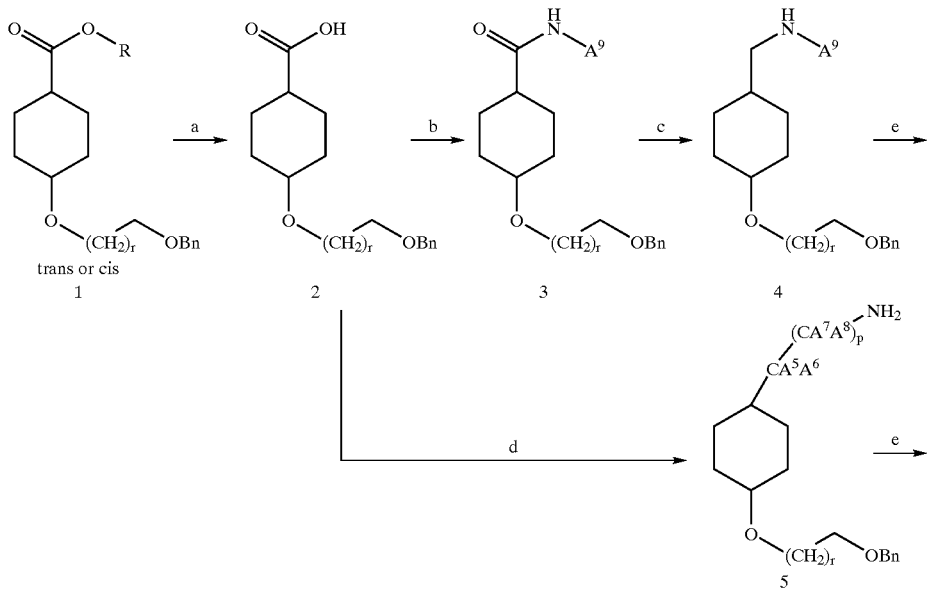

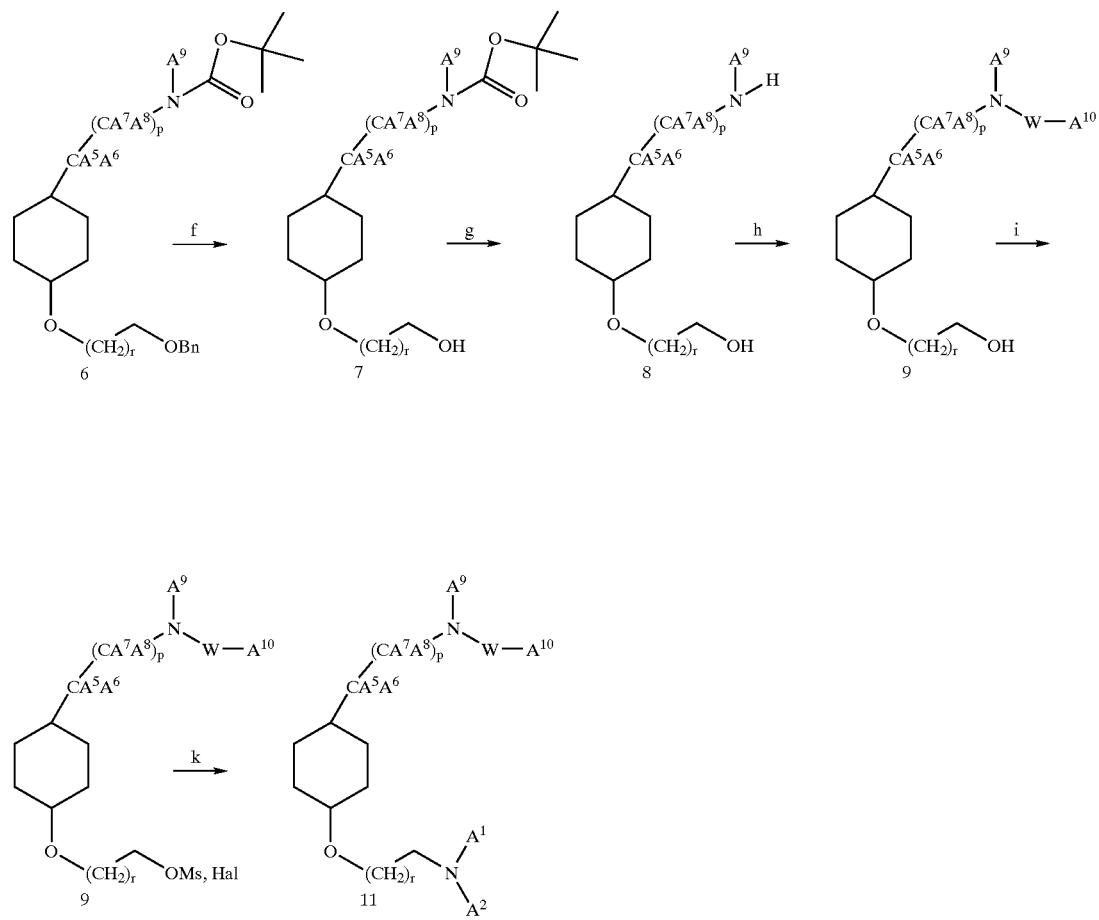

Pure cis or trans 4-(benzyloxy-alkoxy)-cyclohexane carboxylic acid esters 1 can be converted into the corresponding N-alkyl amides 3 by well known procedures of saponification and amide formation via the corresponding acid chloride as intermediate (steps a and b). N-Alkyl amides 3 can then be reduced to the corresponding N-alkyl amines 4 with lithium aluminium hydride in tetrahydrofuran between room temperature and the reflux temperature of tetrahydrofuran (step c). Optionally, a tert-butoxycarbonyl protective function can be introduced with di-tert-butyl-dicarbonate as reagent before removal of the benzyloxy function (steps e and f). Compounds 5 with either a two carbon chain between cyclohexane ring and the amino function and/or substituents $A^5 A^6$, $A^7$, $A^8$ different from hydrogen are prepared from the carboxylic acid 2 as described in Schemes 1 and 2: i) the carboxylic acids 2 are modified in analogy to the procedures described for the carboxylic acids 1 in Scheme 1; or ii) the carboxylic acids 2 are reduced to the corresponding primary alcohol with borane-tetrahydrofuran complex in tetrahydrofuran between $-10°$ C. and the reflux temperature of tetrahydrofuran and then transformed in analogy to the procedures described for the hydroxy methyl compounds 1 in Scheme 2, leading to the primary amines 5 (step d). After introduction of a tert-butoxycarbonyl protective function into primary amines 4 and 5, the tert-butoxycarbonyl protected nitrogen function can be alkylated as described above leading to compounds 6 (step e). Hydrogenolytic removal of the benzyl function and removal of the tert-butoxycarbonyl protective function under acidic conditions leads to cis or trans amino alcohol compounds 8 (steps f and g). Cis or trans amino alcohol compounds 8 are subsequently converted into analogues 9 carrying a group $NA^9WA^{10}$ as described in Scheme 3 (step h). Conversion of the primary alcohols 9 into the corresponding methanesulfonate esters 10 is then performed as described above (step i). Transformation of methanesulfonate esters 10 into final compounds 11 is then performed as described in Scheme 3 (step k).

Scheme 8

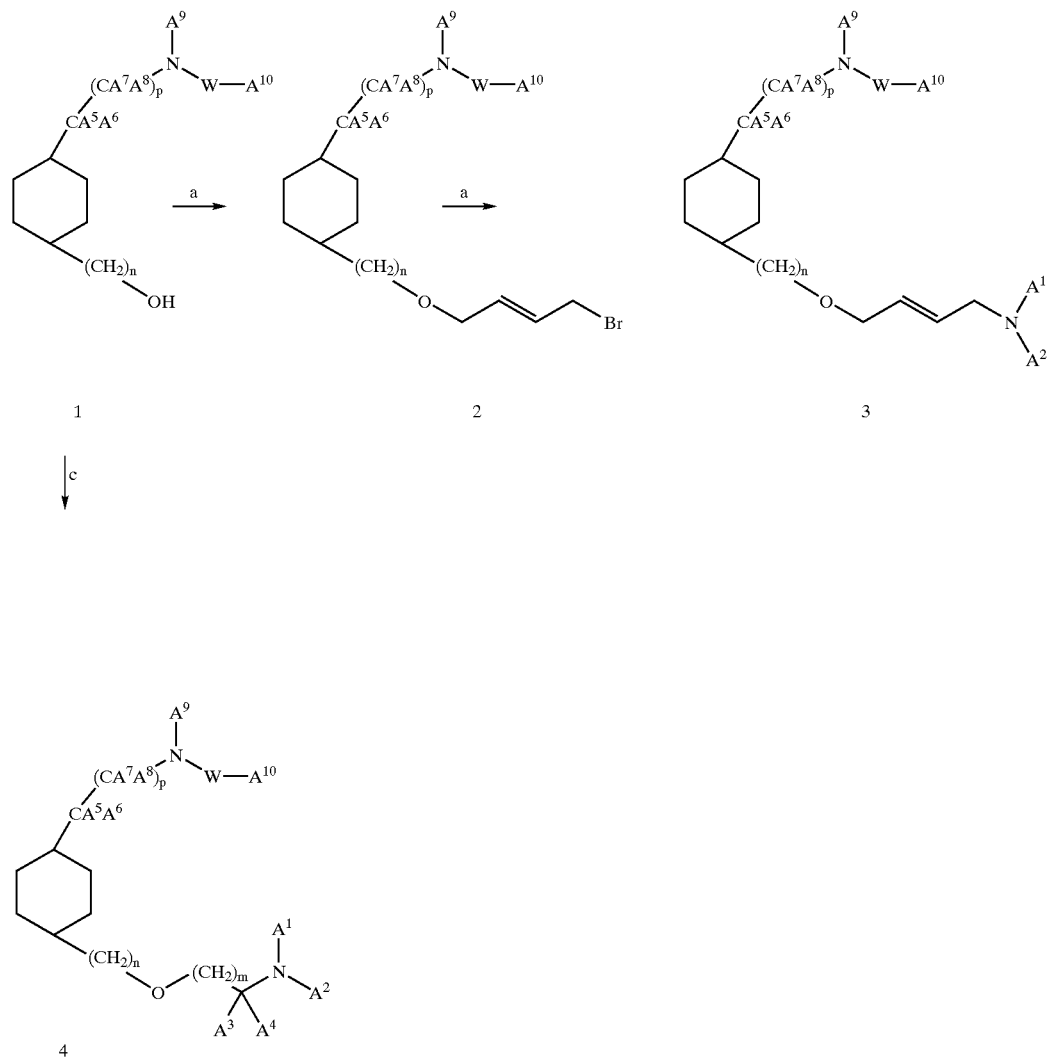

Primary alcoholes 1 are reacted with 1,4-dibromo-2-butene in a vigorously stirred mixture of dichloromethane and 50% w/w sodium hydroxide in the presence of tetrabutylammonium hydrogensulfate preferentially at room temperature to yield bromides 2 (step a). Transformation of bromides 2 into final compounds 3 is then performed as described in Scheme 3 (step b).

Primary alcohols 1 are converted to amines 4 by attaching the pre-assembled fragment $A^1A^2NC(A^3A^4)(CH_2)_m$—OH, which can be synthesized by known methods (step c): Primary alcohols 1 are first converted into the corresponding methanesulfonates; fragments $A^1A^2NC(A^3A^4)(CH_2)_m$—OH are treated with sodium hydride in N,N-dimethylformamide at 0° C. to room temperature, then, the methanesulfonates are added and the condensation performed between 0° C. and 80° C. to give amines 4. Alternatively, primary alcohols 1 are converted to the corresponding triflates (with trifluoromethansulfonic anhydride/2,6-di-tert-butylpyridine in dichloromethane at 0° C.). These triflates are then reacted in situ with alcohols $A^1A^2NC(A^3A^4)(CH_2)_m$—OH in the presence of 2,6-di-tert-butylpyridine as base in nitromethane at room temperature to 60° C. to yield amines 4 [following a procedure of Belostotskii, Anatoly M.; Hassner, Alfred. Synthetic methods. 41. Etherification of hydroxysteroids via triflates. Tetrahedron Lett. (1994), 35(28), 5075–6].

Scheme 9

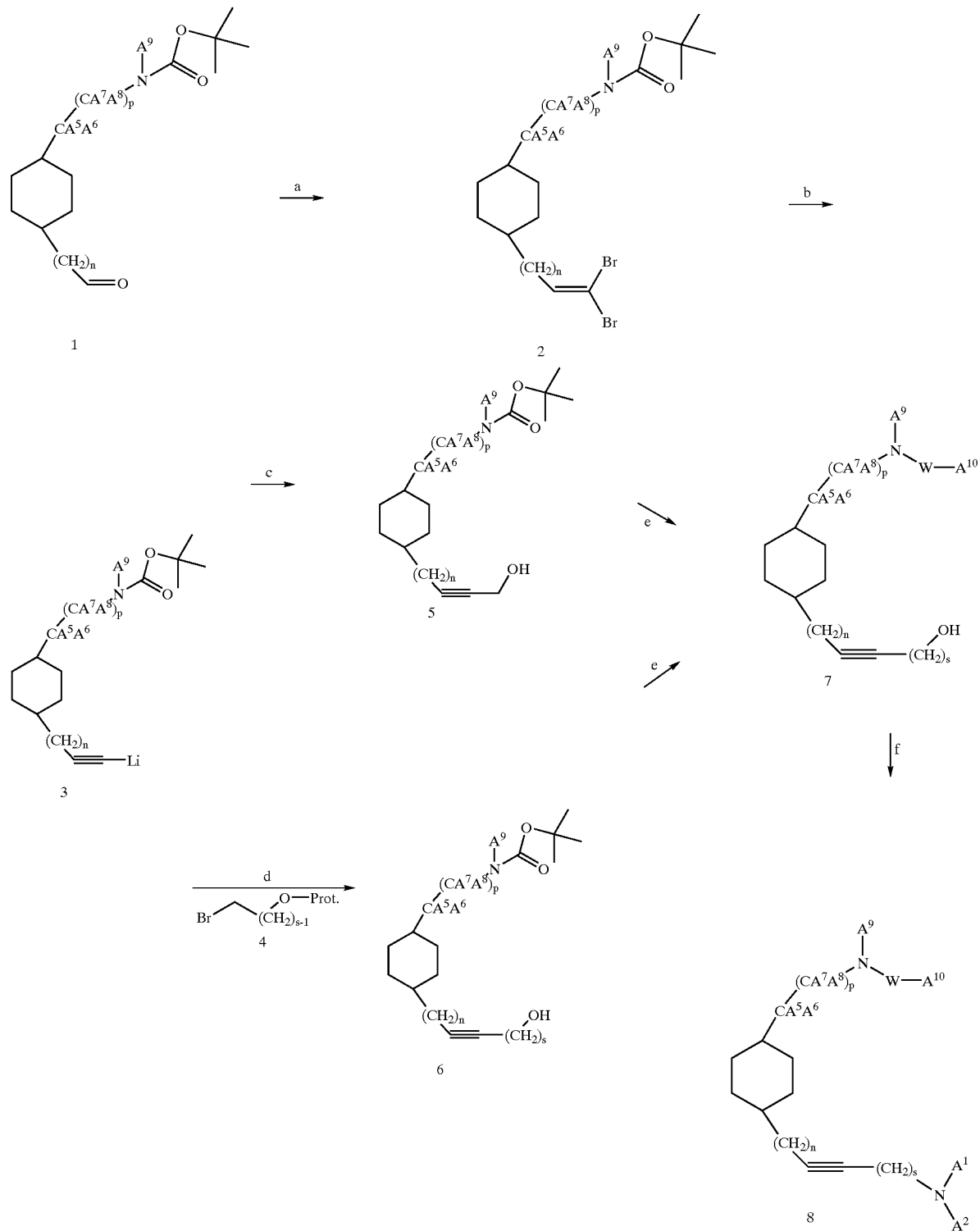

Aldehydes 1 can be treated with triphenylphosphine, tetrabromomethane and triethylamine in dichloromethane at 0° C. to room temperature to yield 2,2-dibromo-vinyl derivatives 2 (step a). Rearrangement with n-buyl-lithium (ca 1.6 M in hexane) in tetrahydrofuran at −78° C., followed by reaction with formaldehyde (−78° C. to room temperature) gives the propargyl alcohols 5 [step b and c; following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E. J. Chem. Soc., Perkin Trans. 1 (1990), (5), 1415–21]. For longer side chains, the rearrangement is performed with n-butyl lithium (ca 1.6 M in hexane) in tetrahydrofuran at −78° C. as above, followed by addition of a co-solvent such as 1,3-dimethyl-3,4,5,6-tetrahydro-2(1H)-pyrimidinon and reaction with O-protected ω-bromo-alcohols 4 (s=2–7) (step b and d; e.g. 1-bromo-ω-tetrahydropyranyloxyalkane) to give after removal of the O-protective function (e.g. with pyridinium p-toluenesulfonate in methanol at room temperature to 50° C.) compounds 6. Conversion of compounds 5 and 6 into final compounds 8 can be performed as described in Scheme 3 (steps e and f).

The following tests were carried out in order to determine the activity of the compounds of formula I and their salts.

Inhibition of Human Liver Microsomal 2,3-oxidosqualene-lanosterol cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/µl with ethanol and mixed with phosphate buffer-1% BSA (bovine serum albumin). A stock solution of 1 mM test substance in DMSO was diluted to the desired concentration with phosphate buffer-1% BSA. 40 µl of microsomes were mixed with 20 µl of the solution of the test substance and the reaction was subsequently started with 20 µl of the [$^{14}$C]R,S-MOS solution. The final conditions were: 0.4 mg/ml of microsomal proteins and 30 µl of [$^{14}$C]R,S-MOS in phosphate buffer, pH 7.4, containing 0.5% albumin, DMSO<0.1% and ethanol<2%, in a total volume of 80 µl.

After 1 hour at 37° C. the reaction was stopped by the addition of 0.6 ml of 10% KOH-methanol, 0.7 ml of water and 0.1 ml of hexane:ether (1:1, v/v) which contained 25 µg of non-radioactive MOS and 25 µg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the IC$_{50}$ value was calculated, i.e. the concentration required to reduce the conversion of MOS into lanosterol to 50% of the control value. The preferred compounds of the present invention exhibit IC$_{50}$ values of 1 nM to 10 µM, preferably of 1–100 nM.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

General Remarks

All reactions were performed under argon.

Example 1

1.1

2.90 g (11.0 mmol) trans-(4-hydroxymethyl-cyclohexylmethyl)-carbamic acid tert-butyl ester [U.S. (2000) U.S. Pat. No. 6,022,969 A] dissolved in 15 ml of tetrahydrofuran were added slowly to a suspension of 0.92 g of lithium aluminium hydride in 10 ml of tetrahydrofuran. The reaction mixture was then stirred at 50° C. for 4 hours, cooled to 0° C., treated with 2 g of ice, stirred at room temperature for 30 min., diluted with ethyl acetate, dried over sodium sulfate, filtered and evaporated. Thus, crude trans-(4-methylaminomethyl-cyclohexyl)-methanol was obtained [MS: 158 (MH$^+$)], which was dissolved in 20 ml of methanol, cooled to −10° C. and treated at once with 2.77 g di-tert-butyl-dicarbonate. Then, the reaction mixture was stirred at −10° C. for 30 min. and at room temperature for 1 hour. Subsequently, 5 ml of water and 5 ml of triethylamine were added and the reaction mixture evaporated under reduced pressure. It was then poured into 100 ml of an ice/water mixture and extracted 3 times with 100 ml of dichloromethane. The combined dichloromethane phases were dried over magnesium sulfate and evaporated under reduced pressure. The residue formed was chromatographed on silica gel with a 1:1 v/v mixture of dichloromethane and ethylacetate as the eluent giving 2.5 g (82%) trans-(4-hydroxymethyl-cyclohexylmethyl)-methyl-carbamic acid tert-butyl ester as colorless viscous oil, MS: 257 (M$^+$).

1.2

0.45 ml of oxalyl chloride in 5.0 ml of dichloromethane were cooled to −78° C.; then, 0.41 g of dimethylsulfoxide in 2.0 ml of dichloromethane were slowly added and the reaction mixture stirred at −78° C. for 10 minutes. Then, 0.680 g (2.64 mmol) trans-(4-hydroxymethyl-cyclohexylmethyl)-methyl-carbamic acid tert-butyl ester dissolved in 5.0 ml of dichloromethane were added and the reaction mixture stirred at −78° C. for 10 minutes. Subsequently, 1.84 ml of triethylamine were added at the same temperature, the reaction mixture stirred 30 minutes at −78° C., warmed to room temperature and stirred for 1 hour. It was then poured into 50 ml of an ice/water mixture and extracted 3 times with 50 ml of dichloromethane. The combined dichloromethane phases were washed with dilute hydrochloric acid, sodium hydrogen carbonate solution and with water, dried over magnesium sulfate and evaporated under reduced pressure. The residue formed was chromatographed on silica gel with a 4:1 v/v mixture of dichloromethane and ether as the eluent giving 0.615 g (91.1%) trans-(4-formyl-cyclohexylmethyl)-methyl-carbamic acid tert-butyl ester as colorless amorphous solid, MS: 273 (MNH$_4^+$).

1.3

0.590 g (2.31 mmol) trans-(4-formyl-cyclohexylmethyl)-methyl-carbamic acid tert-butyl ester, 1.325 g (2.77 mmol) 4-(bromobutyl)triphenylphosphonium bromide and 1.28 g (9.24 mmol) potassium carbonate were suspended in 10 ml of tert-amyl alcohol and the reaction mixture heated at reflux for 2 hours. It was then cooled to room temperature, diluted with ethyl acetate, filtered and evaporated under reduced pressure. The residue formed was chromatographed on silica gel with a 95:5 v/v mixture of dichloromethane and ether as the eluent giving 0.635 g (73.4%) trans-E/Z-[4-(5-bromo-pent-1-enyl)-cyclohexylmethyl]-methyl-carbamic acid tert-butyl ester as colorless viscous oil, MS: 373 (M$^+$, 1Br).

1.4

1.15 g (3.07 mmol) trans-E/Z-[4-(5-bromo-pent-1-enyl)-cyclohexylmethyl]-methyl-carbamic acid tert-butyl ester dissolved in 15 ml of ethanol were added to a suspension of 300 mg platinum dioxide freshly reduced to platinum by hydrogenation immediately prior to use. Hydrogenation was then continued at ambient pressure until 95% of the calculated amount of hydrogen had been consumed. Then, the reaction mixture was filtered over celite and evaporated giving 0.950 g (82%) trans-[4-(5-bromo-pentyl)-cyclohexylmethyl]-methyl-carbamic acid tert-butyl ester as colorless viscous oil, MS: 375 (M$^+$, 1Br).

1.5

0.950 g (2.52 mmol) trans-[4-(5-bromo-pentyl)-cyclohexylmethyl]-methyl-carbamic acid tert-butyl ester were dissolved in 6 ml of 4 N hydrogen chloride solution in dioxane and the reaction mixture stirred at room temperature for 4 hours. It was then evaporated under reduced pressure, re-suspended in tert-butyl methyl ether and filtered. There were thus obtained 0.724 g (91.7%) trans-[4-(5-bromo-pentyl)-cyclohexylmethyl]-methyl-amine hydrochloride as colorless amorphous solid, MS: 276 (MH$^+$, 1Br).

1.6

0.786 ml Diisopropyl-aethylamine, 0.619 g (2.53 mmol) 4-trifluoromethyl-benzene sulfochloride and 0.952 mg potassium carbonate (dissolved in the minimal amount of water) were added to a solution of 0.718 g (2.30 mmol) trans-[4-(5-bromo-pentyl)-cyclohexylmethyl]-methyl-amine hydrochloride in 15.0 ml of tetrahydrofuran kept at −10° C. The reaction mixture was then intensively stirred for 1 hour at −10° C. and for 1 hour at room temperature. It was subsequently evaporated, poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with dichloromethane as the eluent giving 1.03 g (92.6%) trans-N-[4-(5-bromo-pentyl)-cyclohexylmethyl]-N-methyl-4-trifluoromethyl-benzenesulfonamide as colorless amorphous solid, MS: 404 [(M−Br)$^+$].

1.7

0.515 ml Diisopropyl-aethylamine, 0.674 g (3.00 mmol) 4-trifluoromethylphenyl chloroformate [Org. Lett. (2000), 2(8), 1049–1051] and 0.828 mg potassium carbonate (dissolved in the minimal amount of water) were added to a suspension of 0.625 g (2.00 mmol) trans-[4-(5-bromo-pentyl)-cyclohexylmethyl]-methyl-amine hydrochloride in 20.0 ml of tetrahydrofuran kept at −10° C. The reaction mixture was then intensively stirred for 1 hour at −10° C. and for 3 hour at room temperature. 0.200 g 4-trifluoromethylphenyl chloroformate were added and stirring at room temperature continued for additional 2 hours. The reaction mixture was subsequently acidified with dilute hydrogen chloride solution. It was then evaporated, poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 1:1 v/v mixture of hexane and dichloromethane as the eluent giving 0.90 g (96.9%) trans-[4-(5-bromo-pentyl)-cyclohexylmethyl]-methyl-carbamic acid 4-trifluoromethyl-phenyl ester as colorless viscous oil, MS: 464 (MH$^+$, 1Br).

Example 2

2.1

153 mg (0.315 mmol) trans-N-[4-(5-bromo-pentyl)-cyclohexylmethyl]-N-methyl-4-trifluoromethylbenzenesulfonamide (example 1.6) dissolved in 2.0 ml of methanol were treated with 0.5 ml of N-allyl-methyl-amine and the reaction mixture stirred for 6 h at 50° C. It was then evaporated, poured into 50 ml of an ice/water mixture and extracted 3 times with 50 ml of dichloromethane. The combined dichloromethane phases were washed with sodium carbonate solution, dried over magnesium sulfate and evaporated under reduced pressure. The residue formed was chromatographed on silica gel with a 9:1:0.1 v/v/v mixture of dichloromethane, methanol and saturated ammonia solution as the eluent giving 0.110 g (73.3%) trans-N-{4-[5-(allyl-methyl-amino)-pentyl]-cyclohexylmethyl}-N-methyl-4-trifluoromethyl-benzenesulfonamide as colorless solid, MS: 475 (MH$^+$).

In analogy to the method described in example 2.1, alkyl bromides were treated with secondary or primary amines in methanol or N,N-dimethylacetamide to yield tertiary or secondary amine products as listed in the following table.

| Example | Product | MS MH$^+$ | Bromide | Amine |
|---|---|---|---|---|
| 2.2 | trans-N-{4-[5-(4-Hydroxy-piperidin-1-yl)-pentyl]-cyclohexylmethyl}-N-methyl-4-trifluoromethyl-benzenesulfonamide | 505 | trans-N-[4-(5-Bromo-pentyl)-cyclohexylmethyl]-N-methyl-4-trifluoromethyl-benzenesulfonamide | 4-Hydroxy-piperidine |
| 2.3 | trans-N-[4-(5-Dimethylamino-pentyl)-cyclohexylmethyl]-N-methyl-4-trifluoromethyl-benzenesulfonamide | 449 | trans-N-[4-(5-Bromo-pentyl)-cyclohexylmethyl]-N-methyl-4-trifluoromethyl-benzenesulfonamide | Dimethyl-amine |
| 2.4 | trans-N-(4-{5-[Ethyl-(2-hydroxy-ethyl)-amino]-pentyl}-cyclohexylmethyl)-N-methyl-4-trifluoromethyl-benzenesulfonamide | 493 | trans-N-[4-(5-Bromo-pentyl)-cyclohexylmethyl]-N-methyl-4-trifluoromethyl-benzenesulfonamide | Ethyl-(2-hydroxy-ethyl)-amine |
| 2.5 | trans-N-(4-{5-[Bis-(2-hydroxy-ethyl)-amino]-pentyl}-cyclohexylmethyl)-N-methyl-4-trifluoromethyl-benzenesulfonamide | 509 | trans-N-[4-(5-Bromo-pentyl)-cyclohexylmethyl]-N-methyl-4-trifluoromethyl-benzenesulfonamide | Bis-(2-hydroxy-ethyl)-amine |
| 2.6 | trans-{4-[5-(Allyl-methyl-amino)-pentyl]-cyclohexylmethyl}-methyl-carbamic acid 4-trifluoromethyl-phenyl ester | 455 | trans-[4-(5-Bromo-pentyl)-cyclohexylmethyl]-methyl-carbamic acid 4-trifluoromethyl-phenyl ester | N-Allyl-methyl-amine |
| 2.7 | trans-[4-(5-Dimethylamino-pentyl)-cyclohexylmethyl]-methyl-carbamic acid 4-trifluoromethyl-phenyl ester | 429 | trans-[4-(5-Bromo-pentyl)-cyclohexylmethyl]-methyl-carbamic acid 4-trifluoromethyl-phenyl ester | Dimethyl-amine |
| 2.8 | trans-(4-{5-[Ethyl-(2-hydroxy-ethyl)-amino]-pentyl}-cyclohexylmethyl)-methyl-carbamic acid 4-trifluoromethyl-phenyl ester | 473 | trans-[4-(5-Bromo-pentyl)-cyclohexylmethyl]-methyl-carbamic acid 4-trifluoromethyl-phenyl ester | Ethyl-(2-hydroxy-ethyl)-amine |
| 2.9 | trans-{4-[5-(4-Hydroxy-piperidin-1-yl)-pentyl]-cyclohexylmethyl}-methyl-carbamic acid 4-trifluoromethyl-phenyl ester | 485 | trans-[4-(5-Bromo-pentyl)-cyclohexylmethyl]-methyl-carbamic acid 4-trifluoromethyl-phenyl ester | 4-Hydroxy-piperidine |
| 2.10 | trans-(4-{5-[Bis-(2-hydroxy-ethyl)-amino]-pentyl}-cyclohexylmethyl)-methyl-carbamic acid 4-trifluoromethyl-phenyl ester | 489 | trans-[4-(5-Bromo-pentyl)-cyclohexylmethyl]-methyl-carbamic acid 4-trifluoromethyl-phenyl ester | Bis-(2-hydroxy-ethyl)-amine |
| 2.11 | trans-N-Methyl-N-[4-(5-piperidin-1-yl-pentyl)-cyclohexylmethyl]-4-trifluoromethyl-benzenesulfonamide | 489 | trans-N-[4-(5-Bromo-pentyl)-cyclohexylmethyl]-N-methyl-4-trifluoromethyl-benzenesulfonamide | Piperidine |

-continued

| Example | Product | MS MH+ | Bromide | Amine |
|---------|---------|--------|---------|-------|
| 2.12 | trans-N-Methyl-N-[4-(5-pyrrolidin-1-yl-pentyl)-cyclohexylmethyl]-4-trifluoromethyl-benzenesulfonamide | 475 | trans-N-[4-(5-Bromo-pentyl)-cyclohexylmethyl]-N-methyl-4-trifluoromethyl-benzenesulfonamide | Pyrrolidine |

Example 3

3.1

0.700 g (1.42 mmol) of 3-benzyloxypropyl)triphenylphosphonium bromide, 0.305 g (1.18 mmol) of trans-(4-formyl-cyclohexylmethyl)-methyl-carbamic acid tert-butyl ester (example 1.2) and 0.662 g of finely milled potassium carbonate were suspended in 10.0 ml of 2-methyl-2-butanol and the reaction mixture intensively stirred at 100° C. for 2 hours. It was then evaporated, poured into 50 ml of an ice/water mixture and extracted 3 times with 50 ml of ethylacetate. The combined ethylacetate phases were dried over magnesium sulfate and evaporated under reduced pressure. The residue formed was chromatographed on silica gel with a 95:5 v/v mixture of dichloromethane and ether as the eluent giving 0.364 g (78.6%) trans-[4-(4-benzyloxy-[E/Z 1:9]but-1-enyl)-cyclohexylmethyl]-methyl-carbamic acid tert-butyl ester as colorless viscous oil, MS: 331 [M−C$_4$H$_8$)$^+$].

3.2

0.350 g (0.903 mmol) of trans-[4-(4-benzyloxy-[E/Z 1:9]but-1-enyl)-cyclohexylmethyl]-methyl-carbamic acid tert-butyl ester were dissolved in 10.0 ml of ethylacetate. 0.3 g palladium on charcoal (5%) were added and the reaction mixture hydrogenated at normal pressure for 24 hours. Then, it was filtered over celite, evaporated and the residue formed was chromatographed on silica gel with a 4:1 v/v mixture of dichloromethane and ether as the eluent giving 0.23 g (85%) of trans-[4-(4-hydroxy-butyl)-cyclohexylmethyl]-methyl-carbamic acid tert-butyl ester as colorless viscous oil, MS: 300 (MH$^+$).

3.3

In analogy to the sequence described in examples 1.5 and 1.6 trans-[4-(4-hydroxy-butyl)-cyclohexylmethyl]-methyl-carbamic acid tert-butyl ester was treated with hydrogen chloride solution in methanol/water followed by acylation with 4-trifluoromethyl-benzenesulfochloride giving trans-N-[4-(4-hydroxy-butyl)-cyclohexylmethyl]-N-methyl-4-trifluoromethyl-benzenesulfonamide as colorless amorphous solid, MS: no MH$^+$ or M$^+$ signal; 145, 198, 209, 252 (fragments).

3.4

1.22 g (3.0 mmol) trans-N-[4-(4-hydroxy-butyl)-cyclohexylmethyl]-N-methyl-4-trifluoromethyl-benzenesulfonamide were dissolved in 4.0 ml of pyridine, cooled to −10° C. and treated with 0.687 g methanesulfochloride. The reaction mixture was then stirred at room temperature for 2 hours. It was subsequently poured into 50 ml of an ice/water/diluted hydrogen chloride mixture and extracted 3 times with 50 ml of dichloromethane. The combined dichloromethane phases were dried over magnesium sulfate and evaporated under reduced pressure giving 1.35 g (92.8%) trans-methanesulfonic acid 4-(4-{[methyl-(4-trifluoromethyl-benzenesulfonyl)-amino]-methyl}-cyclohexyl)-butyl ester as colorless solid, MS: 486 (MH$^+$).

3.5

In analogy to the reactions described in examples 1.5 and 1.7 trans-[4-(4-hydroxy-butyl)-cyclohexylmethyl]-methyl-carbamic acid tert-butyl ester (example 3.2) was treated with hydrogen chloride solution in methanol/water followed by acylation with 4-chlorophenyl chloroformate giving trans-[4-(4-hydroxy-butyl)-cyclohexylmethyl]-methyl-carbamic acid 4-chloro-phenyl ester as colorless viscous oil, MS: 354 (MH$^+$, 1Cl).

3.6

In analogy to the reaction described in example 3.4, trans-[4-(4-hydroxy-butyl)-cyclohexylmethyl]-methyl-carbamic acid 4-chloro-phenyl ester was treated with methanesulfochloride in pyridine to yield trans-methanesulfonic acid 4-(4-{[(4-chloro-phenoxycarbonyl)-methyl-amino]-methyl}-cyclohexyl)-butyl ester as colorless viscous oil, MS: 432 (MH$^+$, 1Cl).

Example 4

In analogy to the method described in example 2.1, methanesulfonic acid esters were treated with secondary or primary amines in methanol or N,N-dimethylacetamide to yield tertiary or secondary amine products as listed in the following table.

| Example | Product | MS MH+ | Methanesulfonic acid esters | Amine |
|---------|---------|--------|------------------------------|-------|
| 4.1 | trans-N-(4-{4-[Ethyl-(2-hydroxy-ethyl)-amino]-butyl}-cyclohexylmethyl)-N-methyl-4-trifluoromethyl-benzenesulfonamide | 479 | trans-Methanesulfonic acid 4-(4-{[methyl-(4-trifluoromethyl-benzenesulfonyl)-amino]-methyl}-cyclohexyl)-butyl ester | Ethyl-(2-hydroxy-ethyl)-amine |

-continued

| Example | Product | MS MH+ | Methanesulfonic acid esters | Amine |
|---|---|---|---|---|
| 4.2 | trans-N-[4-(4-Dimethylamino-butyl)-cyclohexylmethyl]-N-methyl-4-trifluoromethyl-benzenesulfonamide | 435 | trans-Methanesulfonic acid 4-(4-{[methyl-(4-trifluoromethyl-benzenesulfonyl)-amino]-methyl}-cyclohexyl)-butyl ester | Dimethyl-amine |
| 4.3 | trans-N-[4-(4-Diethylamino-butyl)-cyclohexylmethyl]-N-methyl-4-trifluoromethyl-benzenesulfonamide | 463 | trans-Methanesulfonic acid 4-(4-{[methyl-(4-trifluoromethyl-benzenesulfonyl)-amino]-methyl}-cyclohexyl)-butyl ester | Diethyl-amine |
| 4.4 | trans-N-{4-[4-(Allyl-methyl-amino)-butyl]-cyclohexylmethyl}-N-methyl-4-trifluoromethyl-benzenesulfonamide | 461 | trans-Methanesulfonic acid 4-(4-{[methyl-(4-trifluoromethyl-benzenesulfonyl)-amino]-methyl}-cyclohexyl)-butyl ester | N-Allyl-methyl-amine |
| 4.5 | trans-N-(4-{4-[Bis-(2-hydroxy-ethyl)-amino]-butyl}-cyclohexylmethyl)-N-methyl-4-trifluoromethyl-benzenesulfonamide | 495 | trans-Methanesulfonic acid 4-(4-{[methyl-(4-trifluoromethyl-benzenesulfonyl)-amino]-methyl}-cyclohexyl)-butyl ester | Bis-(2-hydroxy-ethyl)-amine |
| 4.6 | trans-{4-[4-(Allyl-methyl-amino)-butyl]-cyclohexylmethyl}-methyl-carbamic acid 4-chloro-phenyl ester | 407 (1 Cl) | trans-Methanesulfonic acid 4-(4-{[(4-chloro-phenoxycarbonyl)-methyl-amino]-methyl}-cyclohexyl)-butyl ester | N-Allyl-methyl-amine |
| 4.7 | trans-Methyl-[4-(4-piperidin-1-yl-butyl)-cyclohexylmethyl]-carbamic acid 4-chloro-phenyl ester | 421 (1 Cl) | trans-Methanesulfonic acid 4-(4-{[(4-chloro-phenoxycarbonyl)-methyl-amino]-methyl}-cyclohexyl)-butyl ester | Piperidine |
| 4.8 | trans-(4-{4-[Ethyl-(2-hydroxy-ethyl)-amino]-butyl}-cyclohexylmethyl)-methyl-carbamic acid 4-chloro-phenyl ester | 425 (1 Cl) | trans-Methanesulfonic acid 4-(4-{[(4-chloro-phenoxycarbonyl)-methyl-amino]-methyl}-cyclohexyl)-butyl ester | Ethyl-(2-hydroxy-ethyl)-amine |

Example 5

5.1

In analogy to the procedure described in examples 1.6, trans-(4-methylaminomethyl-cyclohexyl)-methanol (example 1.1) was acylated with 4-trifluoromethyl-benzene sulfochloride giving trans-N-(4-hydroxymethyl-cyclohexylmethyl)-N-methyl-4-trifluoromethyl-benzenesulfonamide as colorless solid, MS: 366 (MH+).

5.2

In analogy to the procedure described in example 3.4, trans-N-(4-hydroxymethyl-cyclohexylmethyl)-N-methyl-4-trifluoromethyl-benzenesulfonamide is treated with methanesulfonyl chloride to yield trans-methanesulfonic acid 4-{[methyl-(4-trifluoromethyl-benzenesulfonyl)-amino]-methyl}-cyclohexylmethyl ester as colorless solid, MS: 443 (M+).

5.3

In analogy to the procedure described in examples 1.7, trans-(4-methylaminomethyl-cyclohexyl)-methanol (example 1.1) was acylated with 4-chlorophenyl chloroformate [Org. Lett. (2000), 2(8), 1049–1051] giving trans-(4-hydroxymethyl-cyclohexylmethyl)-methyl-carbamic acid 4-chloro-phenyl ester as colorless viscous oil, MS: 311 (M+).

5.4

In analogy to the procedure described in example 3.4, the trans-(4-hydroxymethyl-cyclohexylmethyl)-methyl-carbamic acid 4-chloro-phenyl ester was treated with methanesulfonyl chloride to yield trans-methanesulfonic acid 4-{[(4-chloro-phenoxycarbonyl)-methyl-amino]-methyl}-cyclohexylmethyl ester as colorless viscous oil, MS: 390 (MH+).

Example 6

In analogy to the method described in example 2.1, methanesulfonic acid esters were treated with secondary or primary amines in methanol or N,N-dimethylacetamide to yield tertiary or secondary amine products as listed in the following table.

| Example | Product | MS MH+ | Methanesulfonic acid esters | Amine |
|---|---|---|---|---|
| 6.1 | trans-N-(4-Dimethylaminomethyl-cyclohexylmethyl)-N-methyl-4-trifluoromethyl-benzenesulfonamide | 393 | trans-Methanesulfonic acid 4-{[methyl-(4-trifluoromethyl-benzenesulfonyl)-amino]-methyl}-cyclohexylmethyl ester | Dimethyl-amine |
| 6.2 | trans-N-{4-[(Allyl-methyl-amino)-methyl]-cyclohexylmethyl}-N-methyl-4-trifluoromethyl-benzenesulfonamide | 419 | trans-Methanesulfonic acid 4-{[methyl-(4-trifluoromethyl-benzenesulfonyl)-amino]-methyl}-cyclohexylmethyl ester | N-Allyl-methyl-amine |
| 6.3 | trans-N-(4-{[Ethyl-(2-hydroxy-ethyl)-amino]-methyl}-cyclohexylmethyl)-N-methyl-4-trifluoromethyl-benzenesulfonamide | 437 | trans-Methanesulfonic acid 4-{[methyl-(4-trifluoromethyl-benzenesulfonyl)-amino]-methyl}-cyclohexylmethyl ester | Ethyl-(2-hydroxy-ethyl)-amine |
| 6.4 | trans-N-(4-Diethylaminomethyl-cyclohexylmethyl)-N-methyl-4-trifluoromethyl-benzenesulfonamide | 421 | trans-Methanesulfonic acid 4-{[methyl-(4-trifluoromethyl-benzenesulfonyl)-amino]-methyl}-cyclohexylmethyl ester | Dimethyl-amine |
| 6.5 | trans-N-(4-{[Bis-(2-hydroxy-ethyl)-amino]-methyl}-cyclohexylmethyl)-N-methyl-4-trifluoromethyl-benzenesulfonamide | 453 | trans-Methanesulfonic acid 4-{[methyl-(4-trifluoromethyl-benzenesulfonyl)-amino]-methyl}-cyclohexylmethyl ester | Bis-(2-hydroxy-ethyl)-amine |
| 6.6 | trans-(4-Dimethylaminomethyl-cyclohexylmethyl)-methyl-carbamic acid 4-chloro-phenyl ester | 339 (1 Cl) | trans-Methanesulfonic acid 4-{[(4-chloro-phenoxycarbonyl)-methyl-amino]-methyl}-cyclohexylmethyl ester | Dimethyl-amine |
| 6.7 | trans-{4-[(Allyl-methyl-amino)-methyl]-cyclohexylmethyl}-methyl-carbamic acid 4-chloro-phenyl ester | 365 (1 Cl) | trans-Methanesulfonic acid 4-{[(4-chloro-phenoxycarbonyl)-methyl-amino]-methyl}-cyclohexylmethyl ester | N-Allyl-methyl-amine |
| 6.8 | trans-(4-Diethylaminomethyl-cyclohexylmethyl)-methyl-carbamic acid 4-chloro-phenyl ester | 367 (1 Cl) | trans-Methanesulfonic acid 4-{[(4-chloro-phenoxycarbonyl)-methyl-amino]-methyl}-cyclohexylmethyl ester | Dimethyl-amine |
| 6.9 | trans-(4-{[Ethyl-(2-hydroxy-ethyl)-amino]-methyl}-cyclohexylmethyl)-methyl-carbamic acid 4-chloro-phenyl ester | 383 (1 Cl) | trans-Methanesulfonic acid 4-{[(4-chloro-phenoxycarbonyl)-methyl-amino]-methyl}-cyclohexylmethyl ester | Ethyl-(2-hydroxy-ethyl)-amine |
| 6.10 | trans-(4-{[Bis-(2-hydroxy-ethyl)-amino]-methyl}-cyclohexylmethyl)-methyl-carbamic acid 4-chloro-phenyl ester | 399 (1 Cl) | trans-Methanesulfonic acid 4-{[(4-chloro-phenoxycarbonyl)-methyl-amino]-methyl}-cyclohexylmethyl ester | Bis-(2-hydroxy-ethyl)-amine |
| 6.11 | trans-N-(4-Ethylaminomethyl-cyclohexylmethyl)-N-methyl-4-trifluoromethyl-benzenesulfonamide | 393 | trans-Methanesulfonic acid 4-{[methyl-(4-trifluoromethyl-benzenesulfonyl)-amino]-methyl}-cyclohexylmethyl ester | Ethylamine |
| 6.12 | trans-N-Methyl-N-(4-piperidin-1-ylmethyl-cyclohexylmethyl)-4-trifluoromethyl-benzenesulfonamide | 433 | trans-Methanesulfonic acid 4-{[methyl-(4-trifluoromethyl-benzenesulfonyl)-amino]-methyl}-cyclohexylmethyl ester | Piperidine |

-continued

| Example | Product | MS MH+ | Methanesulfonic acid esters | Amine |
|---|---|---|---|---|
| 6.13 | trans-N-(4-Azetidin-1-ylmethyl-cyclohexylmethyl)-N-methyl-4-trifluoromethyl-benzenesulfonamide | 405 | trans-Methanesulfonic acid 4-{[methyl-(4-trifluoromethyl-benzenesulfonyl)-amino]-methyl}-cyclohexylmethyl ester | Azetidine |
| 6.14 | trans-N-Methyl-N-(4-pyrrolidin-1-ylmethyl-cyclohexylmethyl)-4-trifluoromethyl-benzenesulfonamide | 419 | trans-Methanesulfonic acid 4-{[methyl-(4-trifluoromethyl-benzenesulfonyl)-amino]-methyl}-cyclohexylmethyl ester | Pyrrolidine |
| 6.15 | trans-Methyl-(4-piperidin-1-ylmethyl-cyclohexylmethyl)-carbamic acid 4-chloro-phenyl ester | 379 (1 Cl) | trans-Methanesulfonic acid 4-{[(4-chloro-phenoxycarbonyl)-methyl-amino]-methyl}-cyclohexylmethyl ester | Piperidine |
| 6.16 | trans-Methyl-(4-pyrrolidin-1-ylmethyl-cyclohexylmethyl)-carbamic acid 4-chloro-phenyl ester | 365 (1 Cl) | trans-Methanesulfonic acid 4-{[(4-chloro-phenoxycarbonyl)-methyl-amino]-methyl}-cyclohexylmethyl ester | Pyrrolidine |

Example 7

7.1

0.532 g (1.59 mmol) of methyl (triphenylphosphoranylidene)acetate and 0.370 g (1.45 mmol) of trans-(4-formyl-cyclohexylmethyl)-methyl-carbamic acid tert-butyl ester (example 1.2) were suspended in 10.0 ml of toluene and the reaction mixture heated at 90° C. for 1 hour. It was then evaporated and the residue formed was chromatographed on silica gel with a 9:1 v/v mixture of dichloromethane and ether as the eluent giving 0.370 g (82%) trans-3-{4-[(tert-butoxycarbonyl-methyl-amino)-methyl]-cyclohexyl}-(E,Z)-acrylic acid methyl ester (E:Z=9:1) as colorless viscous oil, MS: 312 (MH+).

7.2

1.17 g (3.75 mmol) of trans-3-{4-[(tert-butoxycarbonyl-methyl-amino)-methyl]-cyclohexyl}-(E,Z)-acrylic acid methyl ester (E:Z=9:1) were dissolved in 15.0 ml of ethylacetate. 2 times 0.3 g palladium on charcoal (5%) were then added and the reaction mixture hydrogenated at normal pressure until the consumption of hydrogen came to an end. Then, it was filtered over celite, evaporated and the residue formed was chromatographed on silica gel with a 95:5 v/v mixture of dichloromethane and ether as the eluent giving 1.00 g (84.9%) of trans-3-{4-[(tert-butoxycarbonyl-methyl-amino)-methyl]-cyclohexyl}-propionic acid methyl ester as colorless viscous oil, MS: 313 (M+).

7.3

0.990 g (3.16 mmol) trans-3-{4-[(tert-butoxycarbonyl-methyl-amino)-methyl]-cyclohexyl}-propionic acid methyl ester and 660 mg potassium hydroxide were dissolved in 5.0 ml of ethanol and the reaction mixture heated at reflux for 3 hours. It was then evaporated, subsequently poured into 50 ml of an ice/water mixture, acidified with aqueous hydrochloric acid to pH 5 and extracted 3 times with 50 ml of dichloromethane. The combined dichloromethane phases were dried over magnesium sulfate and evaporated under reduced pressure giving 0.900 g (95%) trans-3-{4-[(tert-butoxycarbonyl-methyl-amino)-methyl]-cyclohexyl}-propionic acid as colorless viscous oil, MS: 299 (M+).

7.4

0.898 g (3.0 mmol) of trans-3-{4-[(tert-butoxycarbonyl-methyl-amino)-methyl]-cyclohexyl}-propionic acid dissolved in 10.0 ml of tetrahydrofuran were added slowly and at 0° C. to 4.5 ml of an 1M solution of boran-tetrahydrofuran-complex in tetrahydrofuran. The reaction mixture was then stirred at room temperature for 1 hour. Subsequently, 10 ml of methanol were added and the reaction mixture evaporated. It was then poured into 50 ml of an ice/water/aqueous sodium hydrogen carbonate mixture and extracted 3 times with 50 ml of dichloromethane. The combined dichloromethane phases were dried over magnesium sulfate and evaporated under reduced pressure. The residue formed was chromatographed on silica gel with a 4:1 v/v mixture of dichloromethane and ether as the eluent giving 0.690 g (80.6%) trans-[4-(3-hydroxy-propyl)-cyclohexylmethyl]-methyl-carbamic acid tert-butyl ester as colorless viscous oil, MS: 286 (MH+).

7.5

In analogy to the sequence described in examples 1.5 and 1.6, trans-[4-(3-hydroxy-propyl)-cyclohexylmethyl]-methyl-carbamic acid tert-butyl ester was treated with hydrogen chloride solution in methanol/water followed by acylation with 4-trifluoromethyl-benzenesulfochloride to yield trans-N-[4-(3-hydroxy-propyl)-cyclohexylmethyl]-N-methyl-4-trifluoromethyl-benzenesulfonamide as colorless solid, MS: 393 (M+).

7.6

In analogy to the procedure described in example 3.4, trans-N-[4-(3-hydroxy-propyl)-cyclohexylmethyl]-N-methyl-4-trifluoromethyl-benzenesulfonamide was treated with methanesulfonyl chloride to yield trans-methanesulfonic acid 3-(4-{[methyl-(4-trifluoromethyl-benzenesulfonyl)-amino]-methyl}-cyclohexyl)-propyl ester as colorless solid, MS: 472 (M+).

7.7

In analogy to the sequence described in examples 1.5 and 1.6, trans-[4-(3-hydroxy-propyl)-cyclohexylmethyl]-methyl-carbamic acid tert-butyl ester was treated with hydrogen chloride solution in methanol/water followed by acylation with 4-chlorophenyl chloroformate [Org. Lett. (2000), 2(8), 1049–1051] to yield trans-[4-(3-hydroxy-propyl)-cyclohexylmethyl]-methyl-carbamic acid 4-chloro-phenyl ester as colorless viscous oil, MS: 340 (MH+, 1Cl).

7.8

In analogy to the procedure described in example 3.4, trans-[4-(3-hydroxy-propyl)-cyclohexylmethyl]-methyl-carbamic acid 4-chloro-phenyl ester was treated with methanesulfonyl chloride to yield trans-methanesulfonic acid 3-(4-{[(4-chloro-phenoxycarbonyl)-methyl-amino]-methyl}-cyclohexyl)-propyl ester as colorless solid, MS: 418 (MH$^+$, 1Cl).

Example 8

In analogy to the method described in example 2.1, methanesulfonic acid esters were treated with secondary or primary amines in methanol or N,N-dimethylacetamide to yield tertiary or secondary amine products as listed in the following table.

| Example | Product | MS MH$^+$ | Methanesulfonic acid esters | Amine |
|---|---|---|---|---|
| 8.1 | trans-N-{4-[3-(Allyl-methyl-amino)-propyl]-cyclohexylmethyl}-N-methyl-4-trifluoromethyl-benzenesulfonamide | 447 | trans-Methanesulfonic acid 3-(4-{[methyl-(4-trifluoromethyl-benzenesulfonyl)-amino]-methyl}-cyclohexyl)-propyl ester | N-Allyl-methyl-amine |
| 8.2 | trans-N-(4-{3-[Ethyl-(2-hydroxy-ethyl)-amino]-propyl}-cyclohexylmethyl)-N-methyl-4-trifluoromethyl-benzenesulfonamide | 465 | trans-Methanesulfonic acid 3-(4-{[methyl-(4-trifluoromethyl-benzenesulfonyl)-amino]-methyl}-cyclohexyl)-propyl ester | Ethyl-(2-hydroxy-ethyl)-amine |
| 8.3 | trans-N-[4-(3-Allylamino-propyl)-cyclohexylmethyl]-N-methyl-4-trifluoromethyl-benzenesulfonamide | 433 | trans-Methanesulfonic acid 3-(4-{[methyl-(4-trifluoromethyl-benzenesulfonyl)-amino]-methyl}-cyclohexyl)-propyl ester | N-Allyl-amine |
| 8.4 | trans-N-Methyl-N-[4-(3-methylamino-propyl)-cyclohexylmethyl]-4-trifluoromethyl-benzenesulfonamide | 407 | trans-Methanesulfonic acid 3-(4-{[methyl-(4-trifluoromethyl-benzenesulfonyl)-amino]-methyl}-cyclohexyl)-propyl ester | Methylamine |
| 8.5 | trans-{4-[3-(Allyl-methyl-amino)-propyl]-cyclohexylmethyl}-methyl-carbamic acid 4-chloro-phenyl ester | 393 (1 Cl) | trans-Methanesulfonic acid 3-(4-{[(4-chloro-phenoxycarbonyl)-methyl-amino]-methyl}-cyclohexyl)-propyl ester | N-Allyl-methyl-amine |
| 8.6 | trans-Methyl-[4-(3-piperidin-1-yl-propyl)-cyclohexylmethyl]-carbamic acid 4-chloro-phenyl ester | 407 1 Cl | trans-Methanesulfonic acid 3-(4-{[(4-chloro-phenoxycarbonyl)-methyl-amino]-methyl}-cyclohexyl)-propyl ester | Piperidine |
| 8.7 | trans-(4-{3-[Ethyl-(2-hydroxy-ethyl)-amino]-propyl}-cyclohexylmethyl)-methyl-carbamic acid 4-chloro-phenyl ester | 411 1 Cl | trans-Methanesulfonic acid 3-(4-{[(4-chloro-phenoxycarbonyl)-methyl-amino]-methyl}-cyclohexyl)-propyl ester | Ethyl-(2-hydroxy-ethyl)-amine |
| 8.8 | trans-(4-{3-[Bis-(2-hydroxy-ethyl)-amino]-propyl}-cyclohexylmethyl)-methyl-carbamic acid 4-chloro-phenyl ester | 427 (1 Cl) | trans-Methanesulfonic acid 3-(4-{[(4-chloro-phenoxycarbonyl)-methyl-amino]-methyl}-cyclohexyl)-propyl ester | Bis-(2-hydroxy-ethyl)-amine |

Example 9

9.1

2.1 g (13.35 mmol) trans-(4-methylaminomethyl-cyclohexyl)-methanol (example 1.1) were dissolved in 20 ml methanol. 3.32 g (13.35 mmol) N-(benzyloxycarbonyloxy)-succinimide were added and the solution was stirred at room temperature for 2 hours, then for 1 hour at 50° C. Afterwards, the solvent was evaporated under reduced pressure and the residue was partitioned between dichloromethane and water. The organic phase was washed with water (2 times), then with brine and finally dried over magnesium sulfate and evaporated under reduced pressure. The residue was chromatographed on silica gel with a 4:1 v/v mixture of dichloromethane and diethyl ether as the eluent. 1.67 g (42.9%) trans-(4-hydroxymethyl-cyclohexylmethyl)-methyl-carbamic acid benzyl ester were obtained as colorless oil, M: 289 (M).

9.2

In analogy to the method described in example 1.2, 1.65 g (5.66 mmol) of trans-(4-hydroxymethylcyclohexylmethyl)-methyl-carbamic acid benzyl ester were treated with dimethylsulfoxide/triethylamine in dichloromethane between −78° C. and room temperature to yield 1.6 g (97.6%) trans-(4-formyl-cyclohexylmethyl)-methyl-carbamic acid benzyl ester as colorless oil, MS: 289 (M).

9.3

2.27 g (6.63 mmol) (methoxymethyl) triphenylphosphonium chloride were suspended in 20 ml of absolute tetrahydrofuran, the temperature being maintained at −10° C. 0.75 g (6.63 mmol) of potassium tert.-butylate were added while stirring, thus a homogenous solution was obtained. After 0.5 hour, 1.6 g (5.52 mmol) trans-(4-formyl-cyclohexylmethyl)-methyl-carbamic acid benzyl ester dissolved in 10 ml of tetrahydrofuran were added, and stirring was continued for 2 hours at −10° C., then for 1 hour at room temperature. Afterwards, the solvent was evaporated under reduced pressure, the residue was dissolved in 3 ml of dichloromethane and then chromatographed on silica gel with a 98:2 v/v mixture of dichloromethane and diethyl ether as the eluent, yielding 0.81 g (42.9%) trans-[4-(E,Z)-(2-methoxy-vinyl)-cyclohexylmethyl]-methyl-carbamic acid benzyl ester as colorless oil, M: 318 (MH$^+$).

9.4

0.8 g (2.52 mmol) trans-[4-(E,Z)-(2-methoxy-vinyl)-cyclohexylmethyl]-methyl-carbamic acid benzyl ester were dissolved in 10 ml of tetrahydrofuran; 1 ml of a 2N aqueous hydrochloric acid solution was added and the mixture was heated to reflux for 2 hours. Then, the reaction mixture was neutralized by addition of aqueous sodium bicarbonate solution and extracted with dichloromethane. The organic phase was washed with brine, then dried over magnesium sulfate and evaporated under reduced pressure. Trans-methyl-[4-(2-oxo-ethyl)-cyclohexylmethyl]-carbamic acid benzyl ester was obtained in quantitative yield as colorless, viscous oil, M: 304 (MH$^+$).

9.5

A stirred solution of 0.75 g (2.47 mmol) trans-methyl-[4-(2-oxo-ethyl)-cyclohexylmethyl]-carbamic acid benzyl ester in 15 ml of methanol was cooled to 0–5° C. 0.14 g (3.7 mmol) of sodium borohydride were added in four equal portions, at intervals of 10 minutes. Stirring was continued for 1 hour at room temperature. Afterwards, a 1N aqueous hydrochloric acid solution was dropped into the solution until the medium was acidic; it was then made neutral by addition of aqueous sodium bicarbonate solution. The reaction mixture was subsequently extracted 3 times with 25 ml of dichloromethane. The combined organic phases were dried over magnesiumsulfate and evaporated under reduced pressure. The residue obtained was chromatographed on silica gel with a 95:5 v/v mixture of dichloromethane and methanol as the eluent. 0.63 g (83%) trans-[4-(2-hydroxy-ethyl)-cyclohexylmethyl]-methyl-carbamic acid benzyl ester were obtained as colorless oil, MS: 306 (MH$^+$).

9.6

0.62 g (2.03 mmol) trans-[4-(2-hydroxy-ethyl)-cyclohexylmethyl]-methyl-carbamic acid benzyl ester dissolved in 10 ml of tetrahydrofuran were submitted to a hydrogenation over 0.3 g of 5% palladium on charcoal as catalyst, at normal pressure and ambient temperature. The cleavage of the benzyloxycarbonyl group was complete after 3 hours. After removal of the catalyst by filtration and evaporation of the solvent, 0.33 g (95%) of trans-2-(4-methylaminomethyl-cyclohexyl)-ethanol were obtained as a colorless oil, MS: 172 (MH$^+$).

9.7

In analogy to the procedure described in example 1.7, 0.325 g (1.90 mmol) of trans-2-(4-methylaminomethyl-cyclohexyl)-ethanol were acylated with 0.54 g (2.84 mmol) of 4-chlorophenyl chloroformate to yield 0.34 g (55%) trans-[4-(2-hydroxy-ethyl)-cyclohexylmethyl]-methyl-carbamic acid 4-chloro-phenyl ester as colorless viscous oil, MS: 326 (MH$^+$, 1Cl).

9.8

In analogy to the procedure described in example 3.4, trans-[4-(2-hydroxy-ethyl)-cyclohexylmethyl]-methyl-carbamic acid 4-chloro-phenyl ester was treated with methanesulfonyl chloride to yield trans-methanesulfonic acid 2-(4-{[(4-chloro-phenoxycarbonyl)-methyl-amino]-methyl}-cyclohexyl)-ethyl ester as colorless viscous oil, MS: 404 (MH$^+$, 1Cl).

9.9

In analogy to the procedure described in example 1.6, trans-2-(4-methylaminomethyl-cyclohexyl)-ethanol was acylated with 4-trifluoromethyl-benzene sulfochloride to yield trans-N-[4-(2-hydroxy-ethyl)-cyclohexylmethyl]-N-methyl-4-trifluoromethyl-benzenesulfonamide as colorless solid, MS: 380 (MH$^+$).

9.10

In analogy to the procedure described in example 3.4, trans-N-[4-(2-hydroxy-ethyl)-cyclohexylmethyl]-N-methyl-4-trifluoromethyl-benzenesulfonamide was treated with methanesulfonyl chloride to yield trans-methanesulfonic acid 2-(4-{[methyl-(4-trifluoromethyl-benzenesulfonyl)-amino]-methyl}-cyclohexyl)-ethyl ester as colorless solid, MS: 358 (MH$^+$).

Example 10

In analogy to the method described in example 2.1, methanesulfonic acid esters were treated with secondary or primary amines in methanol or N,N-dimethylacetamide to yield tertiary or secondary amine products as listed in the following table.

| Example | Product | MS MH$^+$ | Methanesulfonic acid esters | Amine |
| --- | --- | --- | --- | --- |
| 10.1 | trans-{4-[2-(Allyl-methyl-amino)-ethyl]-cyclohexylmethyl}-methyl-carbamic acid 4-chloro-phenyl ester | 379 (1 Cl) | trans-Methanesulfonic acid 2-(4-{[(4-chloro-phenoxycarbonyl)-methyl-amino]-methyl}-cyclohexyl)-ethyl ester | N-Allyl-methyl-amine |

-continued

| Example | Product | MS MH+ | Methanesulfonic acid esters | Amine |
|---|---|---|---|---|
| 10.2 | trans-Methyl-[4-(2-piperidin-1-yl-ethyl)-cyclohexylmethyl]-carbamic acid 4-chloro-phenyl ester | 393 (1 Cl) | trans-Methanesulfonic acid 2-(4-{[(4-chloro-phenoxycarbonyl)-methyl-amino]-methyl}-cyclohexyl)-ethyl ester | Piperidine |
| 10.3 | trans-N-Methyl-N-[4-(2-piperidin-1-yl-ethyl)-cyclohexylmethyl]-4-trifluoromethyl-benzenesulfonamide | 447 | trans-Methanesulfonic acid 2-(4-{[methyl-(4-trifluoromethyl-benzenesulfonyl)-amino]-methyl}-cyclohexyl)-ethyl ester | Piperidine |
| 10.4 | trans-N-(4-{2-[Ethyl-(2-hydroxy-ethyl)-amino]-ethyl}-cyclohexylmethyl)-N-methyl-4-trifluoromethyl-benzenesulfonamide | 451 | trans-Methanesulfonic acid 2-(4-{[methyl-(4-trifluoromethyl-benzenesulfonyl)-amino]-methyl}-cyclohexyl)-ethyl ester | Ethyl-(2-hydroxy-ethyl)-amine |
| 10.5 | trans-N-(4-{2-[Bis-(2-hydroxy-ethyl)-amino]-ethyl}-cyclohexylmethyl)-N-methyl-4-trifluoromethyl-benzenesulfonamide | 467 | trans-Methanesulfonic acid 2-(4-{[methyl-(4-trifluoromethyl-benzenesulfonyl)-amino]-methyl}-cyclohexyl)-ethyl ester | Bis-(2-hydroxy-ethyl)-amine |
| 10.6 | trans-(4-{2-[Ethyl-(2-hydroxy-ethyl)-amino]-ethyl}-cyclohexylmethyl)-methyl-carbamic acid 4-chloro-phenyl ester | 397 (1 Cl) | trans-Methanesulfonic acid 2-(4-{[(4-chloro-phenoxycarbonyl)-methyl-amino]-methyl}-cyclohexyl)-ethyl ester | Ethyl-(2-hydroxy-ethyl)-amine |
| 10.7 | trans-N-{4-[2-(Allyl-methyl-amino)-ethyl]-cyclohexylmethyl}-N-methyl-4-trifluoromethyl-benzenesulfonamide | 433 | trans-Methanesulfonic acid 2-(4-{[methyl-(4-trifluoromethyl-benzenesulfonyl)-amino]-methyl}-cyclohexyl)-ethyl ester | N-Allyl-methyl-amine |
| 10.8 | trans-(RS,RS)-N-(4-{2-[Bis-(2-hydroxy-propyl)-amino]-ethyl}-cyclohexylmethyl)-N-methyl-4-trifluoromethyl-benzenesulfonamide | 495 | trans-Methanesulfonic acid 2-(4-{[methyl-(4-trifluoromethyl-benzenesulfonyl)-amino]-methyl}-cyclohexyl)-ethyl ester | Bis-(2-hydroxy-propyl)-amine |

Example 11

11.1

To a dry-ice cooled solution of 30.0 g (208 mmol) trans-(4-hydroxymethyl-cyclohexyl)-methanol in 450 ml tetrahydrofuran was dropped at −60° C. to −67° C., within 30 minutes, 130 ml (208 mmol) 1.6 M butyllithium solution (1.6 M in hexane). After stirring for 30 minutes at −78° C., 32.3 g (208 mmol) of tert-butyl-dimethyl-chlorosilane was added within 10 minutes. After stirring the reaction mixture for 15 minutes at −65° C., it was stirred over night at room temperature and then partitioned between ether, 1N hydrogen chloride solution and water. The organic layer was dried over magnesium sulfate, concentrated under reduced pressure and the residue then chromatographed on silica gel with a 3:1 v/v mixture of hexane and ethylacetate as the eluent giving 27.7 g (51.4%) of pure trans-[4-(tert-butyl-dimethyl-silanyloxymethyl)-cyclohexyl]-methanol as colorless viscous oil, MS: 259 (MH+).

11.2

To an ice-cooled solution of 27.6 g (107 mmol) trans-[4-(tert-butyl-dimethyl-silanyloxymethyl)-cyclohexyl]-methanol and 9.99 ml (128 mmol) of methanesulfonyl chloride in 350 ml of dichloromethane was added under stirring at 0–10° C. 29.6 ml (213 mmol) triethylamine within 20 minutes. The reaction-mixture was then stirred for 1 hour at room temperature. It was then partitioned between dichloromethane, 1N HCl and water. The dichloromethane-phase was dried over magnesium sulfate and concentrated to yield 38.2 g crude trans-methanesulfonic acid 4-(tert-butyl-dimethyl-silanyloxymethyl)-cyclohexylmethyl ester as colorless viscous oil, MS: 354 (M+NH$_4^+$).

11.3

38.2 g of crude trans-methanesulfonic acid 4-(tert-butyl-dimethyl-silanyloxymethyl)-cyclohexylmethyl ester and 16.7 g (340 mmol) of sodium cyanide dissolved in 380 ml of N,N-dimethylformamide were stirred for 2 hours at 80° C. After cooling the reaction mixture down to room temperature, it was partitioned between ether and water. The organic layer was dried over magnesium sulfate and concentrated under reduced pressure and the residue then chromatographed on silica gel with a 9:1 v/v mixture of hexane and ethylacetate as the eluent giving 24.2 g (79.7% over two steps) of pure trans-[4-(tert-butyl-dimethyl-silanyloxymethyl)-cyclohexyl]-acetonitrile as colorless viscous oil, MS: 290 (MNa+).

11.4

A solution of 24.2 g (90.5 mmol) trans-[4-(tert-butyl-dimethyl-silanyloxymethyl)-cyclohexyl]-acetonitrile, of 22 ml (270 mmol) chloroform and of 2.4 g platinum dioxide (Degussa 223) in 250 ml ethanol was stirred at room temperature for 20 hours under a hydrogen atmosphere. The catalyst was then removed by filtration and the solvent evaporated under reduced pressure giving 17.1 g (97.3%) of pure trans-[4-(2-amino-ethyl)-cyclohexyl]-methanol HCl-salt as colorless solid, MS: 158 (MH$^+$).

11.5

To a solution of 17.6 g (90.9 mmol) trans-[4-(2-amino-ethyl)-cyclohexyl]-methanol HCl-salt and 13.9 ml (100 mmol) triethylamine in 120 ml dichloromethane was added under stirring within 10 minutes at room temperature a solution of 21.8 g (100 mmol) of di-tert-butyl-dicarbonate in 70 ml of dichloromethane. After stirring for 3 hours at room temperature, the reaction-mixture was partitioned between dichloromethane, 1N hydrogen chloride solution and water. Then, the dichloromethane-phase was dried over magnesium sulfate and concentrated to yield 27.9 of crude trans-[2-(4-hydroxymethyl-cyclohexyl)-ethyl]-carbamic acid tert-butyl ester as colorless viscous oil, MS: 275 (MNH$_4^+$).

11.6

A solution of 27.9 g (86.7 mmol) trans-[2-(4-hydroxymethyl-cyclohexyl)-ethyl]-carbamic acid tert-butyl ester, 41 ml (434 mmol) acetic anhydride and 35 ml (434 mmol) of pyridine in 140 ml of dichloromethane was stirred at room temperature for 16 hours. The reaction-mixture was then taken up in ether and washed with 1N hydrogen chloride solution, sodium hydrogen carbonate solution and water. Then, the ether-phase was dried over magnesium sulfate and concentrated to yield 26.0 g crude trans-acetic acid 4-(2-tert-butoxycarbonylamino-ethyl)-cyclohexylmethyl ester as colorless viscous oil, MS: 200 [(M-(tert-butoxycarbonyl))H$^+$].

11.7

To an ice-cooled and stirred solution of the crude 26.0 g trans-acetic acid 4-(2-tert-butoxycarbonylamino-ethyl)-cyclohexylmethyl ester and 5.77 ml (92.6 mmol) methyliodide in 300 ml of N,N-dimethylformamide was added within 15 minutes 4.04 g (92.58 mmol) sodium hydride (55% in oil). After stirring over night at room temperature, additional 1.65 ml (26.5 mmol) methyliodide and 1.16 g (26.5 mmol) of sodium hydride were added and the reaction-mixture was then stirred for another 1 hour at room temperature. It was then partitioned between ether, 1N hydrogen chloride solution and water. The organic layer was dried over magnesium sulfate and concentrated under reduced pressure and the residue then chromatographed on silica gel with a 4:1 v/v mixture of hexane and ethylacetate as the eluent giving 18.7 g (67.7% over 3 steps) of pure trans-acetic acid 4-[2-(tert-butoxycarbonyl-methyl-amino)-ethyl]-cyclohexylmethyl ester as colorless viscous oil, MS: 214 [(M-(tert-butoxycarbonyl))H$^+$].

11.8

To a solution of 18.7 g (59.7 mmol) of trans-acetic acid 4-[2-(tert-butoxycarbonyl-methyl-amino)-ethyl]-cyclohexylmethyl ester in 110 ml of methanol was added 41.25 g (298.5 mmol) of potassium carbonate. The reaction mixture was then stirred for 2 hours at room temperature. The excess of potassium carbonate was removed by filtration and the methanol was removed by evaporation under reduced pressure. The crude residue was partitioned between ether, 1N hydrogen chloride solution and water. The organic layer was dried over magnesium sulfate and concentrated under reduced pressure and the residue then chromatographed on silica gel with a 2:1 v/v mixture of hexane and ethylacetate as the eluent giving 13.9 g (86.0%) of pure trans-[2-(4-hydroxymethyl-cyclohexyl)-ethyl]-methyl-carbamic acid tert-butyl ester as colorless viscous oil, MS 272 (MH$^+$).

11.9

1.56 ml (18.2 mmol) of oxalylchloride were added to a dry-ice-cooled solution of 2 ml (28 mmol) of dimethylsulfoxide in 30 ml dichloromethane at −78° C. After stirring for 15 minutes at −78° C., a solution of 3.8 g (14 mmol) trans-2-(4-hydroxymethyl-cyclohexyl)-ethyl]-methyl-carbamic acid tert-butyl ester in 10 ml of dichloromethane was added within 10 minutes at −78° C. to the reaction mixture. After stirring for 15 minutes under dry-ice-cooling, 9.76 ml (70 mmol) of triethylamine was added. The dry ice-cooling was then removed and the reaction mixture was stirred for further 3 hours at room temperature. It was then taken up in ether and washed with 1N hydrogen chloride solution and water. The organic layer was dried over magnesium sulfate and concentrated under reduced pressure giving 4.02 g of crude trans-[2-(4-formyl-cyclohexyl)-ethyl]-methyl-carbamic acid tert-butyl ester as colorless viscous oil, MS: 269 (M$^+$).

11.10

A solution of 4.02 g (14.9 mmol) trans-[2-(4-formyl-cyclohexyl)-ethyl]-methyl-carbamic acid tert-butyl ester and 5.47 g (14.9 mmol) of (triphenyl-phosphoranylidene)-acetic acid ethyl ester in 40 ml of dichloromethane was stirred at room temperature for 60 hours. After concentration under reduced pressure, the crude product was chromatographed on silica gel with a 9:1 v/v mixture of hexane and ethylacetate as the eluent giving 3.82 g (75.4%) of pure trans-3-{4-[2-(tert-butoxycarbonyl-methyl-amino)-ethyl]-cyclohexyl}-(E)-acrylic acid ethyl ester as colorless viscous oil, MS: 340 (MH$^+$).

11.11

A suspension of 3.8 g (11.2 mmol) trans-3-{4-[2-(tert-butoxycarbonyl-methyl-amino)-ethyl]-cyclohexyl}-(E)-acrylic acid ethyl ester and 400 mg of palladium (10% on carbon) in 40 ml of methanol was stirred for 20 hours at room temperature under a hydrogen atmosphere. The catalyst was removed by filtration and the solvent evaporated under reduced pressure to give 3.67 g of crude trans-3-{4-[2-(tert-butoxycarbonyl-methyl-amino)-ethyl]-cyclohexyl}-propionic acid ethyl ester as colorless viscous oil, MS: 359 (MNH$_4^+$).

11.12

To a solution of trans-3-{4-[2-(tert-butoxycarbonyl-methyl-amino)-ethyl]-cyclohexyl}-propionic acid ethyl ester in 40 ml of tetrahydrofuran was added under ice-cooling 547 mg (14.0 mmol) of lithium aluminium hydride in small portions. The reaction mixture was then stirred for 1 hour at room temperature. To destroy the excess of lithium aluminium hydride, 50 ml of brine was added to the reaction mixture under ice-cooling. It was then partitioned between ether and water, the organic layer was dried over magnesium sulfate and concentrated under reduced pressure giving 3.35 g (100% over 2 stepts) nearly pure trans-{2-[4-(3-hydroxy-propyl)-cyclohexyl]-ethyl}-methyl-carbamic acid tert-butyl ester as colorless viscous oil, MS. 317 (MNH$_4^+$).

11.13

To a solution of 3.35 g (11.20 mmol) trans-{2-[4-(3-hydroxy-propyl)-cyclohexyl]-ethyl}-methyl-carbamic acid tert-butyl ester and 1.54 ml (13.4 mmol) of methanesulfonyl chloride in 35 ml dichloromethane was added under ice-cooling within 5 minutes a solution of 1.87 ml (13.4 mmol) triethylamine in 5 ml of dichloromethane. The reaction mixture was then stirred for 1 hour at room temperature. It was subsequently partitioned between ether, water and 1N hydrogen chloride solution. The organic layer was dried over magnesium sulfate and concentrated under reduced pressure giving 4.06 g (96.1%) almost pure trans-methanesulfonic acid 3-{4-[2-(tert-butoxycarbonyl-methyl-amino)-ethyl]-cyclohexyl}-propyl ester as colorless viscous oil, MS: 395 (MNH$_4^+$).

11.14

30 ml of 4N hydrogen chloride solution in dioxan was added to 4.06 g (10.8 mmol) of trans methanesulfonic acid 3-{4-[2-(tert-butoxycarbonyl-methyl-amino)-ethyl]-cyclohexyl}-propyl ester. After stirring of the reaction mixture for 3 hours at room temperature, it was concentrated under reduced pressure. The residue formed was stirred in ether and the crystals formed were filtered off and washed with ether. After drying under reduced pressure and at and 45° C., 3.12 g (92.4%) trans-methanesulfonic acid 3-[4-(2-methylamino-ethyl)-cyclohexyl]-propyl ester HCl salt could be isolated as colorless crystals, MS: 278 (MH$^+$).

11.15

To an ice-cooled solution of 1.5 g (4.78 mmol) of trans-methanesulfonic acid 3-[4-(2-methylamino-ethyl)-cyclohexyl]-propyl ester HCl salt and 1.23 g (5.5 mmol) of 4-trifluoromethyl-phenyl-chloroformate in 30 ml of dichloromethane was added 4.06 ml (23.9 mmol) of diisopropyl ethylamine. The reaction mixture was then stirred for 1 hour at room temperature and partitioned between ether, 1N hydrogen chloride solution and water. The organic layer was dried over magnesium sulfate and concentrated under reduced pressure and the residue then chromatographed on silica gel with a 2:1 v/v mixture of hexane and ethylacetate as the eluent giving 1.94 g (87.2%) trans-methanesulfonic acid 3-(4-{2-[methyl-(4-trifluoromethyl-phenoxycarbonyl)-amino]-ethyl}-cyclohexyl)-propyl ester as colorless viscous oil, MS: 466 (MH$^+$).

11.16

In analogy to the procedure described in example 11.15, trans-methanesulfonic acid 3-[4-(2-methylamino-ethyl)-cyclohexyl]-propyl ester HCl salt was reacted with 4-chloro-phenyl-chloroformate to yield trans-methanesulfonic acid 3-(4-{2-[(4-chloro-phenoxycarbonyl)-methyl-amino]-ethyl}-cyclohexyl)-propyl ester as colorless viscous oil, MS: 432 (MH$^+$, 1 Cl).

Example 12

12.1

A solution of 200 mg (0.43 mmol) trans-methanesulfonic acid 3-(4-{2-[methyl-(4-trifluoromethyl-phenoxycarbonyl)-amino]-ethyl}-cyclohexyl)-propyl ester and 0.204 ml (2.15 mmol) of allyl methyl amine in 2 ml of N,N-dimethylacetamide was stirred over night at 60° C. The reaction mixture was then taken up in ether and the ether phases were washed with water. The organic layer was dried over magnesium sulfate, concentrated under reduced pressure and the residue then chromatographed on silica gel with a 9:1 v/v mixture of dichloromethane and 1N ammonia in methanol as the eluent giving 124 mg (65.5%) trans-(2-{4-[3-(allyl-methyl-amino)-propyl]-cyclohexyl}-ethyl)-methyl-carbamic acid 4-trifluoromethyl-phenyl ester as colorless viscous oil, MS: 441 (MH$^+$).

In analogy to the method described in example 12.1, methanesulfonic acid esters were reacted with secondary or primary amines in N,N-dimethylacetamide to yield tertiary or secondary amine products as listed in the following table.

| Example | Product | MS MH$^+$ | Methanesulfonic acid esters | Amine |
|---|---|---|---|---|
| 12.2 | trans-[2-(4-{3-[Ethyl-(2-hydroxy-ethyl)-amino]-propyl}-cyclohexyl)-ethyl]-methyl-carbamic acid 4-trifluoromethyl-phenyl ester | 459 | trans-Methanesulfonic acid 3-(4-{2-[methyl-(4-trifluoromethyl-phenoxycarbonyl)-amino]-ethyl}-cyclohexyl)-propyl ester | Ethyl-(2-hydroxy-ethyl)-amine |
| 12.3 | trans-Methyl-{2-[4-(3-morpholin-4-yl-propyl)-cyclohexyl]-ethyl}-carbamic acid 4-trifluoromethyl-phenyl ester | 457 | trans-Methanesulfonic acid 3-(4-{2-[methyl-(4-trifluoromethyl-phenoxycarbonyl)-amino]-ethyl}-cyclohexyl)-propyl ester | Morpholine |
| 12.4 | trans-Methyl-{2-[4-(3-piperidin-1-yl-propyl)-cyclohexyl]-ethyl}-carbamic acid 4-trifluoromethyl-phenyl ester | 455 | trans-Methanesulfonic acid 3-(4-{2-[methyl-(4-trifluoromethyl-phenoxycarbonyl)-amino]-ethyl}-cyclohexyl)-propyl ester | Piperidine |
| 12.5 | trans-{2-[4-(3-Dimethylamino-propyl)-cyclohexyl]-ethyl}-methyl-carbamic acid 4-trifluoromethyl-phenyl ester | 415 | trans-Methanesulfonic acid 3-(4-{2-[methyl-(4-trifluoromethyl-phenoxycarbonyl)-amino]-ethyl}-cyclohexyl)-propyl ester | Dimethyl-amine |
| 12.6 | trans-{2-[4-(3-Diethylamino-propyl)-cyclohexyl]-ethyl}-methyl-carbamic acid 4-trifluoromethyl-phenyl ester | 443 | trans-Methanesulfonic acid 3-(4-{2-[methyl-(4-trifluoromethyl-phenoxycarbonyl)-amino]-ethyl}-cyclohexyl)-propyl ester | Diethyl-amine |
| 12.7 | trans-Methyl-(2-{4-[3-(methyl-propyl-amino)-propyl]-cyclohexyl}-ethyl)-carbamic acid 4- | 443 | trans-Methanesulfonic acid 3-(4-{2-[methyl-(4-trifluoromethyl-phenoxycarbonyl)- | 3-(Methyl-propyl-amine |

-continued

| Example | Product | MS MH+ | Methanesulfonic acid esters | Amine |
|---|---|---|---|---|
| | trifluoromethyl-phenyl ester | | amino]-ethyl}-cyclohexyl)-propyl ester | |
| 12.8 | trans-[2-(4-{3-[Bis-(2-hydroxy-ethyl)-amino]-propyl}-cyclohexyl)-ethyl]-methyl-carbamic acid 4-trifluoromethyl-phenyl ester | 475 | trans-Methanesulfonic acid 3-(4-{2-[methyl-(4-trifluoromethyl-phenoxycarbonyl)-amino]-ethyl}-cyclohexyl)-propyl ester | Bis-(2-hydroxy-ethyl)-amine |
| 12.9 | trans-Methyl-(2-{4-[3-(4-methyl-piperazin-1-yl)-propyl]-cyclohexyl}-ethyl)-carbamic acid 4-trifluoromethyl-phenyl ester | 470 | trans-Methanesulfonic acid 3-(4-{2-[methyl-(4-trifluoromethyl-phenoxycarbonyl)-amino]-ethyl}-cyclohexyl)-propyl ester | 1-Methyl-piperazine |

Example 13

13.1

In analogy to the procedures described in examples 11.13 and 11.14, trans-[2-(4-hydroxymethyl-cyclohexyl)-ethyl]-methyl-carbamic acid tert-butyl ester (example 11.8) was reacted with methanesulfonyl chloride to give trans-methanesulfonic acid 4-[2-(tert-butoxycarbonyl-methyl-amino)-ethyl]-cyclohexylmethyl ester, which was subsequently treated with 4N hydrogen chloride in dioxan to yield trans-methanesulfonic acid 4-(2-methylamino-ethyl)-cyclohexylmethyl ester HCl salt as colorless solid, MS: 250 (MH+).

13.2

In analogy to the procedure described in example 11.15, trans-methanesulfonic acid 4-(2-methylamino-ethyl)-cyclohexylmethyl ester HCl salt was reacted with 4-(trifluoro-methyl)benzenesulphonyl chloride to yield trans-methanesulfonic acid 4-{2-[methyl-(4-trifluoro-methyl-benzenesulfonyl)-amino]-ethyl}-cyclohexylmethyl ester as colorless viscous oil, MS: 475 (MNH$_4^+$).

13.3

In analogy to the procedure described in example 11.15, trans-methanesulfonic acid 4-(2-methylamino-ethyl)-cyclohexylmethyl ester HCl salt was reacted with 4-trifluoro-methyl-phenyl-chloroformate to yield trans-methanesulfonic acid 4-{2-[methyl-(4-trifluoromethyl-phenoxycarbonyl)-amino]-ethyl}-cyclohexylmethyl ester as colorless viscous oil, MS: 455 (MNH$_4^+$).

13.4

In analogy to the procedure described in example 11.15, trans-methanesulfonic acid 4-(2-methylamino-ethyl)-cyclohexylmethyl ester HCl salt was reacted with 4-chloro-benzene sulphonyl chloride to yield trans-methanesulfonic acid 4-{2-[(4-chloro-benzenesulfonyl)-methyl-amino]-ethyl}-cyclohexylmethyl ester as colorless viscous oil, MS: 424 (MH+, 1Cl).

13.5

In analogy to the procedure described in example 11.15, trans-methanesulfonic acid 4-(2-methylamino-ethyl)-cyclohexylmethyl ester HCl salt was reacted with 4-chloro-phenyl-chloroformate to yield trans-methanesulfonic acid 4-{2-[(4-chloro-phenoxycarbonyl)-methyl-amino]-ethyl}-cyclohexylmethyl ester as colorless viscous oil, MS: 404 (MH+, 1Cl).

Example 14

In analogy to the method described in example 12.1, methanesulfonic acid esters were reacted with secondary or primary amines in N,N-dimethylacetamide to yield tertiary or secondary amine products as listed in the following table:

| Example | Product | MS MH+ | Methanesulfonic acid esters | Amine |
|---|---|---|---|---|
| 14.1 | trans-N-(2-{4-[(Allyl-methyl-amino)-methyl]-cyclohexyl}-ethyl)-N-methyl-4-trifluoromethyl-benzenesulfonamide | 433 | trans-Methanesulfonic acid 4-{2-[methyl-(4-trifluoromethyl-benzenesulfonyl)-amino]-ethyl}-cyclohexylmethyl ester | N-Allyl-methyl-amine |
| 14.2 | trans-(2-{4-[(Allyl-methyl-amino)-methyl]-cyclohexyl}-ethyl)-methyl-carbamic acid 4-trifluoromethyl-phenyl ester | 413 | trans-Methanesulfonic acid 4-{2-[methyl-(4-trifluoromethyl-phenoxycarbonyl)-amino]-ethyl}-cyclohexylmethyl ester | N-Allyl-methyl-amine |

-continued

| Example | Product | MS MH+ | Methanesulfonic acid esters | Amine |
|---|---|---|---|---|
| 14.3 | trans-[2-(4-Dimethylaminomethyl-cyclohexyl)-ethyl]-methyl-carbamic acid 4-trifluoromethyl-phenyl ester | 387 | trans-Methanesulfonic acid 4-{2-[methyl-(4-trifluoromethyl-phenoxycarbonyl)-amino]-ethyl}-cyclohexylmethyl ester | Dimethylamine |
| 14.4 | trans-[2-(4-{[Ethyl-(2-hydroxy-ethyl)-amino]-methyl}-cyclohexyl)-ethyl]-methyl-carbamic acid 4-trifluoromethyl-phenyl ester | 431 | trans-Methanesulfonic acid 4-{2-[methyl-(4-trifluoromethyl-phenoxycarbonyl)-amino]-ethyl}-cyclohexylmethyl ester | Ethyl-(2-hydroxy-ethyl)-amine |
| 14.5 | trans-Methyl-{2-[4-(4-methyl-piperazin-1-ylmethyl)-cyclohexyl]-ethyl}-carbamic acid 4-trifluoromethyl-phenyl ester | 442 | trans-Methanesulfonic acid 4-{2-[methyl-(4-trifluoromethyl-phenoxycarbonyl)-amino]-ethyl}-cyclohexylmethyl ester | 1-Methyl-piperazine |
| 14.6 | trans-(2-{4-[(2-Hydroxy-ethylamino)-methyl]-cyclohexyl}-ethyl)-methyl-carbamic acid 4-trifluoromethyl-phenyl ester | 403 | trans-Methanesulfonic acid 4-{2-[methyl-(4-trifluoromethyl-phenoxycarbonyl)-amino]-ethyl}-cyclohexylmethyl ester | 2-Hydroxy-ethylamine |
| 14.7 | trans-(2-{4-[(2-Hydroxy-1,1-dimethyl-ethylamino)-methyl]-cyclohexyl}-ethyl)-methyl-carbamic acid 4-trifluoromethyl-phenyl ester | 431 | trans-Methanesulfonic acid 4-{2-[methyl-(4-trifluoromethyl-phenoxycarbonyl)-amino]-ethyl}-cyclohexylmethyl ester | 2-Amino-2-methyl-propanol |
| 14.8 | trans-[2-(4-Allylaminomethyl-cyclohexyl)-ethyl]-methyl-carbamic acid 4-trifluoromethyl-phenyl ester | 399 | trans-Methanesulfonic acid 4-{2-[methyl-(4-trifluoromethyl-phenoxycarbonyl)-amino]-ethyl}-cyclohexylmethyl ester | Allyl-amine |
| 14.9 | trans-Methyl-[2-(4-methylaminomethyl-cyclohexyl)-ethyl]-carbamic acid 4-trifluoromethyl-phenyl ester | 373 | trans-Methanesulfonic acid 4-{2-[methyl-(4-trifluoromethyl-phenoxycarbonyl)-amino]-ethyl}-cyclohexylmethyl ester | Methyl-amine |
| 14.10 | trans-N-[2-(4-Dimethylaminomethyl-cyclohexyl)-ethyl]-N-methyl-4-trifluoromethyl-benzenesulfonamide | 407 | trans-Methanesulfonic acid 4-{2-[methyl-(4-trifluoromethyl-benzenesulfonyl)-amino]-ethyl}-cyclohexylmethyl ester | Dimethyl-amine |
| 14.11 | trans-N-[2-(4-{[Ethyl-(2-hydroxy-ethyl)-amino]-methyl}-cyclohexyl)-ethyl]-N-methyl-4-trifluoromethyl-benzenesulfonamide | 451 | trans-Methanesulfonic acid 4-{2-[methyl-(4-trifluoromethyl-benzenesulfonyl)-amino]-ethyl}-cyclohexylmethyl ester | Ethyl-(2-hydroxy-ethyl)-amine |
| 14.12 | trans-N-Methyl-N-{2-[4-(4-methyl-piperazin-1-ylmethyl)-cyclohexyl]-ethyl}-4-trifluoromethyl-benzenesulfonamide | 462 | trans-Methanesulfonic acid 4-{2-[methyl-(4-trifluoromethyl-benzenesulfonyl)-amino]-ethyl}-cyclohexylmethyl ester | 1-Methyl-piperazine |
| 14.13 | trans-N-(2-{4-[(2-Hydroxy-ethylamino)-methyl]-cyclohexyl}-ethyl)-N-methyl-4-trifluoromethyl-benzenesulfonamide | 423 | trans-Methanesulfonic acid 4-{2-[methyl-(4-trifluoromethyl-benzenesulfonyl)-amino]-ethyl}-cyclohexylmethyl ester | 2-Hydroxy-ethylamine |
| 14.14 | trans-N-Methyl-N-[2-(4-methylaminomethyl-cyclohexyl)-ethyl]-4-trifluoromethyl-benzenesulfonamide | 393 | trans-Methanesulfonic acid 4-{2-[methyl-(4-trifluoromethyl-benzenesulfonyl)-amino]-ethyl}-cyclohexylmethyl ester | Methyl-amine |

-continued

| Example | Product | MS MH+ | Methanesulfonic acid esters | Amine |
|---|---|---|---|---|
| 14.15 | trans-N-(2-{4-[(2-Hydroxy-1,1-dimethyl-ethylamino)-methyl]-cyclohexyl}-ethyl)-N-methyl-4-trifluoromethyl-benzenesulfonamide | 451 | trans-Methanesulfonic acid 4-{2-[methyl-(4-trifluoromethyl-benzenesulfonyl)-amino]-ethyl}-cyclohexylmethyl ester | 2-Amino-2-methyl-propanol |
| 14.16 | trans-N-[2-(4-Allylaminomethyl-cyclohexyl)-ethyl]-N-methyl-4-trifluoromethyl-benzenesulfonamide | 419 | trans-Methanesulfonic acid 4-{2-[methyl-(4-trifluoromethyl-benzenesulfonyl)-amino]-ethyl}-cyclohexylmethyl ester | Allyl-amine |
| 14.17 | trans-N-Methyl-N-[2-(4-piperidin-1-ylmethyl-cyclohexyl)-ethyl]-4-trifluoromethyl-benzenesulfonamide | 447 | trans-Methanesulfonic acid 4-{2-[methyl-(4-trifluoromethyl-benzenesulfonyl)-amino]-ethyl}-cyclohexylmethyl ester | Piperidine |
| 14.18 | trans-Methyl-[2-(4-piperidin-1-ylmethyl-cyclohexyl)-ethyl]-carbamic acid 4-trifluoromethyl-phenyl ester | 427 | trans-Methanesulfonic acid 4-{2-[methyl-(4-trifluoromethyl-phenoxycarbonyl)-amino]-ethyl}-cyclohexylmethyl ester | Piperidine |
| 14.19 | trans-Methyl-[2-(4-piperidin-1-ylmethyl-cyclohexyl)-ethyl]-carbamic acid 4-chloro-phenyl ester | 393 (1 Cl) | trans-Methanesulfonic acid 4-{2-[(4-chloro-phenoxycarbonyl)-methyl-amino]-ethyl}-cyclohexylmethyl ester | Piperidine |
| 14.20 | trans-[2-(4-{[Ethyl-(2-hydroxy-ethyl)-amino]-methyl}-cyclohexyl)-ethyl]-methyl-carbamic acid 4-chloro-phenyl ester | 397 (1 Cl) | trans-Methanesulfonic acid 4-{2-[(4-chloro-phenoxycarbonyl)-methyl-amino]-ethyl}-cyclohexylmethyl ester | Ethyl-(2-hydroxy-ethyl)-amine |
| 14.21 | trans-[2-(4-Ethylaminomethyl-cyclohexyl)-ethyl]-methyl-carbamic acid 4-chloro-phenyl ester | 353 (1 Cl) | trans-Methanesulfonic acid 4-{2-[(4-chloro-phenoxycarbonyl)-methyl-amino]-ethyl}-cyclohexylmethyl ester | Ethylamine |
| 14.22 | trans-[2-(4-Dimethylaminomethyl-cyclohexyl)-ethyl]-methyl-carbamic acid 4-chloro-phenyl ester | 353 (1 Cl) | trans-Methanesulfonic acid 4-{2-[(4-chloro-phenoxycarbonyl)-methyl-amino]-ethyl}-cyclohexylmethyl ester | Dimethylamine |
| 14.23 | trans-(2-{4-[(Allyl-methyl-amino)-methyl]-cyclohexyl}-ethyl)-methyl-carbamic acid 4-chloro-phenyl ester | 379 (1 Cl) | trans-Methanesulfonic acid 4-{2-[(4-chloro-phenoxycarbonyl)-methyl-amino]-ethyl}-cyclohexylmethyl ester | N-Allyl-methyl-amine |
| 14.24 | trans-Methyl-[2-(4-pyrrolidin-1-ylmethyl-cyclohexyl)-ethyl]-carbamic acid 4-chloro-phenyl ester | 379 (1 Cl) | trans-Methanesulfonic acid 4-{2-[(4-chloro-phenoxycarbonyl)-methyl-amino]-ethyl}-cyclohexylmethyl ester | Pyrrolidine |
| 14.25 | trans-Methyl-[2-(4-methylaminomethyl-cyclohexyl)-ethyl]-carbamic acid 4-chloro-phenyl ester | 339 (1 Cl) | trans-Methanesulfonic acid 4-{2-[(4-chloro-phenoxycarbonyl)-methyl-amino]-ethyl}-cyclohexylmethyl ester | Methylamine |
| 14.26 | trans-4-Chloro-N-methyl-N-[2-(4-piperidin-1-ylmethyl-cyclohexyl)-ethyl]-benzenesulfonamide | 413 (1 Cl) | trans-Methanesulfonic acid 4-{2-[(4-chloro-benzenesulfonyl)-methyl-amino]-ethyl}-cyclohexylmethyl ester | Piperidine |
| 14.27 | trans-4-Chloro-N-[2-(4-dimethylaminomethyl-cyclohexyl)-ethyl]-N-methyl-benzenesulfonamide | 373 (1 Cl) | trans-Methanesulfonic acid 4-{2-[(4-chloro-benzenesulfonyl)-methyl-amino]-ethyl}-cyclohexylmethyl ester | Dimethylamine |
| 14.28 | trans-4-Chloro-N-methyl-N-[2-(4-pyrrolidin-1-ylmethyl-cyclohexyl)-ethyl]-benzenesulfonamide | 399 (1 Cl) | trans-Methanesulfonic acid 4-{2-[(4-chloro-benzenesulfonyl)-methyl-amino]-ethyl}-cyclohexylmethyl ester | Pyrrolidine |
| 14.29 | trans-N-(2-{4-[(Allyl-methyl-amino)-methyl]-cyclohexyl}- | 399 (1 Cl) | trans-Methanesulfonic acid 4-{2-[(4-chloro- | N-Allyl-methyl-amine |

-continued

| Example | Product | MS MH⁺ | Methanesulfonic acid esters | Amine |
|---|---|---|---|---|
| | ethyl)-4-chloro-N-methyl-benzenesulfonamide | | benzenesulfonyl)-methyl-amino]-ethyl}-cyclohexylmethyl ester | |
| 14.30 | trans-4-Chloro-N-methyl-N-[2-(4-methylaminomethyl-cyclohexyl)-ethyl]-benzenesulfonamide | 359 (1 Cl) | trans-Methanesulfonic acid 4-{2-[(4-chloro-benzenesulfonyl)-methyl-amino]-ethyl}-cyclohexylmethyl ester | Methylamine |
| 14.31 | trans-4-Chloro-N-[2-(4-{[ethyl-(2-hydroxy-ethyl)-amino]-methyl}-cyclohexyl)-ethyl]-N-methyl-benzenesulfonamide | 417 (1 Cl) | trans-Methanesulfonic acid 4-{2-[(4-chloro-benzenesulfonyl)-methyl-amino]-ethyl}-cyclohexylmethyl ester | Ethyl-(2-hydroxy-ethyl)-amine |
| 14.32 | trans-4-Chloro-N-[2-(4-ethylaminomethyl-cyclohexyl)-ethyl]-N-methyl-benzenesulfonamide | 373 (1 Cl) | trans-Methanesulfonic acid 4-{2-[(4-chloro-benzenesulfonyl)-methyl-amino]-ethyl}-cyclohexylmethyl ester | Ethylamine |
| 14.33 | trans-(2-{4-[(6-Hydroxy-hexylamino)-methyl]-cyclohexyl}-ethyl)-methyl-carbamic acid 4-chloro-phenyl ester | 425 (1 Cl) | trans-Methanesulfonic acid 4-{2-[(4-chloro-phenoxycarbonyl)-methyl-amino]-ethyl}-cyclohexylmethyl ester | 6-Hydroxy-hexylamine |
| 14.34 | trans-(2-{4-[(5-Hydroxy-pentylamino)-methyl]-cyclohexyl}-ethyl)-methyl-carbamic acid 4-chloro-phenyl ester | 411 (1 Cl) | trans-Methanesulfonic acid 4-{2-[(4-chloro-phenoxycarbonyl)-methyl-amino]-ethyl}-cyclohexylmethyl ester | 5-Hydroxy-pentylamine |
| 14.35 | trans-4-Chloro-N-(2-{4-[(5-hydroxy-pentylamino)-methyl]-cyclohexyl}-ethyl)-N-methyl-benzenesulfonamide | 431 (1 Cl) | trans-Methanesulfonic acid 4-{2-[(4-chloro-benzenesulfonyl)-methyl-amino]-ethyl}-cyclohexylmethyl ester | 5-Hydroxy-pentylamine |
| 14.36 | trans-4-Chloro-N-(2-{4-[(6-hydroxy-hexylamino)-methyl]-cyclohexyl}-ethyl)-N-methyl-benzenesulfonamide | 445 (1 Cl) | trans-Methanesulfonic acid 4-{2-[(4-chloro-benzenesulfonyl)-methyl-amino]-ethyl}-cyclohexylmethyl ester | 6-Hydroxy-hexylamine |
| 14.37 | trans-[2-(4-{[Ethyl-(2-hydroxy-ethyl)-amino]-methyl}-cyclohexyl)-ethyl]-methyl-carbamic acid 4-trifluoromethyl-phenyl ester; hydrochloride | 431 | trans-Methanesulfonic acid 4-{2-[methyl-(4-trifluoromethyl-phenoxycarbonyl)-amino]-ethyl}-cyclohexylmethyl ester | Ethyl-(2-hydroxy-ethyl)-amine |

Example 15

15.1
A solution of 14.36 g (82.5 mmol) of diethyl-azodicarboxylate in 50 ml of tetrahydrofuran was added within 30 minutes to a solution of 11.4 g (75.0 mmol) 4-hydroxy-benzoic acid methyl ester, 20.65 g (78.8 mmol) of triphenylphosphin and 13.5 g (75.0 mmol) of 4-benzyloxy-1-butanol dissolved in 100 ml of tetrahydrofuran. The reaction mixture was then stirred for 1 hour at room temperature, 1 g of triphenylphosphin was added and stirring continued for 1 hour at room temperature and for 30 minutes at reflux. The reaction mixture was then diluted with 200 ml of hexane and filtered. The filtrate was poured into 200 ml of a saturated potassium carbonate solution and extracted 3 times with 200 ml of ethylacetate. The combined ethylacetate phases were washed with brine, dried over magnesium sulfate and evaporated under reduced pressure. The residue formed was chromatographed on silica gel with a 98:2 v/v mixture of dichloromethane and ether as the eluent giving 21.8 g (92.4%) 4-(4-benzyloxy-butoxy)-benzoic acid methyl ester as colorless viscous oil, MS: 314 (M⁺).

15.2
2.7 g (8.6 mmol) of 4-(4-benzyloxy-butoxy)-benzoic acid methyl ester were dissolved in 15.0 ml of methanol. 0.3 g palladium on charcoal (10%) were added and the reaction mixture hydrogenated at normal pressure until the consumption of hydrogen came to an end. Then, it was filtered over celite and evaporated giving 1.79 g (93%) of 4-(4-hydroxy-butoxy)-benzoic acid methyl ester as colorless solid, MS: 224 (M⁺).

15.3
4.0 g (17.8 mmol) of 4-(4-hydroxy-butoxy)-benzoic acid methyl ester were dissolved in 200.0 ml of methanol. 0.4 ml of triethylamine and 4.0 g of rhodium on charcoal (5%) were added and the reaction mixture hydrogenated at 10 bar hydrogen pressure and room temperature until the consumption of hydrogen came to an end. Then, it was filtered over celite and evaporated. The residue formed was chromatographed on silica gel with a 95:5 v/v mixture of dichloromethane and methanol as the eluent giving 3.1 g (75.4%) of cis- and trans-4-(4-hydroxy-butoxy)-cyclohexanecarboxylic acid methyl ester (9:1) as colorless viscous oil, MS: 231 (MH⁺).

15.4
1.6 ml of trifluoroacetic acid were slowly added to a solution 1.45 g (6.3 mmol) cis- and trans-4-(4-hydroxy-butoxy)-cyclohexanecarboxylic acid methyl ester (9:1) and of 1.9 g (7.55 mmol) benzyl 2,2,2-trichloro-acetimidate dissolved in 5 ml of dichloromethane and 5 ml of cyclohexane. After stirring the reaction mixture for 1 hour at room temperature, it was filtered and the filtrate was poured into 50 ml of a saturated sodium hydrogencarbonate solution and extracted 3 times with 50 ml of dichloromethane. The combined dichloromethane phases were washed with brine, dried over magnesium sulfate and evaporated under reduced pressure. The residue formed was chromatographed on silica gel with a 95:5 v/v mixture of dichloromethane and ether as the eluent giving 1.0 g (49.5%) cis- and trans-4-(4-benzyloxy-butoxy)-cyclohexanecarboxylic acid methyl ester (9:1) as colorless viscous oil, MS: 229 [(M-91 ($C_7H_7$))$^+$], 214 [(M-106($C_7H_6O$))$^+$].

15.5

1 ml (1.6 mmol) of an 1 M solution of n-butyl lithium in hexane were added at −78° C. to a solution of 0.2 g (1.3 mmol) of diisopropylamine dissolved in 5 ml of tetrahydrofuran and the reaction mixture was stirred for 15 minutes at this temperature. Then, a solution of 0.480 g (1.50 mmol) cis- and trans-4-(4-benzyloxy-butoxy)-cyclohexanecarboxylic acid methyl ester (9:1) dissolved in 2 ml of tetrahydrofuran were slowly added at −78° C. After stirring for 15 minutes at −78° C., 0.5 ml of methanol were added and the reaction mixture poured into 50 ml of a saturated sodium hydrogencarbonate solution and extracted 3 times with 100 ml of ether. The combined ether phases were washed with brine, dried over magnesium sulfate and evaporated under reduced pressure. The residue formed, cis- and trans-4-(4-benzyloxy-butoxy)-cyclohexanecarboxylic acid methyl ester (58:42), was chromatographed on silica gel with a 9:1 v/v mixture of dichloromethane and ether as the eluent giving 0.231 g (48.1%) cis-4-(4-benzyloxy-butoxy)-cyclohexanecarboxylic acid methyl ester as colorless viscous oil, MS: 229 [(M-91($C_7H_7$))$^+$], 214 [(M-106($C_7H_6O$))$^+$] and 0.152 g (31.7%) trans-4-(4-benzyloxy-butoxy)-cyclohexanecarboxylic acid methyl ester as colorless viscous oil, MS: 229 [(M-91($C_7H_7$))$^+$], 214 [(M-106($C_7H_6O$))$^+$].

15.6

0.730 g (18.3 mmol) of sodium hydroxide dissolved in 3 ml of water were added to a solution of 2.48 g (7.73 mmol) trans-4-(4-benzyloxy-butoxy)-cyclohexanecarboxylic acid methyl ester in 25 ml of dioxane. After stirring the reaction mixture for 2 hours at reflux, it was cooled to room temperature and poured into 100 ml of an ice/4N aqueous hydrogen chloride mixture, evaporated in part and then extracted 3 times with 100 ml of dichloromethane. The combined dichloromethane phases were washed with brine, dried over magnesium sulfate and evaporated under reduced pressure. The were thus obtained 2.25 g (95%) trans-4-(4-benzyloxy-butoxy)-cyclohexanecarboxylic acid as a light brown viscous oil, MS: 305 [(M−H)$^−$].

15.7

2.22 g (7.25 mmol) trans-4-(4-benzyloxy-butoxy)-cyclohexanecarboxylic acid were dissolved in 10 ml thionylchloride and the reaction mixture stirred at reflux for 1 hour. It was then evaporated and the residue formed dissolved in 10 ml of dichloromethane. This solution was slowly added to a vigorously stirred mixture of 10 ml of methylamine in water (40%) and 50 ml of dichloromethane kept at −5° C. Intense stirring was continued at room temperature for 1 hour. Then, the phases were separated and the aqueous phase extracted again 2 times with 50 ml of dichloromethane. The combined dichloromethane phases were washed with sodium hydrogencarbonate solution and brine, dried over magnesium sulfate and evaporated under reduced pressure. The were thus obtained 2.27 g (98%) trans-4-(4-benzyloxy-butoxy)-cyclohexanecarboxylic acid methylamide as a light brown viscous oil, MS: 320 (MH$^+$).

15.8

2.2 g (6.88 mmol) trans-4-(4-benzyloxy-butoxy)-cyclohexanecarboxylic acid methylamide dissolved in 10 ml of tetrahydrofuran were added slowly to a suspension of 0.261 g of lithium aluminium hydride in 10 ml of tetrahydrofuran. The reaction mixture was then stirred at 50° C. for 2 hours, cooled to 0° C., treated with 2 g of ice, stirred at room temperature for 30 minutes, diluted with ethyl acetate, dried over sodium sulfate, filtered and evaporated to give 2.05 g (97.4%) trans-[4-(4-benzyloxy-butoxy)-cyclohexylmethyl]-methyl-amine as light brown viscous oil, MS: 306 (MH$^+$).

15.9

2.05 g (6.71 mmol) trans-[4-(4-benzyloxy-butoxy)-cyclohexylmethyl]-methyl-amine were dissolved in 15 ml of methanol, cooled to −10° C. and treated at once with 1.61 g (7.38 mmol) di-tert-butyl-dicarbonate. Then, the reaction mixture was stirred at −10° C. for 30 minutes and at room temperature for 2 hours. Subsequently, 2 ml of water and 1 ml of triethylamine were added and the reaction mixture evaporated under reduced pressure. It was then poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 9:1 v/v mixture of dichloromethane and ether as the eluent giving 2.15 g (79%) trans-[4-(4-benzyloxy-butoxy)-cyclohexylmethyl]-methyl-carbamic acid tert-butyl ester as colorless viscous oil, MS: 406 (MH$^+$).

15.10

2.15 g (5.3 mmol) of trans-[4-(4-benzyloxy-butoxy)-cyclohexylmethyl]-methyl-carbamic acid tert-butyl ester were dissolved in 20.0 ml of methanol, 0.3 g palladium on charcoal (10%) were added and the reaction mixture hydrogenated at normal pressure until the consumption of hydrogen came to an end. Then, it was filtered over celite and evaporated giving 1.60 g (95.6%) of trans-[4-(4-hydroxy-butoxy)-cyclohexylmethyl]-methyl-carbamic acid tert-butyl ester as colorless viscous oil, MS: 315 (M$^+$).

15.11

In analogy to the sequence described in examples 1.5 and 1.6, trans-[4-(4-hydroxy-butoxy)-cyclohexylmethyl]-methyl-carbamic acid tert-butyl ester was treated with hydrogen chloride solution in methanol/water followed by acylation with 4-trifluoromethyl-benzenesulfochloride giving trans-N-[4-(4-hydroxy-butoxy)-cyclohexylmethyl]-N-methyl-4-trifluoromethyl-benzenesulfonamide as colorless solid, MS: 424 (M$^+$).

15.12

In analogy to the procedure described in example 3.4, trans-N-[4-(4-hydroxy-butoxy)-cyclohexylmethyl]-N-methyl-4-trifluoromethyl-benzenesulfonamide was treated with methanesulfonyl chloride to yield trans-methanesulfonic acid 4-(4-{[methyl-(4-trifluoromethyl-benzenesulfonyl)-amino]-methyl}-cyclohexyloxy)-butyl ester as colorless solid, MS: 502 (M$^+$).

15.13

In analogy to the sequence described in examples 1.5 and 1.6, trans-[4-(4-hydroxy-butoxy)-cyclohexylmethyl]-methyl-carbamic acid tert-butyl ester was treated with hydrogen chloride solution in methanol/water followed by acylation with 4-chloro-benzenesulfochloride giving trans-4-chloro-N-[4-(4-hydroxy-butoxy)-cyclohexylmethyl]-N-methyl-benzenesulfonamide as colorless viscous oil, MS: 390 (MH$^+$, 1Cl).

15.14

In analogy to the procedure described in example 3.4, trans-4-chloro-N-[4-(4-hydroxy-butoxy)-cyclohexylmethyl]-N-methyl-benzenesulfonamide was treated with methanesulfonyl chloride to yield trans-methanesulfonic acid 4-(4-{[(4-chloro-benzenesulfonyl)-methyl-amino]-methyl}-cyclohexyloxy)-butyl ester as colorless solid, MS: 468 (MH$^+$, 1Cl).

15.15

In analogy to the sequence described in examples 1.5 and 1.7, trans-[4-(4-hydroxy-butoxy)-cyclohexylmethyl]-methyl-carbamic acid tert-butyl ester was treated with hydrogen chloride solution in methanol/water followed by acylation with 4-chlorophenyl chloroformate giving trans-[4-(4-hydroxy-butoxy)-cyclohexylmethyl]-methyl-carbamic acid 4-chloro-phenyl ester as colorless viscous oil, MS: 370 (MH$^+$, 1Cl).

15.16

In analogy to the procedure described in example 3.4, trans-[4-(4-hydroxy-butoxy)-cyclohexylmethyl]-methyl-carbamic acid 4-chloro-phenyl ester was treated with methanesulfonyl chloride to yield trans-methanesulfonic acid 4-(4-{[(4-chloro-phenoxy-carbonyl)-methyl-amino]-methyl}-cyclohexyloxy)-butyl ester as colorless viscous, MS: 448 (MH$^+$, 1 Cl).

15.17

In analogy to the sequence described in examples 15.6, 15.7, 15.8, 15.9 and 15.10, cis-4-(4-benzyloxy-butoxy)-cyclohexanecarboxylic acid methyl ester (example 15.5) was hydrolysed with sodium hydroxide in water/dioxane, then, the acid formed was converted into its N-methyl-amide, which was reduced with lithium aluminium hydride, treated with di-tert-butyl-dicarbonate and hydrogenated giving cis-[4-(4-hydroxy-butoxy)-cyclohexyl-methyl]-methyl-carbamic acid tert-butyl ester as colorless viscous oil, MS: 316 (MH$^+$).

15.18

In analogy to the sequence described in examples 1.5 and 1.6, cis-[4-(4-hydroxy-butoxy)-cyclohexylmethyl]-methyl-carbamic acid tert-butyl ester was treated with hydrogen chloride solution in methanol/water followed by acylation with 4-chloro-benzenesulfochloride giving cis-4-chloro-N-[4-(4-hydroxy-butoxy)-cyclohexylmethyl]-N-methyl-benzene-sulfonamide as colorless viscous oil, MS: 300 [(M-89($C_4H_9O_2$))$^+$, 1 Cl].

15.19

In analogy to the procedure described in example 3.4, cis-4-chloro-N-[4-(4-hydroxy-butoxy)-cyclohexylmethyl]-N-methyl-benzenesulfonamide was treated with methanesulfonyl chloride to yield cis-methanesulfonic acid 4-(4-{[(4-chloro-benzenesulfonyl)-methyl-amino]-methyl}-cyclohexyloxy)-butyl ester as colorless viscous oil, MS: 468 (MH$^+$, 1 Cl).

Example 16

In analogy to the method described in example 2.1, methanesulfonic acid esters were treated with secondary or primary amines in methanol or N,N-dimethylacetamide to yield tertiary or secondary amine products as listed in the following table.

| Example | Product | MS MH$^+$ | Methanesulfonic acid esters | Amine |
|---|---|---|---|---|
| 16.1 | trans-N-{4-[4-(Allyl-methyl-amino)-butoxy]-cyclohexylmethyl}-4-chloro-N-methyl-benzenesulfonamide | 443 (1 Cl) | trans-Methanesulfonic acid 4-(4-{[(4-chloro-benzenesulfonyl)-methyl-amino]-methyl}-cyclohexyloxy)-butyl ester | N-Allyl-methyl-amine |
| 16.2 | cis-N-{4-[4-(Allyl-methyl-amino)-butoxy]-cyclohexylmethyl}-4-chloro-N-methyl-benzenesulfonamide | 443 (1 Cl) | cis-Methanesulfonic acid 4-(4-{[(4-chloro-benzenesulfonyl)-methyl-amino]-methyl}-cyclohexyloxy)-butyl ester | N-Allyl-methyl-amine |
| 16.3 | trans-{4-[4-(Allyl-methyl-amino)-butoxy]-cyclohexylmethyl}-methyl-carbamic acid 4-chloro-phenyl ester | 423 (1 Cl) | trans-Methanesulfonic acid 4-(4-{[(4-chloro-phenoxycarbonyl)-methyl-amino]-methyl}-cyclohexyloxy)-butyl ester | N-Allyl-methyl-amine |
| 16.4 | trans-N-{4-[4-(Allyl-methyl-amino)-butoxy]-cyclohexylmethyl}-N-methyl-4-trifluoromethyl-benzenesulfonamide | 477 | trans-Methanesulfonic acid 4-(4-{[methyl-(4-trifluoromethyl-benzenesulfonyl)-amino]-methyl}-cyclohexyloxy)-butyl ester | N-Allyl-methyl-amine |
| 16.5 | trans-N-(4-{4-[Ethyl-(2-hydroxy-ethyl)-amino]-butoxy}-cyclohexylmethyl)-N-methyl-4-trifluoromethyl-benzenesulfonamide | 495 | trans-Methanesulfonic acid 4-(4-{[methyl-(4-trifluoromethyl-benzenesulfonyl)-amino]-methyl}-cyclohexyloxy)-butyl ester | Ethyl-(2-hydroxy-ethyl)-amine |

Example 17

17.1

To a dry ice-cooled solution of 4 g (11.8 mmol) trans-3-{4-[2-(tert-butoxycarbonyl-methyl-amino)-ethyl]-cyclohexyl}-(E)-acrylic acid ethyl ester (example 11.10) in 50 ml of tetrahydrofuran was added at −75° C. to −63° C. within 15 minutes 23.6 ml (28.3 mmol) of a solution of diisobutyl-aluminium hydride (1.2M in toluene). After the reaction mixture was stirred for 2 hours at −75° C., 20 ml of methanol was added at −75° C. to this mixture. The temperature was raised to 20° C. and 20 ml 1N hydrogen chloride solution was added. The reaction mixture was partitioned between ether, 1N hydrogen chloride solution, sodium hydrogen carbonate solution and water. The organic layer was dried over magnesium sulfate and concentrated under reduced pressure giving 3.61 g of trans-{2-[4-(3-hydroxy-(E)-propenyl)-cyclohexyl]-ethyl}-methyl-carbamic acid tert-butyl ester as slightly yellow viscous oil, MS: 298 (MH$^+$).

17.2

A solution of 200 mg (0.672 mmol) trans{2-[4-(3-hydroxy-(E)-propenyl)-cyclohexyl]-ethyl}-methyl-carbamic acid tert-butyl ester in 2 ml 4M hydrogen chloride solution in dioxane was stirred for 30 minutes at room temperature. The reaction mixture was then concentrated under reduced pressure. The crude HCl-salt was triturated two times with dry ether and the crystalline product then dried for several hours at 45° C. and 15 mbar to give 155 mg (98.6%) of pure trans-3-[4-(2-methylamino-ethyl)-cyclohexyl]-(E)-prop-2-en-1-ol HCl-salt as colorless cristalls, MS: 198 (MH$^+$).

17.3

To a solution of 150 mg (0.642 mmol) trans-3-[4-(2-methylamino-ethyl)-cyclohexyl]-(E)-prop-2-en-1-ol HCl-salt and 125 mg (0.654 mmol) 4-chlorophenyl chloroformate in 1.5 ml of dichloromethane was added at room temperature 0.55 ml (3.21 mmol) diisopropyl ethyl amine. The reaction mixture was stirred for 1 hour at room temperature, taken up in ether and washed with 1N hydrogen chloride solution and water. The organic layer was dried over magnesium sulfate and concentrated under reduced pressure and the residue then chromatographed on silica gel with a 2:1 v/v mixture of hexane and ethylacetate as the eluent giving 146 mg (64.7%) trans-{2-[4-(3-hydroxy-(E)-propenyl)-cyclohexyl]-ethyl}-methyl-carbamic acid 4-chloro-phenyl ester, MS: 369 (MNH$_4^+$, 1Cl).

17.4

To an ice-cooled solution of 135 mg (0.384 mmol) trans-{2-[4-(3-hydroxy-(E)-propenyl)-cyclohexyl]-ethyl}-methyl-carbamic acid 4-chloro-phenyl ester and 0.089 ml (0.77 mmol) 2,6-lutidine in 2 ml of dichloromethane was added under stirring 0.033 ml (0.422 mmol) methane sulfonylchloride. The reaction mixture was stirred for 20 hours at room temperature, then taken up in ether and washed with 1N hydrogen chloride solution and water. The organic layer was dried over magnesium sulfate and concentrated under reduced pressure and the residue then chromatographed on silica gel with a 4:1 v/v mixture of hexane and ethylacetate as the eluent giving 90 mg (63.4%) of trans-{2-[4-(3-chloro-(E)-propenyl)-cyclohexyl]-ethyl}-methyl-carbamic acid 4-chloro-phenyl ester as colorless viscous oil, MS: 370 (MH$^+$, 2 Cl).

17.5

In analogy to the sequence described in examples 17.1 and 17.2, trans-3-{4-[(tert-butoxycarbonyl-methyl-amino)-methyl]-cyclohexyl}-(E,Z)-acrylic acid methyl ester (E:Z=9:1) (example 7.1) was reduced with diisobutyl-aluminium hydride followed by the removal of the protective tert-butoxycarbonyl function with 4M hydrogen chloride solution in dioxane to yield trans-3-(4-methylaminomethyl-cyclohexyl)-(E,Z)-prop-2-en-1-ol (E:Z=9:1) as colorless viscous oil, which was used without further characterization.

17.6

In analogy to the sequence described in examples 1.6 and 17.4, trans-3-(4-methyl-aminomethyl-cyclohexyl)-(E,Z)-prop-2-en-1-ol (E:Z=9:1) was reacted with 4-trifluoromethyl-benzene sulfochloride and potassium carbonate (dissolved in the minimal amount of water) in tetrahydrofuran to yield trans-N-[4-(3-hydroxy-(E,Z)-propenyl)-cyclohexyl-methyl]-N-methyl-4-trifluoromethyl-benzenesulfonamide (E:Z=9:1) as colorless viscous oil, MS: 409 (MNH$_4^+$). It was subsequently treated with methane sulfonylchloride and 2,6-lutidine in dichloromethane to yield trans-N-[4-(3-chloro-(E,Z)-propenyl)-cyclohexyl-methyl]-N-methyl-4-trifluoromethyl-benzenesulfonamide (E:Z=9:1) as colorless viscous oil, MS: 410 (MH$^+$, 1 Cl).

17.7

In analogy to the sequence described in examples 17.3 and 17.4, trans-3-[4-(2-methylamino-ethyl)-cyclohexyl]-(E)-prop-2-en-1-ol HCl was reacted with 4-trifluoromethyl-benzene sulfochloride in dichloromethane in the presence of diisopropyl ethyl amine followed by treatment with methane sulfonylchloride and 2,6-lutidine in dichloromethane to yield trans-N-{2-[4-(3-chloro-(E)-propenyl)-cyclohexyl]-ethyl}-N-methyl-4-trifluoromethyl-benzenesulfonamide as colorless viscous oil, MS: 424 (MH$^+$, 1Cl).

Example 18

18.1

In analogy to the method described in example 12.1, trans-{2-[4-(3-chloro-(E)-propenyl)-cyclohexyl]-ethyl}-methyl-carbamic acid 4-chloro-phenyl ester was reacted with piperidine in N,N-dimethylacetamide at room temperature to yield trans-methyl-{2-[4-(3-piperidin-1-yl-(E)-propenyl)-cyclohexyl]-ethyl}-carbamic acid 4-chloro-phenyl ester as colorless viscous oil, MS: 419 (MH$^+$, 1Cl).

18.2

In analogy to the method described in example 12.1, trans-N-[4-(3-chloro-(E,Z)-propenyl)-cyclohexylmethyl]-N-methyl-4-trifluoromethyl-benzenesulfonamide (E:Z=9:1) was reacted with piperidine in N,N-dimethylacetamide at room temperature to yield trans-N-methyl-N-[4-(3-piperidin-1-yl-(E,Z)-propenyl)-cyclohexylmethyl]-4-trifluoromethyl-benzenesulfonamide (E:Z=9:1) as yellow solid, MS: 459 (MH$^+$).

18.3

In analogy to the method described in example 12.1, trans-N-[4-(3-chloro-(E,Z)-propenyl)-cyclohexylmethyl]-N-methyl-4-trifluoromethyl-benzenesulfonamide (E:Z=9:1) was reacted with ethyl-(2-hydroxy-ethyl)-amine in N,N-dimethylacetamide at room temperature to yield trans-N-(4-{3-[ethyl-(2-hydroxy-ethyl)-amino]-(E,Z)-propenyl}-cyclohexylmethyl)-N-methyl-4-trifluoromethyl-benzenesulfonamide (E:Z=9:1) as colorless solid, MS: 463 (MH$^+$).

18.4

In analogy to the method described in example 12.1, trans-N-{2-[4-(3-chloro-(E)-propenyl)-cyclohexyl]-ethyl}-N-methyl-4-trifluoromethyl-benzenesulfonamide was reacted with N-allyl-methyl-amine in N,N-dimethylacetamide at room temperature to yield trans-N-(2-{4-[3-(allyl-methyl-amino)-(E)-propenyl]-cyclohexyl}-ethyl)-N-methyl-4-trifluoromethyl-benzenesulfonamide as colorless viscous oil, MS: 459 (MH$^+$).

18.5

In analogy to the method described in example 12.1, trans-N-{2-[4-(3-chloro-(E)-propenyl)-cyclohexyl]-ethyl}-N-methyl-4-trifluoromethyl-benzenesulfonamide was reacted with dimethyl-amine in N,N-dimethylacetamide at room temperature to yield trans-N-{2-[4-(3-dimethylamino-(E)-propenyl)-cyclohexyl]-ethyl}-N-methyl-4-trifluoromethyl-benzenesulfonamide as colorless viscous oil, MS: 433 (MH$^+$).

18.6

In analogy to the method described in example 12.1, trans-N-{2-[4-(3-chloro-(E)-propenyl)-cyclohexyl]-ethyl}-N-methyl-4-trifluoromethyl-benzenesulfonamide was reacted with piperidine in N,N-dimethylacetamide at room temperature to yield trans-N-methyl-N-{2-[4-(3-piperidin-1-yl-(E)-propenyl)-cyclohexyl]-ethyl}-4-trifluoromethyl-benzenesulfonamide as colorless viscous oil, MS: 473 (MH$^+$).

18.7

In analogy to the method described in example 12.1, trans-N-{2-[4-(3-chloro-(E)-propenyl)-cyclohexyl]-ethyl}-N-methyl-4-trifluoromethyl-benzenesulfonamide was reacted with ethylamine in N,N-dimethylacetamide at room temperature to yield trans-N-{2-[4-(3-ethylamino-(E)-propenyl)-cyclohexyl]-ethyl}-N-methyl-4-trifluoromethyl-benzenesulfonamide as colorless viscous oil, MS: 433 (MH$^+$).

18.8

In analogy to the method described in example 12.1, trans-{2-[4-(3-chloro-(E)-propenyl)-cyclohexyl]-ethyl}-methyl-carbamic acid 4-chloro-phenyl ester was reacted with N-allyl-methyl-amine in N,N-dimethylacetamide at room temperature to yield trans-(2-{4-[3-(allyl-methyl-amino)-(E)-propenyl]-cyclohexyl}-ethyl)-methyl-carbamic acid 4-chloro-phenyl ester as light yellow viscous oil, MS: 405 (MH$^+$, 1Cl).

18.9

In analogy to the method described in example 12.1, trans-{2-[4-(3-chloro-(E)-propenyl)-cyclohexyl]-ethyl}-methyl-carbamic acid 4-chloro-phenyl ester was reacted with dimethylamine in N,N-dimethylacetamide at room temperature to yield trans-{2-[4-(3-dimethylamino-(E)-propenyl)-cyclohexyl]-ethyl}-methyl-carbamic acid 4-chloro-phenyl ester as light yellow viscous oil, MS: 379 (MH$^+$, 1Cl).

18.10

In analogy to the method described in example 12.1, trans-{2-[4-(3-chloro-(E)-propenyl)-cyclohexyl]-ethyl}-methyl-carbamic acid 4-chloro-phenyl ester was reacted with ethylamine in N,N-dimethylacetamide at room temperature to yield trans-{2-[4-(3-ethylamino-(E)-propenyl)-cyclohexyl]-ethyl}-methyl-carbamic acid 4-chloro-phenyl ester as light yellow viscous oil, MS: 379 (MH$^+$, 1Cl).

18.11

In analogy to the method described in example 12.1, trans-{2-[4-(3-chloro-(E)-propenyl)-cyclohexyl]-ethyl}-methyl-carbamic acid 4-chloro-phenyl ester was reacted with pyrrolidine in N,N-dimethylacetamide at room temperature to yield trans-methyl-{2-[4-(3-pyrrolidin-1-yl-(E)-propenyl)-cyclohexyl]-ethyl}-carbamic acid 4-chloro-phenyl ester as yellow viscous oil, MS: 405 (MH$^+$, 1Cl).

Example 19

19.1

A heterogenous mixture of 1.59 g (4.35 mmol) of trans-N-(4-hydroxymethyl-cyclohexylmethyl)-N-methyl-4-trifluoromethyl-benzenesulfonamide (example 5.1), 5.0 ml of dichloromethane, 37.2 g (174 mmol) of (E)-1,4-dibromo-2-butene, 15.0 ml of 50% w/w sodium hydroxide solution and 0.44 g (1.3 mmol) of tetrabutylammonium hydrogensulfate was stirred vigorously at room temperature for 3 days. Afterwards, 30 ml of deionized water were added and the reaction mixture was extracted with 3 portions of n-hexane. The combined organic phases were then washed with water (3 times), 1 N aqueous hydrochloric acid solution, saturated aqueous sodium bicarbonate solution, brine and were finally dried over magnesium sulfate and evaporated under reduced pressure. The excess of the (E)-1,4-dibromo-2-butene was distilled off under reduced pressure (0.5 torr) at 100° C. The residue thus obtained was chromatographed on silicagel with a 3:1 v/v mixture of dichloromethane and hexane as the eluent giving 1.51 g (69.6%) of trans-N-[4-(4-bromo-(E)-but-2-enyloxymethyl)-cyclohexylmethyl]-N-methyl-4-trifluoromethyl-benzenesulfonamide as pale yellow solid, MS: 515 (MNH$_4^+$, 1Br).

19.2

In analogy to the method described in example 19.1, trans-N-(4-hydroxymethyl-cyclohexylmethyl)-N-methyl-4-trifluoromethyl-benzenesulfonamide (example 5.1) was reacted with 1,4-dibromo-butane in dichloromethane and aqueous sodium hydroxide solution in the presence of tetrabutylammonium hydrogensulfate to yield trans-N-[4-(4-bromo-butoxymethyl)-cyclohexylmethyl]-N-methyl-4-trifluoromethyl-benzenesulfonamide as colorless solid, MS: 500 (MH$^+$, 1Br).

19.3

In analogy to the method described in example 19.1, trans-(4-hydroxymethyl-cyclohexylmethyl)-methyl-carbamic acid 4-chloro-phenyl ester (example 5.3) was reacted with 1,4-dibromo-butane in dichloromethane and aqueous sodium hydroxide solution in the presence of tetrabutylammonium hydrogensulfate to yield trans-[4-(4-bromo-butoxymethyl)-cyclohexylmethyl]-methyl-carbamic acid 4-chloro-phenyl ester as colorless solid, MS: 446 (MH$^+$, 1Cl, 1Br).

Example 20

20.1

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with piperidine in N,N-dimethylacetamide at room temperature to yield trans-N-methyl-N-[4-(4-piperidin-1-yl-(E)-but-2-enyloxymethyl)-cyclohexylmethyl]-4-trifluoromethyl-benzenesulfonamide as yellow solid, MS: 503 (MH$^+$).

20.2

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with pyrrolidine in N,N-dimethylacetamide at room temperature to yield trans-N-methyl-N-[4-(4-pyrrolidin-1-yl-(E)-but-2-enyloxymethyl)-cyclohexylmethyl]-4-trifluoromethyl-benzenesulfonamide as light yellow solid, MS: 489 (MH$^+$).

20.3

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with ethyl-(2-hydroxy-ethyl)-amine in N,N-dimethylacetamide at room temperature to yield trans-N-(4-{4-[ethyl-(2-hydroxy-ethyl)-amino]-(E)-but-2-enyloxymethyl}-cyclohexylmethyl)-N-methyl-4-trifluoromethyl-benzenesulfonamide as light yellow solid, MS: 507 (MH$^+$).

20.4

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with N-allyl-methyl-amine in N,N-dimethylacetamide at room temperature to yield trans-N-{4-[4-(allyl-methyl-amino)-(E)-but-2-enyloxymethyl]-cyclohexylmethyl}-N-methyl-4-trifluoromethyl-benzenesulfonamide as light yellow viscous oil, MS: 489 (MH$^+$).

20.5

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with bis-(2-hydroxy-ethyl)-amine in N,N-dimethylacetamide at room temperature to yield trans-N-(4-{4-[bis-(2-hydroxy-ethyl)-amino]-(E)-but-2-enyloxymethyl}-cyclohexylmethyl)-N-methyl-4-trifluoromethyl-benzenesulfonamide as light yellow solid, MS: 523 (MH$^+$).

20.6

In analogy to the method described in example 12. 1, trans-N-[4-(4-bromo-(E)-but-2-enyloxymethyl)-cyclohexylmethyl]-N-methyl-4-trifluoromethyl-benzenesulfonamide was reacted with methylamine in N,N-dimethylacetamide at room temperature to yield trans-N-methyl-N-[4-(4-methylamino-(E)-but-2-enyloxymethyl)-cyclohexylmethyl]-4-trifluoromethyl-benzenesulfonamide as light yellow solid, MS: 449 (MH$^+$).

20.7

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with (2-hydroxy-ethyl)-methyl-amine in N,N-dimethylacetamide at room temperature to yield trans-N-(4-{4-[(2-hydroxy-ethyl)-methyl-amino]-(E)-but-2-enyloxymethyl}-cyclohexylmethyl)-N-methyl-4-trifluoromethyl-benzenesulfonamide as light yellow solid, MS: 493 (MH$^+$).

20.8

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with morpholine in N,N-dimethylacetamide at room temperature to yield trans-N-methyl-N-[4-(4-morpholin-4-yl-(E)-but-2-enyloxymethyl)-cyclohexylmethyl]-4-trifluoromethyl-benzenesulfonamide as light yellow solid, MS: 505 (MH$^+$).

20.9

In analogy to the method described in example 12.1, trans-N-[4-(4-bromo-(E)-but-2-enyloxymethyl)-cyclohexylmethyl]-N-methyl-4-trifluoromethyl-benzenesulfonamide was reacted with 1-tert-butoxycarbonyl piperazine in N,N-dimethylacetamide at room temperature followed by treatment with trifluoroacetic acid at room temperature to yield trans-N-methyl-N-[4-(4-piperazin-1-yl-(E)-but-2-enyloxymethyl)-cyclohexylmethyl]-4-trifluoromethyl-benzenesulfonamide as light yellow solid, MS: 504 (MH$^+$).

20.10

In analogy to the method described in example 12.1, trans-N-[4-(4-bromo-butoxymethyl)-cyclohexylmethyl]-N-methyl-4-trifluoromethyl-benzenesulfonamide was reacted with piperidine in N,N-dimethylacetamide at room temperature to yield trans-N-methyl-N-[4-(4-piperidin-1-yl-butoxymethyl)-cyclohexylmethyl]-4-trifluoromethyl-benzenesulfonamide as light yellow solid, MS: 505 (MH$^+$).

20.11

In analogy to the method described in example 12.1, trans-N-[4-(4-bromo-butoxymethyl)-cyclohexylmethyl]-N-methyl-4-trifluoromethyl-benzenesulfonamide was reacted with (2-hydroxy-ethyl)-methyl-amine in N,N-dimethylacetamide at room temperature to yield trans-N-(4-{4-[(2-hydroxy-ethyl)-methyl-amino]-butoxymethyl}-cyclohexylmethyl)-N-methyl-4-trifluoromethyl-benzenesulfonamide as colorless solid, MS: 495 (MH$^+$).

20.12

In analogy to the method described in example 12.1, trans-N-[4-(4-bromo-butoxymethyl)-cyclohexylmethyl]-N-methyl-4-trifluoromethyl-benzenesulfonamide was reacted with pyrrolidine in N,N-dimethylacetamide at room temperature to yield trans-N-methyl-N-[4-(4-pyrrolidin-1-yl-butoxymethyl)-cyclohexylmethyl]-4-trifluoromethyl-benzenesulfonamide as yellow solid, MS: 491 (MH$^+$).

20.13

In analogy to the method described in example 12.1, trans-N-[4-(4-bromo-butoxymethyl)-cyclohexylmethyl]-N-methyl-4-trifluoromethyl-benzenesulfonamide was reacted with N-allyl-methyl-amine in N,N-dimethylacetamide at room temperature to yield trans-N-{4-[4-(allyl-methyl-amino)-butoxymethyl]-cyclohexylmethyl}-N-methyl-4-trifluoromethyl-benzenesulfonamide as yellow solid, MS: 491 (MH$^+$).

20.14

In analogy to the method described in example 12.1, trans-N-[4-(4-bromo-butoxymethyl)-cyclohexylmethyl]-N-methyl-4-trifluoromethyl-benzenesulfonamide was reacted with ethyl-(2-hydroxy-ethyl)-amine in N,N-dimethylacetamide at room temperature to yield trans-N-(4-{4-[ethyl-(2-hydroxy-ethyl)-amino]-butoxymethyl}-cyclohexylmethyl)-N-methyl-4-trifluoromethyl-benzenesulfonamide as colorless solid, MS: 509 (MH$^+$).

20.15

In analogy to the method described in example 12.1, trans-N-[4-(4-bromo-butoxymethyl)-cyclohexylmethyl]-N-methyl-4-trifluoromethyl-benzenesulfonamide was reacted with dimethyl-amine in N,N-dimethylacetamide at room temperature to yield trans-N-[4-(4-dimethylamino-butoxymethyl)-cyclohexylmethyl]-N-methyl-4-trifluoromethyl-benzenesulfonamide as colorless solid, MS: 465 (MH$^+$).

20.16

In analogy to the method described in example 12.1, trans-N-[4-(4-bromo-butoxymethyl)-cyclohexylmethyl]-N-methyl-4-trifluoromethyl-benzenesulfonamide was reacted with bis-(2-hydroxy-ethyl)-amine in N,N-dimethylacetamide at room temperature to yield trans-N-(4-{4-[bis-(2-hydroxy-ethyl)-amino]-butoxymethyl}-cyclohexylmethyl)-N-methyl-4-trifluoromethyl-benzenesulfonamideas colorless solid, MS: 525 (MH$^+$).

20.17

In analogy to the method described in example 12.1, trans-N-[4-(4-bromo-butoxymethyl)-cyclohexylmethyl]-N-methyl-4-trifluoromethyl-benzenesulfonamide was reacted with (S)-2-hydroxymethyl-pyrrolidine in N,N-dimethylacetamide at room temperature to yield trans-N-{4-[4-((S)-2-hydroxymethyl-pyrrolidin-1-yl)-butoxymethyl]-cyclohexylmethyl}-N-methyl-4-trifluoromethyl-benzenesulfonamide as colorless solid, MS: 521 (MH$^+$).

20.18

In analogy to the method described in example 12.1, trans-[4-(4-bromo-butoxymethyl)-cyclohexylmethyl]-methyl-carbamic acid 4-chloro-phenyl ester was reacted with pyrrolidine in N,N-dimethylacetamide at 50° C. for 2 hours to yield trans-methyl-[4-(4-pyrrolidin-1-yl-butoxymethyl)-cyclohexylmethyl]-carbamic acid 4-chloro-phenyl ester as colorless viscous oil, MS: 437 (MH$^+$, 1Cl).

20.19

In analogy to the method described in example 12.1, trans-[4-(4-bromo-butoxymethyl)-cyclohexylmethyl]-methyl-carbamic acid 4-chloro-phenyl ester was reacted with piperidine in N,N-dimethylacetamide at 50° C. for 2 hours to yield trans-methyl-[4-(4-piperidin-1-yl-butoxymethyl)-cyclohexylmethyl]-carbamic acid 4-chloro-phenyl ester as colorless viscous oil, MS: 451 (MH$^+$, 1Cl).

20.20

In analogy to the method described in example 12.1, trans-[4-(4-bromo-butoxymethyl)-cyclohexylmethyl]-methyl-carbamic acid 4-chloro-phenyl ester was reacted with (2-hydroxy-ethyl)-methyl-amine in N,N-dimethylacetamide at 50° C. for 3 hours to yield trans-(4-{4-[(2-hydroxy-ethyl)-methyl-amino]-butoxymethyl}-cyclohexylmethyl)-methyl-carbamic acid 4-chloro-phenyl ester as colorless viscous oil, MS: 441 (MH$^+$, 1Cl).

20.21

In analogy to the method described in example 12.1, trans-[4-(4-bromo-butoxymethyl)-cyclohexylmethyl]-methyl-carbamic acid 4-chloro-phenyl ester was reacted with bis-(2-hydroxy-ethyl)-amine in N,N-dimethylacetamide at 50° C. for 3 hours to yield trans-(4-{4-[bis-(2-hydroxy-ethyl)-amino]-butoxymethyl}-cyclohexylmethyl)-methyl-carbamic acid 4-chloro-phenyl ester as colorless viscous oil, MS: 471 (MH$^+$, 1Cl).

20.22

In analogy to the method described in example 12.1, trans-[4-(4-bromo-butoxymethyl)-cyclohexylmethyl]-methyl-carbamic acid 4-chloro-phenyl ester was reacted with dimethylamine in N,N-dimethylacetamide at 50° C. for 3 hours to yield trans-[4-(4-dimethylamino-butoxymethyl)-cyclohexylmethyl]-methyl-carbamic acid 4-chloro-phenyl ester as light yellow viscous oil, MS: 411 (MH$^+$, 1Cl).

20.23

In analogy to the method described in example 12.1, trans-[4-(4-bromo-butoxymethyl)-cyclohexylmethyl]-methyl-carbamic acid 4-chloro-phenyl ester was reacted with ethyl-(2-hydroxy-ethyl)-amine in N,N-dimethylacetamide at 50° C. for 3 hours to yield trans-(4-{4-[ethyl-(2-hydroxy-ethyl)-amino]-butoxymethyl}-cyclohexylmethyl)-methyl-carbamic acid 4-chloro-phenyl ester as colorless viscous oil, MS: 455 (MH$^+$, 1Cl).

Example 21

21.1

A solution of 12.64 g (36.17 mmol) of trans-methanesulfonic acid 4-[2-(tert-butoxycarbonyl-methyl-amino)-ethyl]-cyclohexylmethyl ester (example 13.1) and 4.51 g (92 mmol) of sodium cyanide in 100 ml of dimethylformamide was stirred for 6 hours at 110° C. The reaction mixture was then taken up in ether and washed four times with water. The ether layer was dried over sodium sulfate and concentrated under reduced pressure, giving 10.14 g of crude trans-[2-(4-cyanomethyl-cyclohexyl)-ethyl]-methyl-carbamic acid tert-butyl ester as a colorless oil, which was used without further purification.

21.2

90.4 ml (108.5 mmol) of diisobutylaluminium hydride (1.2M in toluene) were dropped under stirring and dry-ice-cooling at −70° C. to −78° C., within 20 minutes, to a solution of 10.14 g (36.17 mmol) of crude trans-[2-(4-cyanomethyl-cyclohexyl)-ethyl]-methyl-carbamic acid tert-butyl ester in 90 ml of methylenechloride. The reaction mixture was stirred for 4 hours at −70° C. to −78° C. To this reaction mixture was then carefully added 40 ml of 4N HCl (in water), within 10 minutes at −78° C. The temperature was slowly raised to room temperature. After stirring for 10 minutes at room temperature, the reaction mixture was partitioned between ether, 1N HCl and water. The ether-phase was dried over sodium sulfate and concentrated under reduced pressure giving 10.14 g of crude trans-methyl-{2-[4-(2-oxo-ethyl)-cyclohexyl]-ethyl}-carbamic acid tert-butyl ester as colorless oil, which was used without further purification.

21.3

800 mg (21 mmol) of lithium aluminium hydride were added within 10 minutes to a solution of 4.5 g (15.87 mmol) crude trans-methyl-{2-[4-(2-oxo-ethyl)-cyclohexyl]-ethyl}-carbamic acid tert-butyl ester in 40 ml of tetrahydrofuran. After stirring for 3 hours at room temperature, 40 ml of brine was dropped carefully into the reaction mixture. The reaction mixture was stirred for another 20 minutes at room temperature and then partitioned between ether, 1N HCl and water. After drying of the ether phase over sodium sulfate and concentration under reduced pressure, 4.26 g of trans-{2-[4-(2-hydroxy-ethyl)-cyclohexyl]-ethyl}-methyl-carbamic acid tert-butyl ester was obtained, which was used without further purification.

21.4

In analogy to the procedures described in examples 11.13, 11.14 and 11.15, trans-{2-[4-(2-hydroxy-ethyl)-cyclohexyl]-ethyl}-methyl-carbamic acid tert-butyl ester was reacted with methanesulfonyl chloride to give trans-methanesulfonic acid 2-{4-[2-(tert-butoxycarbonyl-methyl-amino)-ethyl]-cyclohexyl}-ethyl ester, which was subsequently treated with 4N hydrogen chloride in dioxan to yield trans-methanesulfonic acid 2-[4-(2-methylamino-ethyl)-cyclohexyl]-ethyl ester HCl salt as colorless solid; treatment of the trans-methanesulfonic acid 2-[4-(2-methylamino-ethyl)-cyclohexyl]-ethyl ester HCl salt with 4-chloro-benzene sulphonyl chloride then yielded trans-methanesulfonic acid 2-(4-{2-[(4-chloro-benzenesulfonyl)-methyl-amino]-ethyl}-cyclohexyl)-ethyl ester as colorless oil, MS: 438 (MH$^+$, 1Cl).

21.5

In analogy to the procedures described in example 11.15, trans-methanesulfonic acid 2-[4-(2-methylamino-ethyl)-cyclohexyl]-ethyl ester HCl salt was treated with 4-chloro-phenyl-chloroformate to yield trans-methanesulfonic acid 2-(4-{2-[(4-chloro-phenoxycarbonyl)-methyl-amino]-ethyl}-cyclohexyl)-ethyl ester as colorless oil, MS: 418 (MH$^+$, 1Cl).

Example 22

In analogy to the method described in example 12.1, methanesulfonic acid esters were reacted with secondary or primary amines in N,N-dimethylacetamide to yield tertiary or secondary amine products as listed in the following table.

| Example | Product | MS MH+ | Methanesulfonic acid esters | Amine |
|---|---|---|---|---|
| 22.1 | trans-Methyl-{2-[4-(2-piperidin-1-yl-ethyl)-cyclohexyl]-ethyl}-carbamic acid 4-chloro-phenyl ester | 407 (1 Cl) | trans-Methanesulfonic acid 2-(4-{2-[(4-chloro-phenoxycarbonyl)-methyl-amino]-ethyl}-cyclohexyl)-ethyl ester | Piperidine |
| 22.2 | trans-4-Chloro-N-methyl-N-{2-[4-(2-piperidin-1-yl-ethyl)-cyclohexyl]-ethyl}-benzenesulfonamide | 427 (1 Cl) | trans-Methanesulfonic acid 2-(4-{2-[(4-chloro-benzenesulfonyl)-methyl-amino]-ethyl}-cyclohexyl)-ethyl ester | Piperidine |
| 22.3 | trans-(2-{4-[2-(Allyl-methyl-amino)-ethyl]-cyclohexyl}-ethyl)-methyl-carbamic acid 4-chloro-phenyl ester | 393 (1 Cl) | trans-Methanesulfonic acid 2-(4-{2-[(4-chloro-phenoxycarbonyl)-methyl-amino]-ethyl}-cyclohexyl)-ethyl ester | N-Allyl-methyl-amine |
| 22.4 | trans-{2-[4-(2-Dimethylamino-ethyl)-cyclohexyl]-ethyl}-methyl-carbamic acid 4-chloro-phenyl ester | 367 (1 Cl) | trans-Methanesulfonic acid 2-(4-{2-[(4-chloro-phenoxycarbonyl)-methyl-amino]-ethyl}-cyclohexyl)-ethyl ester | Dimethylamine |
| 22.5 | trans-{2-[4-(2-Ethylamino-ethyl)-cyclohexyl]-ethyl}-methyl-carbamic acid 4-chloro-phenyl ester | 367 (1 Cl) | trans-Methanesulfonic acid 2-(4-{2-[(4-chloro-phenoxycarbonyl)-methyl-amino]-ethyl}-cyclohexyl)-ethyl ester | Ethylamine |
| 22.6 | trans-[2-(4-{2-[Ethyl-(2-hydroxy-ethyl)-amino]-ethyl}-cyclohexyl)-ethyl]-methyl-carbamic acid 4-chloro-phenyl ester | 411 (1 Cl) | trans-Methanesulfonic acid 2-(4-{2-[(4-chloro-phenoxycarbonyl)-methyl-amino]-ethyl}-cyclohexyl)-ethyl ester | Ethyl-(2-hydroxy-ethyl)-amine |
| 22.7 | trans-Methyl-{2-[4-(2-methylamino-ethyl)-cyclohexyl]-ethyl}-carbamic acid 4-chloro-phenyl ester | 353 (1 Cl) | trans-Methanesulfonic acid 2-(4-{2-[(4-chloro-phenoxycarbonyl)-methyl-amino]-ethyl}-cyclohexyl)-ethyl ester | Methylamine |
| 22.8 | trans-(2-{4-[2-(6-Hydroxy-hexylamino)-ethyl]-cyclohexyl}-ethyl)-methyl-carbamic acid 4-chloro-phenyl ester | 439 (1 Cl) | trans-Methanesulfonic acid 2-(4-{2-[(4-chloro-phenoxycarbonyl)-methyl-amino]-ethyl}-cyclohexyl)-ethyl ester | 6-Hydroxy-hexylamine |
| 22.9 | trans-(2-{4-[2-(5-Hydroxy-pentylamino)-ethyl]-cyclohexyl}-ethyl)-methyl-carbamic acid 4-chloro-phenyl ester | 425 (1 Cl) | trans-Methanesulfonic acid 2-(4-{2-[(4-chloro-phenoxycarbonyl)-methyl-amino]-ethyl}-cyclohexyl)-ethyl ester | 5-Hydroxy-pentylamine |
| 22.10 | trans-4-Chloro-N-{2-[4-(2-dimethylamino-ethyl)-cyclohexyl]-ethyl}-N-methyl-benzenesulfonamide | 387 (1 Cl) | trans-Methanesulfonic acid 2-(4-{2-[(4-chloro-benzenesulfonyl)-methyl-amino]-ethyl}-cyclohexyl)-ethyl ester | Dimethylamine |
| 22.11 | trans-N-(2-{4-[2-(Allyl-methyl-amino)-ethyl]-cyclohexyl}-ethyl)-4-chloro-N-methyl-benzenesulfonamide | 413 (1 Cl) | trans-Methanesulfonic acid 2-(4-{2-[(4-chloro-benzenesulfonyl)-methyl-amino]-ethyl}-cyclohexyl)-ethyl ester | N-Allyl-methyl-amine |
| 22.12 | trans-4-Chloro-N-methyl-N-{2-[4-(2-methylamino-ethyl)-cyclohexyl]-ethyl}-benzenesulfonamide | 373 (1 Cl) | trans-Methanesulfonic acid 2-(4-{2-[(4-chloro-benzenesulfonyl)-methyl-amino]-ethyl}-cyclohexyl)-ethyl ester | Methylamine |

-continued

| Example | Product | MS MH+ | Methanesulfonic acid esters | Amine |
|---|---|---|---|---|
| 22.13 | trans-4-Chloro-N-{2-[4-(2-ethylamino-ethyl)-cyclohexyl]-ethyl}-N-methyl-benzenesulfonamide | 387 (1 Cl) | trans-Methanesulfonic acid 2-(4-{2-[(4-chloro-benzenesulfonyl)-methyl-amino]-ethyl}-cyclohexyl)-ethyl ester | Ethylamine |
| 22.14 | trans-4-Chloro-N-[2-(4-{2-[ethyl-(2-hydroxy-ethyl)-amino]-ethyl}-cyclohexyl)-ethyl]-N-methyl-benzenesulfonamide | 431 (1 Cl) | trans-Methanesulfonic acid 2-(4-{2-[(4-chloro-benzenesulfonyl)-methyl-amino]-ethyl}-cyclohexyl)-ethyl ester | Ethyl-(2-hydroxy-ethyl)-amine |

Example 23

23.1

A solution of 257.6 g (982 mmol) triphenylphosphine in 1 l methylenechloride was treated with 162.8 g (491 mmol) tetrabromomethane (the reaction was heated up to reflux and was then cooled with an ice bath) and after 40 minutes at room temperature treated with 157.4 ml (1129 mmol) tri-ethylamine (the reaction was heated up to reflux and became dark violet). After cooling (0° C.), 62.7 g (245.5 mmol) of trans-(4-formyl-cyclohexylmethyl)-methyl-carbamic acid tert-butyl ester (example 1.2) in 600 ml methylenechloride were added during 20 minutes. The solution was stirred for 20 hours at room temperature, evaporated and filtered through silica gel (deactivated with hexane/Et₃N) with a 99:1 to 4:1 v/v mixture of hexane and ether as eluent to yield 61.5 g (61%) of trans-[4-(2,2-dibromo-vinyl)-cyclohexylmethyl]-methyl-carbamic acid tert-butyl ester as brown oil, MS: 409 (M, 2Br).

23.2

A solution of 32.9 g (80 mmol) of trans-[4-(2,2-dibromo-vinyl)-cyclohexylmethyl]-methyl-carbamic acid tert-butyl ester in 640 ml tetrahydrofuran was treated at −78° C. with 105 ml (168 mmol) of n-butyl-lithium (ca 1.6 M in hexane). After 2 hours at this temperature, 24 g (800 mmol) of paraformaldehyde were added. The reaction mixture was warmed up to room temperature for 3 hours and after 0.5 hours at this temperature extracted with water/ether (3×). The organic phases were washed with aqueous 10% NaCl, dried over sodium sulfate and evaporated. Purification by flash-chromatography on silica gel (hexane/EtOAc 9:1 to 2:1) yielded 12.1 g (54%) of trans-[4-(3-hydroxy-prop-1-ynyl)-cyclohexylmethyl]-methyl-carbamic acid tert-butyl ester as orange viscous oil, MS: 282 (MH+).

23.3

A solution of 8.16 g (29 mmol) of trans-[4-(3-hydroxy-prop-1-ynyl)-cyclohexylmethyl]-methyl-carbamic acid tert-butyl ester in 230 ml methylenechloride was treated at 0° C. with 2.48 ml (31.9 mmol) of methanesulfonylchloride and 5.05 ml (43.5 mmol) of 2,6-lutidine. The reaction mixture was stirred over night to room temperature. The reaction was cooled (0° C.) and treated again with 0.68 ml (8.7 mmol) of methanesulfonylchloride and 1.68 ml (14.5 mmol) of 2,6-lutidine and stirred for 24 hours. Water (35 ml) was added and the reaction was stirred for 5 minutes. After extraction with aqueous saturated NaHCO₃/ether (3×), the organic phases were washed with aqueous 10% NaCl, dried over sodium sulfate and evaporated to yield 12.5 g of crude trans-methanesulfonic acid 3-{4-[(tert-butoxycarbonyl-methyl-amino)-methyl]-cyclohexyl}-prop-2-ynyl ester as brown oil, MS: 360 (MH+).

23.4

A solution of 12.5 g (corresponds to 28.9 mmol) of crude trans-methanesulfonic acid 3-{4-[(tert-butoxycarbonyl-methyl-amino)-methyl]-cyclohexyl}-prop-2-ynyl ester in 160 ml methylenechloride was treated at 0° C. with 78 ml of trifluoroacetic acid (for 30 minutes). After 15 minutes at this temperature, the reaction was evaporated, redissolved in toluene and evaporated (4×) to give 23.12 g of crude trans-methanesulfonic acid 3-(4-methylaminomethyl-cyclohexyl)-prop-2-ynyl ester trifluoro-acetate as dark brown viscous oil, MS: 260 (MH+).

23.5

A solution of 7.70 g (corresponds to 9.63 mmol) of crude trans-methanesulfonic acid 3-(4-methylaminomethyl-cyclohexyl)-prop-2-ynyl ester trifluoro-acetate in 60 ml methylenechloride was treated at 0° C. with 1.61 ml (11.56 mmol) 4-chlorophenylchloroformate and then during 3 minutes with 8.25 ml (48.17 mmol; 5 equivalents) of Huenig's base. The reaction was stirred 45 hours at room temperature and extracted with aqueous 10% KHSO₄/ether (3×). The organic phases were washed with aqueous 10% NaCl and dried over sodium sulfate to yield 5.3 g of crude trans-methanesulfonic acid 3-(4-{[(4-chloro-phenoxycarbonyl)-methyl-amino]-methyl}-cyclohexyl)-prop-2-ynyl ester as dark brown oil, MS: 414 (MH+, 1Cl).

23.6

In analogy to example 23.5, trans-methanesulfonic acid 3-(4-methylaminomethyl-cyclohexyl)-prop-2-ynyl ester trifluoro-acetate and 4-trifluoromethylbenzenesulfonyl chloride gave trans-methanesulfonic acid 3-(4-{[methyl-(4-trifluoromethylbenzene-sulfonyl)-amino]-methyl}-cyclohexyl)-prop-2-ynyl ester as dark brown oil, MS: 468 (MH+).

23.7

In analogy to example 23.5, trans-methanesulfonic acid 3-(4-methylaminomethyl-cyclohexyl)-prop-2-ynyl ester trifluoro-acetate and 4-trifluorophenylchloroformate gave trans-methanesulfonic acid 3-(4-{[methyl-(4-trifluoromethyl-phenoxycarbonyl)-amino]-methyl}-cyclohexyl)-prop-2-ynyl ester as dark brown oil, MS: 448 (MH+).

Example 24

24.1

A solution of 222 mg (corresponds to 0.40 mmol) of crude trans-methanesulfonic acid 3-(4-{[(4-chloro-phenoxycarbonyl)-methyl-amino]-methyl}-cyclohexyl)-prop-2-ynyl ester in 4 ml of methanol was cooled to 0° C., treated with 0.34 ml (4 mmol) of piperidine and stirred over night at room temperature. The solvent was evaporated and the residue extracted with aqueous saturated NaHCO₃/ether (3x). The organic phase was dried with sodium sulfate, filtered and evaporated. Purification by flash column chromatography on silica gel (methylenechloride/methanol 99:1 to 98:2) gave 92 mg (57%) of pure trans-methyl-[4-(3-piperidin-1-yl-prop-1-ynyl)-cyclohexylmethyl]-carbamic acid 4-chloro-phenyl ester as light yellow viscous oil, MS: 403 (MH$^+$, 1Cl). The following compounds were prepared from the corresponding mesylates and secondary amines:

| Example | Product | MS MH$^+$ | Methanesulfonic acid esters | Amine |
|---|---|---|---|---|
| 24.2 | trans-(4-{3-[Ethyl-(2-hydroxy-ethyl)-amino]-prop-1-ynyl}-cyclohexylmethyl)-methyl-carbamic acid 4-chloro-phenyl ester | 407 (1 Cl) | trans-Methanesulfonic acid 3-(4-{[(4-chloro-phenoxycarbonyl)-methyl-amino]-methyl}-cyclohexyl)-prop-2-ynyl ester | Ethyl-(2-hydroxy-ethyl)-amine |
| 24.3 | trans-N-Methyl-N-[4-(3-piperidin-1-yl-prop-1-ynyl)-cyclohexylmethyl]-4-trifluoromethyl-benzenesulfonamide | 457 | trans-Methanesulfonic acid 3-(4-{[methyl-(4-trifluoromethyl-benzenesulfonyl)-amino]-methyl}-cyclohexyl)-prop-2-ynyl ester | Piperidine |
| 24.4 | trans-N-(4-{3-[Ethyl-(2-hydroxy-ethyl)-amino]-prop-1-ynyl}-cyclohexylmethyl)-N-methyl-4-trifluoromethyl-benzenesulfonamide | 461 | trans-Methanesulfonic acid 3-(4-{[methyl-(4-trifluoromethyl-benzenesulfonyl)-amino]-methyl}-cyclohexyl)-prop-2-ynyl ester | Ethyl-(2-hydroxy-ethyl)-amine |
| 24.5 | trans-Methyl-[4-(3-piperidin-1-yl-prop-1-ynyl)-cyclohexylmethyl]-carbamic acid 4-trifluoromethyl-phenyl ester | 437 | trans-Methanesulfonic acid 3-(4-{[methyl-(4-trifluoromethyl-phenoxycarbonyl)-amino]-methyl}-cyclohexyl)-prop-2-ynyl ester | Piperidine |
| 24.6 | trans-(4-{3-[Ethyl-(2-hydroxy-ethyl)-amino]-prop-1-ynyl}-cyclohexylmethyl)-methyl-carbamic acid 4-trifluoromethyl-phenyl ester | 441 | trans-Methanesulfonic acid 3-(4-{[methyl-(4-trifluoromethyl-phenoxycarbonyl)-amino]-methyl}-cyclohexyl)-prop-2-ynyl ester | Ethyl-(2-hydroxy-ethyl)-amine |

Example 25

25.1

To an ice-cooled solution of 200 mg (0.46 mmol) trans-methanesulfonic acid 3-(4-{2-[(4-chloro-phenoxycarbonyl)-methyl-amino]-ethyl}-cyclohexyl)-propyl ester (example 11.16) and 126 mg (1.85 mmol) of imidazole in 3.5 ml of N,N-dimethylformamide was added at 0° C. 30.3 mg (0.69 mmol) of sodium hydride (55% in oil). The reaction mixture was then stirred for 4 hours at room temperature. After quenching with ammonium chloride solution, the reaction mixture was partitioned between water and ether. The combined ether phases were washed with brine, dried over magnesium sulfate and evaporated under reduced pressure. The residue formed was chromatographed on silica gel with a 95:5 v/v mixture of ethylacetate and methanol as the eluent giving 103 mg (55%) of pure trans-{2-[4-(3-imidazol-1-yl-propyl)-cyclohexyl]-ethyl}-methyl-carbamic acid 4-chloro-phenyl ester as colorless viscous oil, MS: 404 (MH$^+$).

25.2

In analogy to the procedure described in example 25.1, trans-methanesulfonic acid 4-{2-[methyl-(4-trifluoromethyl-benzenesulfonyl)-amino]-ethyl}-cyclohexylmethyl ester (example 13.2) was reacted with imidazole in N,N-dimethylformamide in the presence of sodium hydride to yield trans-N-[2-(4-imidazol-1-ylmethyl-cyclohexyl)-ethyl]-N-methyl-4-trifluoromethyl-benzenesulfonamide as colorless viscous oil, MS: 430 (MH$^+$).

25.3

In analogy to the procedure described in example 25.1, trans-methanesulfonic acid 4-{[methyl-(4-trifluoromethyl-benzenesulfonyl)-amino]-methyl}-cyclohexylmethyl ester (example 5.2) was reacted with imidazole in N,N-dimethylformamide in the presence of sodium hydride to yield trans-N-(4-imidazol-1-ylmethyl-cyclohexylmethyl)-N-methyl-4-trifluoromethyl-benzenesulfonamide as colorless solid, MS: 416 (MH$^+$).

25.4

In analogy to the procedure described in example 25.1, trans-N-[4-(3-chloro-(E,Z)-propenyl)-cyclohexylmethyl]-N-methyl-4-trifluoromethyl-benzenesulfonamide (E:Z=9:1) (example 17.6) was reacted with imidazole in N,N-dimethylformamide in the presence of sodium hydride to yield trans-N-[4-(3-imidazol-1-yl-(E,Z)-propenyl)-cyclohexylmethyl]-N-methyl-4-trifluoromethyl-benzenesulfonamide (E:Z=9:1) as yellowish solid, MS: 442 (MH$^+$).

25.5

In analogy to the procedure described in example 25.1, trans-methanesulfonic acid 2-(4-{[methyl-(4-trifluoromethyl-benzenesulfonyl)-amino]-methyl}-cyclohexyl)-ethyl ester (example 9.10) was reacted with imidazole in N,N-dimethylformamide in the presence of sodium hydride to yield trans-N-[4-(2-imidazol-1-yl-ethyl)-cyclohexylmethyl]-N-methyl-4-trifluoromethyl-benzenesulfonamide as yellowish solid, MS: 430 (MH$^+$).

25.6

In analogy to the procedure described in example 25.1, trans-N-[4-(4-bromo-(E)-but-2-enyloxymethyl)- cyclohexylmethyl]-N-methyl-4-trifluoromethyl-benzenesulfonamide (example 19.1) was reacted with imidazole in N,N-dimethylformamide in the presence of sodium hydride to yield trans-N-[4-(4-imidazol-1-yl-(E)-but-2-enyloxymethyl)-cyclohexylmethyl]-N-methyl-4-trifluoromethyl-benzenesulfonamide as yellowish solid, MS: 486 (MH$^+$).

Example 26

26.1

A solution of 77 mg (0.17 mmol) trans-N-methyl-N-[4-(4-methylamino-(E)-but-2-enyloxymethyl)-cyclohexylmethyl]-4-trifluoromethyl-benzenesulfonamide (example 20.6), 0.044 g (0.34 mmol) of 4-chloro-2-methyl-pyrimidine [Ger. Offen. (1990), DE3905364 A1] and 0.06 ml (0.34 mmol) N-ethyl-diisopropylamine in 1 ml of N,N-dimethylformamide was stirred for 2 hours at 80° C. The reaction mixture was then cooled to room temperature, poured into 30 ml of ice-water and extracted 3 times with 10 ml of ether. The combined ether phases were washed with brine, dried over magnesium sulfate and evaporated under reduced pressure. The residue formed was chromatographed on silica gel with a 95:5:1 v/v/v mixture of dichloromethane, methanol and saturated aqueous ammonia as the eluent giving 55 mg (59%) trans-N-methyl-N-(4-{methyl-(2-methyl-pyrimidin-4-yl)-amino]-(E)-but-2-enyloxymethyl}-cyclohexylmethyl)-4-trifluoromethyl-benzenesulfonamide as yellowish viscous oil, MS: 541 (MH$^+$).

Example 27

A mixture of 702 mg (1.63 mmol) [trans-(2-(4-{[ethyl-(2-hydroxy-ethyl)-amino]-methyl}-cyclohexyl)-ethyl]-methyl-carbamic acid 4-trifluoromethyl-phenyl ester, 256.6 mg (1.8 mmol) of phthalic anhydride and 335 mg (3.54 mmol) of Hydrogen peroxide•Urea adduct in 7 ml of $CH_2Cl_2$, was stirred for two days at RT. Additional 100 mg (1.06 mmol) of Hydrogen peroxide•Urea adduct and 50 mg (0.34 mmol) of phthalic anhydride were added to the reaction mixture. After another 3 h at RT, 10 ml of aqueous saturated $NaHCO_3$ were added. After stirring for 10 min at RT, the reaction-mixture was taken up in ether/water. The ether phase was dried and evaporated under reduced pressure. The residue was chromatographed on silica gel with a 9:1 v/v mixture of methylenchloide/methanol as eluent giving 449 mg (62%) of pure rac-trans-ethyl(2-hydroxyethyl)({4-[2-(methyl{[4-(trifluoromethyl)phenoxy]carbonyl}amino)ethyl]cyclohexyl}methyl)ammoniumolate, MS: 447 (MH$^+$).

Example 28

28.1

A solution of 10.6 g (corresponds to 5.1 g, 14.2 mmol) of crude trans-methanesulfonic acid 3-{4-[(tert-butoxycarbonyl-methyl-amino)-methyl]-cyclohexyl}-prop-2-ynyl ester in 210 ml ethanol was treated at 0° C. with 18.1 ml (142 mmol) of 7.8 N HCl in ethanol. After 4 hours at room temperature, the reaction was evaporated to give 12.06 g of crude trans-[4-(3-chloro-prop-1-ynyl)-cyclohexylmethyl]-methyl-amine. HCl as brown semisolid, MS: 199 (MH$^+$, 1Cl).

28.2

A solution of 12.06 g (corresponds to 14.2 mmol) of crude trans-[4-(3-chloro-prop-1-ynyl)-cyclohexylmethyl]-methyl-amine.HCl in 100 ml methylenechloride was treated at 0° C. with 2.97 g (17.0 mmol) 4-fluorophenylchloroformate and then during 3 minutes with 12.1 ml (70.9 mmol; 5 equivalents) of Huenig's base. The reaction was stirred 2 hours at room temperature and extracted with aqueous 10% $KHSO_4$/ether (3×). The organic phases were washed with aqueous 10% NaCl and dried over sodium sulfate to yield 5.53 g (98%) of trans-[4-(3-chloro-prop-1-ynyl)-cyclohexylmethyl]-methyl-carbamic acid 4-fluoro-phenyl ester as a brown oil, MS: 338 (MH$^+$, 1Cl).

Example 29

29.1

A solution of 250 mg (0.63 mmol) of trans-[4-(3-chloro-prop-1-ynyl)cyclohexyl-methyl]-methyl-carbamic acid 4-fluoro-phenyl ester with a catalytic amount of NaI in 7 ml of methanol was treated with 0.65 ml (6.3 mmol) of N-methylpropylamine and stirred over night at room temperature. The solvent was evaporated and the residue extracted with aqueous saturated $NaHCO_3$/ether (3×). The organic phase was dried with sodium sulfate, filtered and evaporated. Purification by flash column chromatography on silica gel (methylenechloride/methanol 98:2) gave 218 mg (93%) of pure trans-methyl-{4-[3-(methyl-propyl-amino)-prop-1-ynyl]-cyclohexylmethyl}-carbamic acid 4-fluoro-phenyl ester as light brown oil, MS: 375 (MH$^+$).

The following compounds were prepared from the corresponding chloride and secondary amines:

| Example | Product | MS MH$^+$ | Chloride | Amine |
|---|---|---|---|---|
| 29.2 | trans-(4-{3-[Ethyl-(2-hydroxy-ethyl)-amino]-prop-1-ynyl}-cyclohexylmethyl)-methyl-carbamic acid 4-fluoro-phenyl ester | 391 | trans-[4-(3-chloro-prop-1-ynyl)-cyclohexylmethyl]-methyl-carbamic acid 4-fluoro-phenyl ester | Ethyl-(2-hydroxy-ethyl)-amine |
| 29.3 | trans-[4-(3-Dimethylamino-prop-1-ynyl)-cyclohexylmethyl]-methyl-carbamic acid 4-fluoro-phenyl ester | 347 | trans-[4-(3-chloro-prop-1-ynyl)-cyclohexylmethyl]-methyl-carbamic acid 4-fluoro-phenyl ester | Dimethylamine |

EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |

-continued

| Ingredients | Per tablet | |
|---|---|---|
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |

-continued

| Capsule contents | |
|---|---|
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:

1. A compound of formula (I):

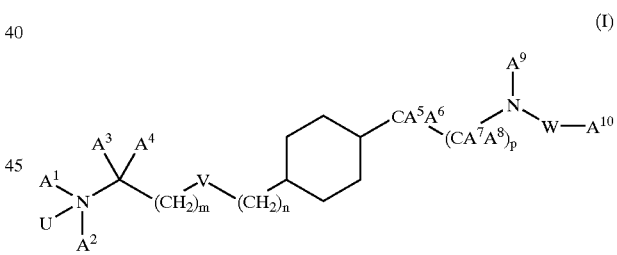

wherein
U is O or a lone pair,
V is a single bond, or —$CH_2$—,
W is $SO_2$,
m and n independently from each other are from 0 to 7 and m+n is from 0 to 7, with the proviso that m is not 0 if V is O or S,
$A^1$ is hydrogen, lower-alkyl, hydroxy-lower-alkyl, or lower-alkenyl,
$A^2$ is 3 to 6 carbon atoms cycloalkyl, 3 or 6 carbon atoms cycloalkyl-lower-alkyl, lower-alkenyl, lower-alkynyl, heteroaryl, which is an aromatic 5- to 6-membered ring comprising 1 to 3 hetero atom selected from nitrogen, oxygen and sulphur, substituted heteroaryl, or lower-alkyl optionally substutited by $R^2$, or
$A^1$ and $A^2$ are bonded to each other to form a ring with the N atom to which they are attached, and —$A^1$—$A^2$— is lower-alkylene or lower-alkenylene, optionally substituted by $R^2$, in which one —$CH_2$— group of —$A^1$—$A^2$— can optionally be replaced by $NR^3$, S, or O, or —$A^1$—$A^2$— is —CH=N—CH=CH— which can optionally be substituted by lower-alkyl, $A^3$ and $A^4$ independently from each other are hydrogen or lower-alkyl, or $A^3$ and $A^4$ are bonded to each other to form a ring together with the carbon atom to which they are attached and —$A^3$—$A^4$— is —$(CH_2)_{2-5}$—, $A^5$, $A^6$, $A^7$ and $A^8$ independently from each other are hydrogen or lower-alkyl, $A^9$ is hydrogen, lower-alkyl, lower-alkenyl, or aryl-lower-alkyl, $A^{10}$ is aryl or substituted aryl, p is 0 or 1, $R^2$ is hydroxy, hydroxy-lower-alkyl, lower-alkoxy, lower-alkoxycarbonyl, $N(R^4,R^5)$, thio-lower-alkoxy or halogen, $R^3$, $R^4$ and $R^5$ independently from each other are hydrogen or lower-alkyl, substituted aryl and substituted heteroaryl are aryl and heteroaryl, respectively, substituted by 1 to 3 substituents independently selected from the group consisting of lower-alkyl, lower-alkynyl, dioxo-lower-alkylene, halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl, phenyl, and phenyloxy, or a pharmaceutically acceptable salts thereof, with the proviso that the compound of formula (I) is not trans-naphthalene-1-sulfonic acid methyl-(4-methylaminomethyl-cyclohexylmethyl)-amide.

2. The compound according to claim 1, wherein U is a lone pair.

3. The compound according to claim 1, wherein V is a single bond.

4. The compound according to claim 1, wherein V is a —$CH_2$—.

5. The compound according to claim 1, wherein m is from 0 to 4 and n is from 0 to 1.

6. The compound according to claim 5, wherein m is 0.

7. The compound according to claim 5, wherein n is 0.

8. The compound according to claim 1, wherein $A^1$ is hydrogen, lower-alkyl or hydroxy-lower-alkyl.

9. The compound according to claim 8, wherein $A^1$ is methyl, ethyl, or 2-hydroxy-ethyl.

10. The compound according to claim 1, wherein $A^2$ is lower-alkenyl, 2-methyl-pyrimidinyl, or lower-alkyl optionally substituted by $R^2$, wherein $R^2$ is hydroxy.

11. The compound according to claim 10, wherein $A^2$ is methyl or 2-hydroxy-ethyl.

12. The compound according to claim 1, wherein $A^1$ and $A^2$ are bonded to each other to form a ring with the N atom to which they are attached, and —$A^1$—$A^2$— is lower-alkylene optionally substituted by $R^2$, in which one —$CH_2$— group of —$A^1$—$A^2$— can optionally be replaced by $NR^3$ or O, or —$A^1$—$A^2$— is —CH=N—CH=CH—, wherein $R^2$ is hydroxy or hydroxy-lower-alkyl, and $R^3$ is hydrogen or lower-alkyl.

13. The compound according to claim 12, wherein —$A^1$—$A^2$— is —$(CH_2)_4$— or —$(CH_2)_5$—.

14. The compound according to claim 1, wherein $A^3$ and $A^4$ are hydrogen.

15. The compound according to claim 1, wherein $A^5$ and $A^6$ are hydrogen.

16. The compound according to claim 1, wherein $A^7$ and $A^8$ are hydrogen.

17. The compound according to claim 1, wherein $A^9$ is lower-alkyl.

18. The compound according to claim 17, wherein $A^9$ is methyl.

19. The compound according to claim 1, wherein $A^{10}$ is aryl.

20. The compound according to claim 1, wherein $A^{10}$ is phenyl optionally substituted with halogen or $CF_3$.

21. The compound according to claim 20, wherein $A^{10}$ is 4-chloro-phenyl or 4-trifluoromethyl-phenyl.

22. A pharmaceutical composition comprising a compound according to claim 1 and a pharmaceutically acceptable carrier.

23. A method of treatment of hypercholesterolemia or hyperlipemia, comprising administering a therapeutically effective amount of a compound or a salt thereof according to claim 1, to a patient in need of treatment.

24. A compound of formula (I):

wherein

U is a lone pair,

V is —$CH_2$—,

W is $SO_2$, m and n independently from each other are from 0 to 3 and m+n is from 0 to 3, $A^1$ is hydroxy lower-alkyl, or lower-alkyl, $A^2$ is hydroxy lower-alkyl or lower-alkyl, or $A^1$ and $A^2$ are bonded to each other to form a ring with the N atom to which they are attached, and —$A^1$—$A^2$— is lower-alkylene, $A^3$ and $A^4$ are each hydrogen, $A^5$, $A^6$, $A^7$ and $A^8$ are each hydrogen, $A^9$ is lower-alkyl, $A^{10}$ is phenyl substituted with chlorine or —$CF_3$, p is 0 or 1, or a pharmaceutically acceptable salt thereof.

25. The compound according to claim 24, wherein hydroxy lower-alkyl for each of $A^1$ and $A^2$ is —$CH_2CH_2OH$.

26. The compound according to claim 24, wherein lower alkyl for each of $A^1$ and $A^2$ is independently selected from the group consisting of —$CH_3$ and —$CH_2CH_3$.

27. The compound according to claim 24, wherein $A^9$ is —$CH_3$.

28. The compound according to claim 1, wherein said dioxo-lower-alkylene forms a benzodioxyl group.

* * * * *